United States Patent
Myllylä et al.

(10) Patent No.: US 7,341,853 B2
(45) Date of Patent: Mar. 11, 2008

(54) METHOD FOR GLYCOSYLATING HYDROXYLYSINE RESIDUES

(75) Inventors: Raili Myllylä, Oulu (FI); Jari Heikkinen, Oulu (FI); Maija Risteli, Oulu (FI); Chuanguang Wang, Oulu (FI)

(73) Assignee: Oulun Yliopisto, Oulu (FI)

( * ) Notice: Subject to any disclaimer, the term of this patent is extended or adjusted under 35 U.S.C. 154(b) by 537 days.

(21) Appl. No.: 10/276,825

(22) PCT Filed: Jun. 4, 2001

(86) PCT No.: PCT/FI01/00528

§ 371 (c)(1),
(2), (4) Date: Nov. 18, 2002

(87) PCT Pub. No.: WO01/92505

PCT Pub. Date: Dec. 6, 2001

(65) Prior Publication Data

US 2005/0048600 A1    Mar. 3, 2005

(30) Foreign Application Priority Data

Jun. 2, 2000    (FI)    ................................. 20001328

(51) Int. Cl.
C12P 19/00    (2006.01)
C12N 9/02    (2006.01)
C12N 1/20    (2006.01)
C12N 15/00    (2006.01)
C07H 21/04    (2006.01)

(52) U.S. Cl. .................... 435/72; 435/41; 435/183; 435/189; 435/252.3; 435/320.1; 536/23.2

(58) Field of Classification Search .................. 435/41, 435/72, 74, 183, 189, 252.3, 320.1; 536/23.2
See application file for complete search history.

(56) References Cited

U.S. PATENT DOCUMENTS 6,130,039 A    10/2000    Bandman et al.

FOREIGN PATENT DOCUMENTS

WO    WO 00/61755 A2    10/2000

OTHER PUBLICATIONS

Valtavarra et al. J Biol Chem. May 22, 1998;273(21):12881-6.*
Valtavarra et al. GenBank Accession AF046889. Mar. 27, 1998.*
Heikkinen et al. J. Biol. Chem. Nov. 17, 2000;275 (46): 36158-163.*
Spiro et al. J. Biol Chem. Aug. 25, 1971;246(16):4910-8.*
Passoja et al., Proc. Natl. Acad. Sci., vol. 95, pp. 10482-10486 (1998).
Valtavaara et al., The Journal of Biological Chemistry, vol. 273, No. 21, pp. 12881-12886 (1998).
Valtavaara et al., The Journal of Biological Chemistry, vol. 272, No. 11, pp. 6831-3834 (1997).
Routsalainen et al., Matrix Biology, vol. 18, pp. 325-329 (1999).
Yeowell et al., Journal of Invest. Dermatol., vol. 99, No. 6, pp. 864-869 (1992).
Routsalainen et al., Matrix Biology, vol. 20, pp. 137-146 (2001).
Heikkinen et al., The Journal of Biological Chemistry, vol. 275, No. 46, pp. 36158-36163 (2000).
Hautala et al., Gemomics, vol. 13, pp. 62-69 (1992).
Croyle et al., DNA, vol. 5, No. 4, pp. 299-304 (1986).
Myllyla et al., The Journal of Biological Chemistry, vol. 266, No. 5, pp. 2805-2810 (1991).

* cited by examiner

*Primary Examiner*—Tekchand Saidha
*Assistant Examiner*—Christian L. Fronda
(74) *Attorney, Agent, or Firm*—Birch, Stewart, Kolasch & Birch, LLP

(57) ABSTRACT

This invention relates to a multifunctional enzyme having lysyl hydroxylase and glycosyltransferase activity and to the use of the enzyme in glycosylating hydroxylysine residues. In particular this invention relates to a method for producing glycosyltransferase activity, which comprises that a nucleotide sequence encoding lysyl hydroxylase and glycosyltransferase activity is introduced and expressed in a chosen host and the protein product is recovered from the host cell or from the culture medium.

19 Claims, 20 Drawing Sheets

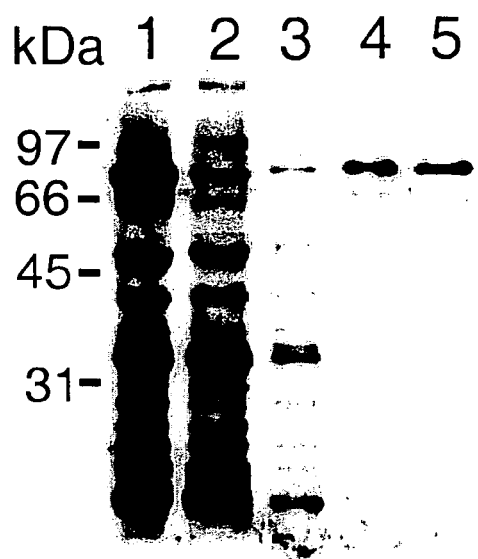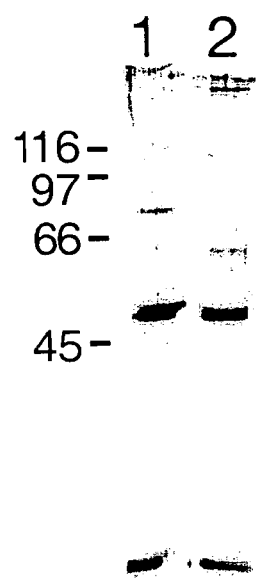
Fig. 2a
Fig. 2b
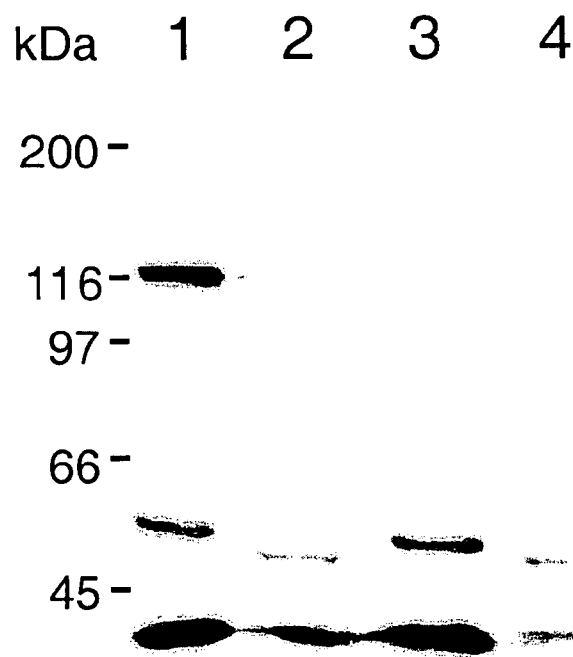
Fig. 2c

A

B

A

B

```
214                                             ACC ATG ACC TCC TCG GGG CCT GGA CCC  240
  1                                                 M   T   S   G   P   G   P      8

241 CGG TTC CTG CTG CTG CTG CCG CTG CTG CCC CCT GCG GCC TCA GCC TCC GAC CGG CCC  300
  9  R   F   L   L   L   L   P   L   L   P   P   A   A   S   A   S   D   R   P    28

301 CGG GGC CGA GAC CCG GTC AAC CCA GAG AAG CTG CTG GTG ATC ACT GTG GCC ACA GCT GAA  360
 29  R   G   R   D   P   V   N   P   E   K   L   L   V   I   T   V   A   T   A   E  48

361 ACC GAG GGG TAC CTG CGT TTC CTG CGC TCT GCG GAG TTC TTC AAC TAC ACT GTG CGG ACC  420
 49  T   E   G   Y   L   R   F   L   R   S   A   E   F   F   N   Y   T   V   R   T  68

421 CTG GGC CTG GGA GAG GAG TGG CGA GGG GGT GAT GTG GCT CGA ACA GTT GGT GGA GGA CAG  480
 69  L   G   L   G   E   E   W   R   G   G   D   V   A   R   T   V   G   G   G   Q  88

481 AAG GTC CGG TGG TTA AAG AAG GAA ATG GAG AAA TAC GCT GAC CGG GAG GAT ATG ATC ATC  540
 89  K   V   R   W   L   K   K   E   M   E   K   Y   A   D   R   E   D   M   I   I  108

541 ATG TTT GTG GAT AGC TAC GAC GTG ATT CTG GCC GGC AGC CCC ACA GAG CTG CTG AAG AAG  600
109  M   F   V   D   S   Y   D   V   I   L   A   G   S   P   T   E   L   L   K   K  128

601 TTC GTC CAG AGT GGC AGC CGC CTG CTC TTC TCT GCA GAG AGC TTC TGC TGG CCC GAG TGG  660
129  F   V   Q   S   G   S   R   L   L   F   S   A   E   S   F   C   W   P   E   W  148

661 GGG CTG GCG GAG CAG TAC CCT GAG GTG GGC ACG GGG AAG CGC TTC CTC AAT TCT GGT GGA  720
149  G   L   A   E   Q   Y   P   E   V   G   T   G   K   R   F   L   N   S   G   G  168

721 TTC ATC GGT TTT GCC ACC ACC ATC CAC CAA ATC GTG CGC CAG TGG AAG TAC AAG GAT GAT  780
169  F   I   G   F   A   T   T   I   H   Q   I   V   R   Q   W   K   Y   K   D   D  188

781 GAC GAC GAC CAG CTG TTC TAC ACA CGG CTC TAC CTG GAC CCA GGA CTG AGG GAG AAA CTC  840
189  D   D   D   Q   L   F   Y   T   R   L   Y   L   D   P   G   L   R   E   K   L  208

841 AGC CTT AAT CTG GAT CAT AAG TCT CGG ATC TTT CAG AAC CTC AAC GGG GCT TTA GAT GAA  900
209  S   L   N   L   D   H   K   S   R   I   F   Q   N   L   N   G   A   L   D   E  228

901 GTG GTT TTA AAG TTT GAT CGG AAC CGT GTG CGT ATC CGG AAC GTG GCC TAC GAC ACG CTC  960
229  V   V   L   K   F   D   R   N   R   V   R   I   R   N   V   A   Y   D   T   L  248

961 CCC ATT GTG GTC CAT GGA AAC GGT CCC ACT AAG CTG CAG CTC AAC TAC CTG GGA AAC TAC 1020
249  P   I   V   V   H   G   N   G   P   T   K   L   Q   L   N   Y   L   G   N   Y  268

1021 GTC CCC AAT GGC TGG ACT CCT GAG GGA GGC TGT GGC TTC TGC AAC CAG GAC CGG AGG ACA 1080
 269  V   P   N   G   W   T   P   E   G   G   C   G   F   C   N   Q   D   R   R   T  288

1081 CTC CCG GGG GGG CAG CCT CCC CCC CGG GTG TTT CTG GCC GTG TTT GTG GAA CAG CCT ACT 1140
 289  L   P   G   G   Q   P   P   P   R   V   F   L   A   V   F   V   E   Q   P   T  308

1141 CCG TTT CTG CCC CGC TTC CTG CAG CGG CTG CTA CTC CTG GAC TAT CCC CCC GAC AGG GTC 1200
 309  P   F   L   P   R   F   L   Q   R   L   L   L   L   D   Y   P   P   D   R   V  328

1201 ACC CTT TTC CTG CAC AAC AAC GAG GTC TTC CAT GAA CCC CAC ATC GCT GAC TCC TGG CCG 1260
 329  T   L   F   L   H   N   N   E   V   F   H   E   P   H   I   A   D   S   W   P  348

1261 CAG CTC CAG GAC CAC TTC TCA GCT GTG AAG CTC GTG GGG CCG GAG GAG GCT CTG AGC CCA 1320
 349  Q   L   Q   D   H   F   S   A   V   K   L   V   G   P   E   E   A   L   S   P  368

1321 GGC GAG GCC AGG GAC ATG GCC ATG GAC CTG TGT CGG CAG GAC CCC GAG TGT GAG TTC TAC 1380
 369  G   E   A   R   D   M   A   M   D   L   C   R   Q   D   P   E   C   E   F   Y  388

1381 TTC AGC CTG GAC GCC GAC GCT GTC CTC ACC AAC CTG CAG ACC CTG CGT ATC CTC ATT GAG 1440
 389  F   S   L   D   A   D   A   V   L   T   N   L   Q   T   L   R   I   L   I   E  408

1441 GAG AAC AGG AAG GTG ATC GCC CCC ATG CTG TCC CGC CAC GGC AAG CTG TGG TCC AAC TTC 1500
 409  E   N   R   K   V   I   A   P   M   L   S   R   H   G   K   L   W   S   N   F  428

1501 TGG GGC GCC CTG AGC CCC GAT GAG TAC TAC GCC CGC TCC GAG GAC TAC GTG GAG CTG GTG 1560
 429  W   G   A   L   S   P   D   E   Y   Y   A   R   S   E   D   Y   V   E   L   V  448

1561 CAG CGG AAG CGA GTG GGT GTG TGG AAT GTA CCA TAC ATC TCC CAG GCC TAT GTG ATC CGG 1620
 449  Q   R   K   R   V   G   V   W   N   V   P   Y   I   S   Q   A   Y   V   I   R  468

1621 GGT GAT ACC CTG CGG ATG GAG CTG CCC CAG AGG GAT GTG TTC TCG GGC AGT GAC ACA GAC 1680
 469  G   D   T   L   R   M   E   L   P   Q   R   D   V   F   S   G   S   D   T   D  488

1681 CCG GAC ATG GCC TTC TGT AAG AGC TTT CGA GAC AAG GGC ATC TTC CTC CAT CTG AGC AAT 1740
 489  P   D   M   A   F   C   K   S   F   R   D   K   G   I   F   L   H   L   S   N  508
```

Fig. 6A

```
1741 CAG CAT GAA TTT GGC CGG CTC CTG GCC ACT TCC AGA TAC GAC ACG GAG CAC CTG CAC CCC 1800
 509  Q   H   E   F   G   R   L   L   A   T   S   R   Y   D   T   E   H   L   H   P   528

1801 GAC CTC TGG CAG ATC TTC GAC AAC CCC GTC GAC TGG AAG GAG CAG TAC ATC CAC GAG AAC 1860
 529  D   L   W   Q   I   F   D   N   P   V   D   W   K   E   Q   Y   I   H   E   N   548

1861 TAC AGC CGG GCC CTG GAA GGG GAA GGA ATC GTG GAG CAG CCA TGC CCG GAC GTG TAC TGG 1920
 549  Y   S   R   A   L   E   G   E   G   I   V   E   Q   P   C   P   D   V   Y   W   568

1921 TTC CCA CTG CTG TCA GAA CAA ATG TGT GAT GAG CTG GTG GCA GAG ATG GAG CAC TAC GGC 1980
 569  F   P   L   L   S   E   Q   M   C   D   E   L   V   A   E   M   E   H   Y   G   588

1981 CAG TGG TCA GGC GGC CGG CAT GAG GAT TCA AGG CTG GCT GGA GGC TAC GAG AAT GTG CCC 2040
 589  Q   W   S   G   G   R   H   E   D   S   R   L   A   G   G   Y   E   N   V   P   608

2041 ACC GTG GAC ATC CAC ATG AAG CAG GTG GGG TAC GAG GAC CAG TGG CTG CAG CTG CTG CGG 2100
 609  T   V   D   I   H   M   K   Q   V   G   Y   E   D   Q   W   L   Q   L   L   R   628

2101 ACG TAT GTG GGC CCC ATG ACC GAG AGC CTG TTT CCC GGT TAC CAC ACC AAG GCG CGG GCG 2160
 629  T   Y   V   G   P   M   T   E   S   L   F   P   G   Y   H   T   K   A   R   A   648

2161 GTG ATG AAC TTT GTG GTT CGC TAC CGG CCA GAC GAG CAG CCG TCT CTG CGG CCA CAC CAC 2220
 649  V   M   N   F   V   V   R   Y   R   P   D   E   Q   P   S   L   R   P   H   H   668

2221 GAC TCA TCC ACC TTC ACC CTC AAC GTT GCC CTC AAC CAC AAG GGC CTG GAC TAT GAG GGA 2280
 669  D   S   S   T   F   T   L   N   V   A   L   N   H   K   G   L   D   Y   E   G   688

2281 GGT GGC TGC CGC TTC CTG CGC TAC GAC TGT GTG ATC TCC TCC CCG AGG AAG GGC TGG GCA 2340
 689  G   G   C   R   F   L   R   Y   D   C   V   I   S   S   P   R   K   G   W   A   708

2341 CTC CTG CAC CCC GGC CGC CTC ACC CAC TAC CAC GAG GGG CTG CCA ACG ACC TGG GGC ACA 2400
 709  L   L   H   P   G   R   L   T   H   Y   H   E   G   L   P   T   T   W   G   T   728

2401 CGC TAC ATC ATG GTG TCC TTT GTC GAC CCC TGA CAC TCA ACC ACT CT                   2447
 729  R   Y   I   M   V   S   F   V   D   P   *                                      738
```

Fig. 6B

|  |  |  |  |  |  |  |  |  |  |  |  |  |  |  |  |  |  |  | TCC | GAC | CGG | CCC | 300 |
|  |  |  |  |  |  |  |  |  |  |  |  |  |  |  |  |  |  |  | S | D | R | P | 28 |

```
 301 CGG GGC CGA GAC CCG GTC AAC CCA GAG AAG CTG CTG GTG ATC ACT GTG GCC ACA GCT GAA  360
  29  R   G   R   D   P   V   N   P   E   K   L   L   V   I   T   V   A   T   A   E    48

361 ACC GAG GGG TAC CTG CGT TTC CTG CGC TCT GCG GAG TTC TTC AAC TAC ACT GTG CGG ACC  420
  49  T   E   G   Y   L   R   F   L   R   S   A   E   F   F   N   Y   T   V   R   T    68

421 CTG GGC CTG GGA GAG GAG TGG CGA GGG GGT GAT GTG GCT CGA ACA GTT GGT GGA GGA CAG  480
  69  L   G   L   G   E   E   W   R   G   G   D   V   A   R   T   V   G   G   G   Q    88

481 AAG GTC CGG TGG TTA AAG AAG GAA ATG GAG AAA TAC GCT GAC CGG GAG GAT ATG ATC ATC  540
  89  K   V   R   W   L   K   K   E   M   E   K   Y   A   D   R   E   D   M   I   I   108

541 ATG TTT GTG GAT AGC TAC GAC GTG ATT CTG GCC GGC AGC CCC ACA GAG CTG CTG AAG AAG  600
 109  M   F   V   D   S   Y   D   V   I   L   A   G   S   P   T   E   L   L   K   K   128

601 TTC GTC CAG AGT GGC AGC CGC CTG CTC TTC TCT GCA GAG AGC TTC TGC TGG CCC GAG TGG  660
 129  F   V   Q   S   G   S   R   L   L   F   S   A   E   S   F   C   W   P   E   W   148

661 GGG CTG GCG GAG CAG TAC CCT GAG GTG GGC ACG GGG AAG CGC TTC CTC AAT TCT GGT GGA  720
 149  G   L   A   E   Q   Y   P   E   V   G   T   G   K   R   F   L   N   S   G   G   168

721 TTC ATC GGT TTT GCC ACC ACC ATC CAC CAA ATC GTG CGC CAG TGG AAG TAC AAG GAT GAT  780
 169  F   I   G   F   A   T   T   I   H   Q   I   V   R   Q   W   K   Y   K   D   D   188

781 GAC GAC GAC CAG CTG TTC TAC ACA CGG CTC TAC CTG GAC CCA GGA CTG AGG GAG AAA CTC  840
 189  D   D   D   Q   L   F   Y   T   R   L   Y   L   D   P   G   L   R   E   K   L   208

841 AGC CTT AAT CTG GAT CAT AAG TCT CGG ATC TTT CAG AAC CTC AAC GGG GCT TTA GAT GAA  900
 209  S   L   N   L   D   H   K   S   R   I   F   Q   N   L   N   G   A   L   D   E   228

901 GTG GTT TTA AAG TTT GAT CGG AAC CGT GTG CGT ATC CGG AAC GTG GCC TAC GAC ACG CTC  960
 229  V   V   L   K   F   D   R   N   R   V   R   I   R   N   V   A   Y   D   T   L   248

961 CCC ATT GTG GTC CAT GGA AAC GGT CCC ACT AAG CTG CAG CTC AAC TAC CTG GGA AAC TAC 1020
 249  P   I   V   V   H   G   N   G   P   T   K   L   Q   L   N   Y   L   G   N   Y   268

1021 GTC CCC AAT GGC TGG ACT CCT GAG GGA GGC TGT GGC TTC TGC AAC CAG GAC CGG AGG ACA 1080
 269  V   P   N   G   W   T   P   E   G   G   C   G   F   C   N   Q   D   R   R   T   288

1081 CTC CCG GGG GGG CAG CCT CCC CCC CGG GTG TTT CTG GCC GTG TTT GTG GAA CAG CCT ACT 1140
 289  L   P   G   G   Q   P   P   P   R   V   F   L   A   V   F   V   E   Q   P   T   308

1141 CCG TTT CTG CCC CGC TTC CTG CAG CGG CTG CTA CTC CTG GAC TAT CCC CCC GAC AGG GTC 1200
 309  P   F   L   P   R   F   L   Q   R   L   L   L   L   D   Y   P   P   D   R   V   328

1201 ACC CTT TTC CTG CAC AAC AAC GAG GTC TTC CAT GAA CCC CAC ATC GCT GAC TCC TGG CCG 1260
 329  T   L   F   L   H   N   N   E   V   F   H   E   P   H   I   A   D   S   W   P   348

1261 CAG CTC CAG GAC CAC TTC TCA GCT GTG AAG CTC GTG GGG CCG GAG GAG GCT CTG AGC CCA 1320
 349  Q   L   Q   D   H   F   S   A   V   K   L   V   G   P   E   E   A   L   S   P   368

1321 GGC GAG GCC AGG GAC ATG GCC ATG GAC CTG TGT CGG CAG GAC CCC GAG TGT GAG TTC TAC 1380
 369  G   E   A   R   D   M   A   M   D   L   C   R   Q   D   P   E   C   E   F   Y   388

1381 TTC AGC CTG GAC GCC GAC GCT GTC CTC ACC AAC CTG CAG ACC CTG CGT ATC CTC ATT GAG 1440
 389  F   S   L   D   A   D   A   V   L   T   N   L   Q   T   L   R   I   L   I   E   408

1441 GAG AAC AGG AAG GTG ATC GCC CCC ATG CTG TCC CGC CAC GGC AAG CTG TGG TCC AAC TTC 1500
 409  E   N   R   K   V   I   A   P   M   L   S   R   H   G   K   L   W   S   N   F   428

1501 TGG GGC GCC CTG AGC CCC GAT GAG TAC TAC GCC CGC TCC GAG GAC TAC GTG GAG CTG GTG 1560
 429  W   G   A   L   S   P   D   E   Y   Y   A   R   S   E   D   Y   V   E   L   V   448

1561 CAG CGG AAG CGA GTG GGT GTG TGG AAT GTA CCA TAC ATC TCC CAG GCC TAT GTG ATC CGG 1620
 449  Q   R   K   R   V   G   V   W   N   V   P   Y   I   S   Q   A   Y   V   I   R   468

1621 GGT GAT ACC CTG CGG ATG GAG CTG CCC CAG AGG GAT GTG TTC TCG GGC AGT GAC ACA GAC 1680
 469  G   D   T   L   R   M   E   L   P   Q   R   D   V   F   S   G   S   D   T   D   488

1681 CCG GAC ATG GCC TTC TGT AAG AGC TTT CGA GAC AAG GGC ATC TTC CTC CAT CTG AGC AAT 1740
 489  P   D   M   A   F   C   K   S   F   R   D   K   G   I   F   L   H   L   S   N   508

1741 CAG CAT GAA TTT GGC CGG CTC CTG GCC ACT TCC AGA TAC GAC ACG GAG CAC CTG CAC CCC 1800
 509  Q   H   E   F   G   R   L   L   A   T   S   R   Y   D   T   E   H   L   H   P   528
```

Fig. 7A

```
1801 GAC CTC TGG CAG ATC TTC GAC AAC CCC GTC GAC TGG AAG GAG CAG TAC ATC CAC GAG AAC 1860
 529  D   L   W   Q   I   F   D   N   P   V   D   W   K   E   Q   Y   I   H   E   N   548

1861 TAC AGC CGG GCC CTG GAA GGG GAA GGA ATC GTG GAG CAG CCA TGC CCG GAC GTG TAC TGG 1920
 549  Y   S   R   A   L   E   G   E   G   I   V   E   Q   P   C   P   D   V   Y   W   568

1921 TTC CCA CTG CTG TCA GAA CAA ATG TGT GAT GAG CTG GTG GCA GAG ATG GAG CAC TAC GGC 1980
 569  F   P   L   L   S   E   Q   M   C   D   E   L   V   A   E   M   E   H   Y   G   588

1981 CAG TGG TCA GGC GGC CGG CAT GAG GAT TCA AGG CTG GCT GGA GGC TAC GAG AAT GTG CCC 2040
 589  Q   W   S   G   G   R   H   E   D   S   R   L   A   G   G   Y   E   N   V   P   608

2041 ACC GTG GAC ATC CAC ATG AAG CAG GTG GGG TAC GAG GAC CAG TGG CTG CAG CTG CTG CGG 2100
 609  T   V   D   I   H   M   K   Q   V   G   Y   E   D   Q   W   L   Q   L   L   R   628

2101 ACG TAT GTG GGC CCC ATG ACC GAG AGC CTG TTT CCC GGT TAC CAC ACC AAG GCG CGG GCG 2160
 629  T   Y   V   G   P   M   T   E   S   L   F   P   G   Y   H   T   K   A   R   A   648

2161 GTG ATG AAC TTT GTG GTT CGC TAC CGG CCA GAC GAG CAG CCG TCT CTG CGG CCA CAC CAC 2220
 649  V   M   N   F   V   V   R   Y   R   P   D   E   Q   P   S   L   R   P   H   H   668

2221 GAC TCA TCC ACC TTC ACC CTC AAC GTT GCC CTC AAC CAC AAG GGC CTG GAC TAT GAG GGA 2280
 669  D   S   S   T   F   T   L   N   V   A   L   N   H   K   G   L   D   Y   E   G   688

2281 GGT GGC TGC CGC TTC CTG CGC TAC GAC TGT GTG ATC TCC TCC CCG AGG AAG GGC TGG GCA 2340
 689  G   G   C   R   F   L   R   Y   D   C   V   I   S   S   P   R   K   G   W   A   708

2341 CTC CTG CAC CCC GGC CGC CTC ACC CAC TAC CAC GAG GGG CTG CCA ACG ACC TGG GGC ACA 2400
 709  L   L   H   P   G   R   L   T   H   Y   H   E   G   L   P   T   T   W   G   T   728

2401 CGC TAC ATC ATG GTG TCC TTT GTC GAC CCC TGA CAC TCA ACC ACT CTG CCA AAC C       2455
 729  R   Y   I   M   V   S   F   V   D   P   *                                    738
```

Fig. 7B

```
289                                                    TCC GAC CGG CCC  300
 25                                                      S   D   R   P    28

301 CGG GGC CGA GAC CCG GTC AAC CCA GAG AAG CTG CTG GTG ATC ACT GTG GCC ACA GCT GAA  360
 29  R   G   R   D   P   V   N   P   E   K   L   L   V   I   T   V   A   T   A   E   48

361 ACC GAG GGG TAC CTG CGT TTC CTG CGC TCT GCG GAG TTC TTC AAC TAC ACT GTG CGG ACC  420
 49  T   E   G   Y   L   R   F   L   R   S   A   E   F   F   N   Y   T   V   R   T   68

421 CTG GGC CTG GGA GAG GAG TGG CGA GGG GGT GAT GTG GCT CGA ACA GTT GGT GGA GGA CAG  480
 69  L   G   L   G   E   E   W   R   G   G   D   V   A   R   T   V   G   G   G   Q   88

481 AAG GTC CGG TGG TTA AAG AAG GAA ATG GAG AAA TAC GCT GAC CGG GAG GAT ATG ATC ATC  540
 89  K   V   R   W   L   K   K   E   M   E   K   Y   A   D   R   E   D   M   I   I  108

541 ATG TTT GTG GAT AGC TAC GAC GTG ATT CTG GCC GGC AGC CCC ACA GAG CTG CTG AAG AAG  600
109  M   F   V   D   S   Y   D   V   I   L   A   G   S   P   T   E   L   L   K   K  128

601 TTC GTC CAG AGT GGC AGC CGC CTG CTC TTC TCT GCA GAG AGC TTC TGC TGG CCC GAG TGG  660
129  F   V   Q   S   G   S   R   L   L   F   S   A   E   S   F   C   W   P   E   W  148

661 GGG CTG GCG GAG CAG TAC CCT GAG GTG GGC ACG GGG AAG CGC TTC CTC AAT TCT GGT GGA  720
149  G   L   A   E   Q   Y   P   E   V   G   T   G   K   R   F   L   N   S   G   G  168

721 TTC ATC GGT TTT GCC ACC ACC ATC CAC CAA ATC GTG CGC CAG TGG AAG TAC AAG GAT GAT  780
169  F   I   G   F   A   T   T   I   H   Q   I   V   R   Q   W   K   Y   K   D   D  188

781 GAC GAC GAC CAG CTG TTC TAC ACA CGG CTC TAC CTG GAC CCA GGA CTG AGG GAG AAA CTC  840
189  D   D   D   Q   L   F   Y   T   R   L   Y   L   D   P   G   L   R   E   K   L  208

841 AGC CTT AAT CTG GAT CAT AAG TCT CGG ATC TTT CAG AAC CTC AAC GGG GCT TTA GAT GAA  900
209  S   L   N   L   D   H   K   S   R   I   F   Q   N   L   N   G   A   L   D   E  228

901 GTG GTT TTA AGT TTG ATC GGA ACC GTG TGC GTA TCC GGA ACG TGG CCT ACG ACA CGC TCC  960
229  V   V   L   S   L   I   G   T   V   C   V   S   G   T   W   P   T   T   R   S  248

961 CCA TTG TGG TCC ATG GAA ACG GTC CCA CTA AGC TGC AGC TCA ACT ACC TGG GAA ACT ACG 1020
249  P   L   W   S   M   E   T   V   P   L   S   C   S   S   T   T   W   E   T   T  268

1021 TCC CCA ATG GCT GGA CTC CTG AGG GAG GCT GTG GCT TCT GCA ACC AGG ACC GGA GGA CAC 1080
269   S   P   M   A   G   L   L   R   E   A   V   A   S   A   T   R   T   G   G   H  288

1081 TCC CGG GGG GGC AGC CTC CCC CCC GGG TGT TTC TGG CCG TGT TTG TGG AAC AGC CTA CTC 1140
289   S   R   G   G   S   L   P   P   G   C   F   W   P   C   L   W   N   S   L   L  308

1141 CGT TTC TGC CCC GCT TCC TGC AGC GGC TGC TAC TCC TGG ACT ATC CCC CCG ACA GGG TCA 1200
309   R   F   C   P   A   S   C   S   G   C   Y   S   W   T   I   P   P   T   G   S  328

1201 CCC TTT TCC TGC ACA ACA ACG AGG TCT TCC ATG AAC CCC ACA TCG CTG ACT CCT GGC CGC 1260
329   P   F   S   C   T   T   T   R   S   S   M   N   P   T   S   L   T   P   G   R  348

1261 AGC TCC AGG ACC ACT TCT CAG CTG TGA AGC TCG TGG GGC CGG AGG AGG CTC TGA GCC CAG 1320
349   S   S   R   T   T   S   Q   L   *                                              356

1321 GCG AGG CCA GGG ACA TGG CCA TGG ACC TGT GTC GGC AGG ACC CCG AGT GTG AGT TCT ACT 1380

1381 TCA GCC TGG ACG CCG ACG CTG TCC TCA CCA ACC TGC AGA CCC TGC GTA TCC TCA TTG AGG 1440

1441 AGA ACA GGA AGG TGA TCG CCC CCA TGC TGT CCC GCC ACG GCA AGC TGT GGT CCA ACT CTT 1500

1501 GGG GCG CCC TGA GCC CCG ATG AGT ACT ACG CCC GCT CCG AGG ACT ACG TGG AGC TGG TGC 1560

1561 AGC GGA AGC GAG TGG GTG TGT GGA ATG TAC CAT ACA TCT CCC AGG CCT ATG ACC CGG 1620

1621 GTG ATA CCC TGC GGA TGG AGC TGC CCA GAG GGA TGT GTC TGG GCA GTG ACA CAG ACC 1680

1681 CGG ACA TGG CCT TCT GTA AGA GCT TTC GAG ACA AGG CAT CTT CCT CAT CGA GCA ATC 1740

1741 AGC ATG AAT TTG CCC GGC TCC TGG CCA CTT CCA GAT ACG ACA CGG AGC ACC TGC ACC CG 1800

1801 ACC TCT GGC AGA TCT TCG ACA ACC CCG TCG ACT GGA AGG AGC AGT ACA TCC ACG AGA ACT 1860

1861 ACA GCC GGG CCC TGG AAG GGG AAG GAA TCG TGG AGC AGC CAT GCC GGG ACG TGT ACT GGT 1920

1921 TCC CAC TGC TGT CAG AAC AAA TGT GTG ATG AGC TGG TGG CAG AGA TGG AGC ACT ACG GCC 1980

1981 AGT GGT CAG GCG GCC GGC ATG AGG ATT CAA GGC TGG CTG GAG GCT ACG AGA ATG TGC CCA 2040
```

Fig. 8A

```
2041  CCG TGG ACA TCC ACA TGA AGC AGG TGG GGT ACG AGG ACC AGT GGC TGC AGC TGC TGC GGA   2100
2101  CGT ATG TGG GCC CCA TGA CCG AGA GCC TGT TTC CCG GTT ACC ACA CCA AGG CGC GGG CGG   2160
2161  TGA TGA ACT TTG TGG TTC GCT ACC GGC CAG ACG AGC AGC CGT CTC TGC GGC CAC ACC ACG   2220
2221  ACT CAT CCA CCT TCA CCC TCA ACG TTG CCC TCA ACC ACA AGG CCC TGG ACT ATG AGG GAG   2280
2281  GTG GCT GCC GCT TCC TGC GCT ACG ACT GTG TGA TCT CCT CCC CGA GGA AGG GCT GGG CAC   2340
2341  TCC TGC ACC CCG GCC GCC TCA CCC ACT ACC ACG AGG GGC TGC AAA CGA CCT GGG GCA CAC   2400
2401  GCT ACA TCA TGG TGT CCT TTG TCG ACC CCT GAC ACT CAA CCA CTC TGC CAA ACC           2455
```

Fig. 8B

```
289                                                         TCC GAC CGG CCC  300
 25                                                          S   D   R   P   28

301 CGG GGC CGA GAC CCG GTC AAC CCA GAG AAG CTG CTG GTG ATC ACT GTG GCC ACA GCT GAA  360
 29  R   G   R   D   P   V   N   P   E   K   L   L   V   I   T   V   A   T   A   E   48

361 ACC GAG GGG TAC CTG CGT TTC CTG CGC TCT GCG GAG TTC TTC AAC TAC ACT GTG CGG ACC  420
 49  T   E   G   Y   L   R   F   L   R   S   A   E   F   F   N   Y   T   V   R   T   68

421 CTG GGC CTG GGA GAG GAG TGG CGA GGG GGT GAT GTG GCT CGA ACA GTT GGT GGA GGA CAG  480
 69  L   G   L   G   E   E   W   R   G   G   D   V   A   R   T   V   G   G   G   Q   88

481 AAG GTC CGG TGG TTA AAG AAG GAA ATG GAG AAA TAC GCT GAC CGG GAG GAT ATG ATC ATC  540
 89  K   V   R   W   L   K   K   E   M   E   K   Y   A   D   R   E   D   M   I   I  108

541 ATG TTT GTG GAT AGC TAC GAC GTG ATT CTG GCC GGC AGC CCC ACA GAG CTG CTG AAG AAG  600
109  M   F   V   D   S   Y   D   V   I   L   A   G   S   P   T   E   L   L   K   K  128

601 TTC GTC CAG AGT GGC AGC CGC CTG CTC TTC TCT GCA GAG AGC TTC TGC TGG CCC GAG TGG  660
129  F   V   Q   S   G   S   R   L   L   F   S   A   E   S   F   C   W   P   E   W  148

661 GGG CTG GCG GAG CAG TAC CCT GAG GTG GGC ACG GGG AAG CGC TTC CTC AAT TCT GGT GGA  720
149  G   L   A   E   Q   Y   P   E   V   G   T   G   K   R   F   L   N   S   G   G  168

721 TTC ATC GGT TTT GCC ACC ACC ATC CAC CAA ATC GTG CGC CAG TGG AAG TAC AAG GAT GAT  780
169  F   I   G   F   A   T   T   I   H   Q   I   V   R   Q   W   K   Y   K   D   D  188

781 GAC GAC GAC CAG CTG TTC TAC ACA CGG CTC TAC CTG GAC CCA GGA CTG AGG GAG AAA CTC  840
189  D   D   D   Q   L   F   Y   T   R   L   Y   L   D   P   G   L   R   E   K   L  208

841 AGC CTT AAT CTG GAT CAT AAG TCT CGG ATC TTT CAG AAC CTC AAC GGG GCT TTA GAT GAA  900
209  S   L   N   L   D   H   K   S   R   I   F   Q   N   L   N   G   A   L   D   E  228

901 GTG GTT TTA AAG TTT GAT CGG AAC CGT GTG CGT ATC CGG AAC GTG GCC TAC GAC ACG CTC  960
229  V   V   L   K   F   D   R   N   R   V   R   I   R   N   V   A   Y   D   T   L  248

961 CCC ATT GTG GTC CAT GGA AAC GGT CCC ACT AAG CTG CAG CTC AAC TAC CTG GGA AAC TAC 1020
249  P   I   V   V   H   G   N   G   P   T   K   L   Q   L   N   Y   L   G   N   Y  268

1021 GTC CCC AAT GGC TGG ACT CCT GAG GGA GGC TGT GGC TTC TGC AAC CAG GAC CGG AGG ACA 1080
269  V   P   N   G   W   T   P   E   G   G   C   G   F   C   N   Q   D   R   R   T  288

1081 CTC CCG GGG GGG CAG CCT CCC CCC CGG GTG TTT CTG GCC GTG TTT GTG GAA CAG CCT ACT 1140
289  L   P   G   G   Q   P   P   P   R   V   F   L   A   V   F   V   E   Q   P   T  308

1141 CCG TTT CTG CCC CGC TTC CTG CAG CGG CTG CTA CTC CTG GAC TAT CCC CCC GAC AGG GTC 1200
309  P   F   L   P   R   F   L   Q   R   L   L   L   L   D   Y   P   P   D   R   V  328

1201 ACC CTT TTC CTG CAC AAC AAC GAG GTC TTC CAT GAA CCC CAC ATC GCT GAC TCC TGG CCG 1260
329  T   L   F   L   H   N   N   E   V   F   H   E   P   H   I   A   D   S   W   P  348

1261 CAG CTC CAG GAC CAC TTC TCA GCT GTG AAG CTC GTG GGG CCG GAG GAG GCT CTG AGC CCA 1320
349  Q   L   Q   D   H   F   S   A   V   K   L   V   G   P   E   E   A   L   S   P  368

1321 GGC GAG GCC AGG GAC ATG GCC ATG GAC CTG TGT CGG CAG GAC CCC GAG TGT GAG TTC TAC 1380
369  G   E   A   R   D   M   A   M   D   L   C   R   Q   D   P   E   C   E   F   Y  388

1381 TTC AGC CTG GAC GCC GAC GCT GTC CTC ACC AAC CTG CAG ACC CTG CGT ATC CTC ATT GAG 1440
389  F   S   L   D   A   D   A   V   L   T   N   L   Q   T   L   R   I   L   I   E  408

1441 GAG AAC AGG AAG GTG ATC GCC CCC ATG CTG TCC CGC CAC GGC AAG CTG TGG TCC AAC TTC 1500
409  E   N   R   K   V   I   A   P   M   L   S   R   H   G   K   L   W   S   N   F  428

1501 TGG GGC GCC CTG AGC CCC GAT GAG TAC TAC GCC CGC TCC GAG GAC TAC GTG GAG CTG GTG 1560
429  W   G   A   L   S   P   D   E   Y   Y   A   R   S   E   D   Y   V   E   L   V  448

1561 CAG CGG AAG CGA GTG GGT GTG TGG AAT GTA CCA TAC ATC TCC CAG GCC TAT GTG ATC CGG 1620
449  Q   R   K   R   V   G   V   W   N   V   P   Y   I   S   Q   A   Y   V   I   R  468

1621 GGT GAT ACC CTG CGG ATG GAG CTG CCC CAG AGG GAT GTG TTC TCG GGC AGT GAC ACA GAC 1680
469  G   D   T   L   R   M   E   L   P   Q   R   D   V   F   S   G   S   D   T   D  488

1681 CCG GAC ATG GCC TTC TGT AAG AGC TTT CGA GAC AAG GGC ATC TTC CTC CAT CTG AGC AAT 1740
489  P   D   M   A   F   C   K   S   F   R   D   K   G   I   F   L   H   L   S   N  508

1741 CAG CAT GAA TTT GGC CGG CTC CTG GCC ACT TCC AGA TAA GAC ACG GAG CAC CTG CAC CCC 1800
509  Q   H   E   F   G   R   L   L   A   T   S   R   *                              520
```

Fig. 9A

```
1801  GAC CTC TGG CAG ATC TTC GAC AAC CCC GTC GAC TGG AAG GAG CAG TAC ATC CAC GAG AAC  1860
1861  TAC AGC CGG GCC CTG GAA GGG GAA GGA ATC GTG GAG CAG CCA TGC CCG GAC GTG TAC TGG  1920
1921  TTC CCA CTG CTG TCA GAA CAA ATG TGT GAT GAG CTG GTG GCA GAG ATG GAG CAC TAC GGC  1980
1981  CAG TGG TCA GGC GGC CGG CAT GAG GAT TCA AGG CTG GCT GGA GGC TAC GAG AAT GTG CCC  2040
2041  ACC GTG GAC ATC CAC ATG AAG CAG GTG GGG TAC GAG GAC CAG TGG CTG CAG CTG CTG CGG  2100
2101  ACG TAT GTG GGC CCC ATG ACC GAG AGC CTG TTT CCC GGT TAC CAC ACC AAG GCG CGG GCG  2160
2161  GTG ATG AAC TTT GTG GTT CGC TAC CGG CCA GAC GAG CAG CCG TCT CTG CGG CCA CAC CAC  2220
2221  GAC TCA TCC ACC TTC ACC CTC AAC GTT GCC CTC AAC CAC AAG GGC CTG GAC TAT GAG GGA  2280
2281  GGT GGC TGC CGC TTC CTG CGC TAC GAC TGT GTG ATC TCC TCC CCG AGG AAG GGC TGG GCA  2340
2341  CTC CTG CAC CCC GGC CGC CTC ACC CAC TAC CAC GAG GGG CTG CCA ACG ACC TGG GGC ACA  2400
2401  CGC TAC ATC ATG GTG TCC TTT GTC GAC CCC TGA CAC TCA ACC ACT CTG CCA AAC C         2455
```

Fig. 9B

```
289                                                                TCC GAC CGG CCC  300
 25                                                                 S   D   R   P   28

301 CGG GGC CGA GAC CCG GTC AAC CCA GAG AAG CTG CTG GTG ATC ACT GTG GCC ACA GCT GAA  360
 29  R   G   R   D   P   V   N   P   E   K   L   L   V   I   T   V   A   T   A   E   48

361 ACC GAG GGG TAC CTG CGT TTC CTG CGC TCT GCG GAG TTC TTC AAC TAC ACT GTG CGG ACC  420
 49  T   E   G   Y   L   R   F   L   R   S   A   E   F   F   N   Y   T   V   R   T   68

421 CTG GGC CTG GGA GAG GAG TGG CGA GGG GGT GAT GTG GCT CGA ACA GTT GGT GGA GGA CAG  480
 69  L   G   L   G   E   E   W   R   G   G   D   V   A   R   T   V   G   G   G   Q   88

481 AAG GTC CGG TGG TTA AAG AAG GAA ATG GAG AAA TAC GCT GAC CGG GAG GAT ATG ATC ATC  540
 89  K   V   R   W   L   K   K   E   M   E   K   Y   A   D   R   E   D   M   I   I  108

541 ATG TTT GTG GAT AGC TAC GAC GTG ATT CTG GCC GGC AGC CCC ACA GAG CTG CTG AAG AAG  600
109  M   F   V   D   S   Y   D   V   I   L   A   G   S   P   T   E   L   L   K   K  128

601 TTC GTC CAG AGT GGC AGC CGC CTG CTC TTC TCT GCA GAG AGC TTC TGC TGG CCC GAG TGG  660
129  F   V   Q   S   G   S   R   L   L   F   S   A   E   S   F   C   W   P   E   W  148

661 GGG CTG GCG GAG CAG TAC CCT GAG GTG GGC ACG GGA AAG CGC TTC CTC AAT TCT GGT GGA  720
149  G   L   A   E   Q   Y   P   E   V   G   T   G   K   R   F   L   N   S   G   G  168

721 TTC ATC GGT TTT GCC ACC ACC ATC CAC CAA ATC GTG CGC CAG TGG AAG TAC AAG GAT GAT  780
169  F   I   G   F   A   T   T   I   H   Q   I   V   R   Q   W   K   Y   K   D   D  188

781 GAC GAC GAC CAG CTG TTC TAC ACA CGG CTC TAC CTG GAC CCA GGA CTG AGG GAG AAA CTC  840
189  D   D   D   Q   L   F   Y   T   R   L   Y   L   D   P   G   L   R   E   K   L  208

841 AGC CTT AAT CTG GAT CAT AAG TCT CGG ATC TTT CAG AAC CTC AAC GGG GCT TTA GAT GAA  900
209  S   L   N   L   D   H   K   S   R   I   F   Q   N   L   N   G   A   L   D   E  228

901 GTG GTT TTA AAG TTT GAT CGG AAC CGT GTG CGT ATC CGG AAC GTG GCC TAC GAC ACG CTC  960
229  V   V   L   K   F   D   R   N   R   V   R   I   R   N   V   A   Y   D   T   L  248

961 CCC ATT GTG GTC CAT GGA AAC GGT CCC ACT AAG CTG CAG CTC AAC TAC CTG GGA AAC TAC 1020
249  P   I   V   V   H   G   N   G   P   T   K   L   Q   L   N   Y   L   G   N   Y  268

1021 GTC CCC AAT GGC TGG ACT CCT GAG GGA GGC TGT GGC TTC TGC AAC CAG GAC CGG AGG ACA 1080
269   V   P   N   G   W   T   P   E   G   G   C   G   F   C   N   Q   D   R   R   T  288

1081 CTC CCG GGG GGG CAG CCT CCC CCC CGG GTG TTT CTG GCC GTG TTT GTG GAA CAG CCT ACT 1140
289   L   P   G   G   Q   P   P   P   R   V   F   L   A   V   F   V   E   Q   P   T  308

1141 CCG TTT CTG CCC CGC TTC CTG CAG CGG CTG CTA CTC CTG GAC TAT CCC CCC GAC AGG GTC 1200
309   P   F   L   P   R   F   L   Q   R   L   L   L   L   D   Y   P   P   D   R   V  328

1201 ACC CTT TTC CTG CAC AAC AAC GAG GTC TTC CAT GAA CCC CAC ATC GCT GAC TCC TGG CCG 1260
329   T   L   F   L   H   N   N   E   V   F   H   E   P   H   I   A   D   S   W   P  348

1261 CAG CTC CAG GAC CAC TTC TCA GCT GTG AAG CTC GTG GGG CCG GAG GAG GCT CTG AGC CCA 1320
349   Q   L   Q   D   H   F   S   A   V   K   L   V   G   P   E   E   A   L   S   P  368

1321 GGC GAG GCC AGG GAC ATG GCC ATG GAC CTG TGT CGG CAG GAC CCC GAG TGT GAG TTC TAC 1380
369   G   E   A   R   D   M   A   M   D   L   C   R   Q   D   P   E   C   E   F   Y  388

1381 TTC AGC CTG GAC GCC GAC GCT GTC CTC ACC AAC CTG CAG ACC CTG CGT ATC CTC ATT GAG 1440
389   F   S   L   D   A   D   A   V   L   T   N   L   Q   T   L   R   I   L   I   E  408

1441 GAG AAC AGG AAG GTG ATC GCC CCC ATG CTG TCC CGC CAC GGC AAG CTG TGG TCC AAC TTC 1500
409   E   N   R   K   V   I   A   P   M   L   S   R   H   G   K   L   W   S   N   F  428

1501 TGG GGC GCC CTG AGC CCC GAT GAG TAC TAC GCC CGC TCC GAG GAC TAC GTG GAG CTG GTG 1560
429   W   G   A   L   S   P   D   E   Y   Y   A   R   S   E   D   Y   V   E   L   V  448

1561 CAG CGG AAG CGA GTG GGT GTG TGG AAT GTA CCA TAC ATC TCC CAG GCC TAT GTG ATC CGG 1620
449   Q   R   K   R   V   G   V   W   N   V   P   Y   I   S   Q   A   Y   V   I   R  468

1621 GGT GAT ACC CTG CGG ATG GAG CTG CCC CAG AGG GAT GTG TTC TCG GGC AGT GAC ACA GAC 1680
469   G   D   T   L   R   M   E   L   P   Q   R   D   V   F   S   G   S   D   T   D  488

1681 CCG GAC ATG GCC TTC TGT AAG AGC TTT CGA GAC AAG GGC ATC TTC CTC CAT CTG AGC AAT 1740
489   P   D   M   A   F   C   K   S   F   R   D   K   G   I   F   L   H   L   S   N  508

1741 CAG CAT GAA TTT GGC CGG CTC CTG GCC ACT TCC AGA TAC GAC ACG GAG CAC CTG CAC CCC 1800
509   Q   H   E   F   G   R   L   L   A   T   S   R   Y   D   T   E   H   L   H   P  528
```

Fig. 10A

```
1801 GAC CTC TGG CAG ATC TTC GAC AAC CCC GTC GAC TGG AAG GAG CAG TAC ATC CAC GAG AAC 1860
 529  D   L   W   Q   I   F   D   N   P   V   D   W   K   E   Q   Y   I   H   E   N   548

1861 TAC AGC CGG GCC CTG GAA GGG GAA GGA ATC GTG GAG CAG CCA TGC CCG GAC GTG TAC TGG 1920
 549  Y   S   R   A   L   E   G   E   G   I   V   E   Q   P   C   P   D   V   Y   W   568

1921 TTC CCA CTG CTG TCA GAA CAA ATG TGT GAT GAG CTG GTG GCA GAG ATG GAG CAC TAC GGC 1980
 569  F   P   L   L   S   E   Q   M   C   D   E   L   V   A   E   M   E   H   Y   G   588

1981 CAG TGG TCA GGC GGC CGG CAT GAG GAT TCA AGG CTG GCT GGA GGC TAC GAG AAT GTG CCC 2040
 589  Q   W   S   G   G   R   H   E   D   S   R   L   A   G   G   Y   E   N   V   P   608

2041 ACC GTG GAC ATC CAC ATG AAG CAG GTG GGG TAC GAG GAC CAG TGG CTG CAG CTG CTG CGG 2100
 609  T   V   D   I   H   M   K   Q   V   G   Y   E   D   Q   W   L   Q   L   L   R   628

2101 ACG TAT GTG GGC CCC ATG ACC GAG AGC CTG TTT CCC GGT TAC CAC ACC AAG GCG CGG GCG 2160
 629  T   Y   V   G   P   M   T   E   S   L   F   P   G   Y   H   T   K   A   R   A   648

2161 GTG ATG AAC TTT GTG GTT CGC TAC CGG CCA GAC GAG CAG CCG TCT CTG CGG CCA CAC CAC 2220
 649  V   M   N   F   V   V   R   Y   R   P   D   E   Q   P   S   L   R   P   H   H   668

2221 GCC TCA TCC ACC TTC ACC CTC AAC GTT GCC CTC AAC CAC AAG GGC CTG GAC TAT GAG GGA 2280
 669  A   S   S   T   F   T   L   N   V   A   L   N   H   K   G   L   D   Y   E   G   688

2281 GGT GGC TGC CGC TTC CTG CGC TAC GAC TGT GTG ATC TCC TCC CCG AGG AAG GGC TGG GCA 2340
 689  G   G   C   R   F   L   R   Y   D   C   V   I   S   S   P   R   K   G   W   A   708

2341 CTC CTG CAC CCC GGC CGC CTC ACC CAC TAC CAC GAG GGG CTG CCA ACG ACC TGG GGC ACA 2400
 709  L   L   H   P   G   R   L   T   H   Y   H   E   G   L   P   T   T   W   G   T   728

2401 CGC TAC ATC ATG GTG TCC TTT GTC GAC CCC TGA CAC TCA ACC ACT CTG CCA AAC C        2455
 729  R   Y   I   M   V   S   F   V   D   P   *                                     738
```

Fig. 10B

|     |     |     |     |     |     |     |     |     |     |     |     |     |     |     |     |     |     |     |     |     |     | TCC | GAC | CGG | CCC |     | 300 |
|-----|-----|-----|-----|-----|-----|-----|-----|-----|-----|-----|-----|-----|-----|-----|-----|-----|-----|-----|-----|-----|-----|-----|-----|-----|-----|-----|-----|
|     |     |     |     |     |     |     |     |     |     |     |     |     |     |     |     |     |     |     |     |     |     |  S  |  D  |  R  |  P  |     |  28 |

```
301 CGG GGC CGA GAC CCG GTC AAC CCA GAG AAG CTG CTG GTG ATC ACT GTG GCC ACA GCT GAA   360
 29  R   G   R   D   P   V   N   P   E   K   L   L   V   I   T   V   A   T   A   E    48

361 ACC GAG GGG TAC CTG CGT TTC CTG CGC TCT GCG GAG TTC TTC AAC TAC ACT GTG CGG ACC   420
 49  T   E   G   Y   L   R   F   L   R   S   A   E   F   F   N   Y   T   V   R   T    68

421 CTG GGC CTG GGA GAG GAG TGG CGA GGG GGT GAT GTG GCT CGA ACA GTT GGT GGA GGA CAG   480
 69  L   G   L   G   E   E   W   R   G   G   D   V   A   R   T   V   G   G   G   Q    88

481 AAG GTC CGG TGG TTA AAG AAG GAA ATG GAG AAA TAC GCT GAC CGG GAG GAT ATG ATC ATC   540
 89  K   V   R   W   L   K   K   E   M   E   K   Y   A   D   R   E   D   M   I   I   108

541 ATG TTT GTG GAT AGC TAC GAC GTG ATT CTG GCC GGC AGC CCC ACA GAG CTG CTG AAG AAG   600
109  M   F   V   D   S   Y   D   V   I   L   A   G   S   P   T   E   L   L   K   K   128

601 TTC GTC CAG AGT GGC AGC CGC CTG CTC TTC TCT GCA GAG AGC TTC TGC TGG CCC GAG TGG   660
129  F   V   Q   S   G   S   R   L   L   F   S   A   E   S   F   C   W   P   E   W   148

661 GGG CTG GCG GAG CAG TAC CCT GAG GTG GGC ACG GGG AAG CGC TTC CTC AAT TCT GGT GGA   720
149  G   L   A   E   Q   Y   P   E   V   G   T   G   K   R   F   L   N   S   G   G   168

721 TTC ATC GGT TTT GCC ACC ACC ATC CAC CAA ATC GTG CGC CAG TGG AAG TAC AAG GAT GAT   780
169  F   I   G   F   A   T   T   I   H   Q   I   V   R   Q   W   K   Y   K   D   D   188

781 GAC GAC GAC CAG CTG TTC TAC ACA CGG CTC TAC CTG GAC CCA GGA CTG AGG GAG AAA CTC   840
189  D   D   D   Q   L   F   Y   T   R   L   Y   L   D   P   G   L   R   E   K   L   208

841 AGC CTT AAT CTG GAT CAT AAG TCT CGG ATC TTT CAG AAC CTC AAC GGG GCT TTA GAT GAA   900
209  S   L   N   L   D   H   K   S   R   I   F   Q   N   L   N   G   A   L   D   E   228

901 GTG GTT TTA AAG TTT GAT CGG AAC CGT GTG CGT ATC CGG AAC GTG GCC TAC GAC ACG CTC   960
229  V   V   L   K   F   D   R   N   R   V   R   I   R   N   V   A   Y   D   T   L   248

961 CCC ATT GTG GTC CAT GGA AAC GGT CCC ACT AAG CTG CAG CTC AAC TAC CTG GGA AAC TAC  1020
249  P   I   V   V   H   G   N   G   P   T   K   L   Q   L   N   Y   L   G   N   Y   268

1021 GTC CCC AAT GGC TGG ACT CCT GAG GGA GGC TGT GGC TTC TGC AAC CAG GAC CGG AGG ACA  1080
269  V   P   N   G   W   T   P   E   G   G   C   G   F   C   N   Q   D   R   R   T   288

1081 CTC CCG GGG GGG CAG CCT CCC CCC CGG GTG TTT CTG GCC GTG TTT GTG GAA CAG CCT ACT  1140
289  L   P   G   G   Q   P   P   P   R   V   F   L   A   V   F   V   E   Q   P   T   308

1141 CCG TTT CTG CCC CGC TTC CTG CAG CGG CTG CTA CTC CTG GAC TAT CCC CCC GAC AGG GTC  1200
309  P   F   L   P   R   F   L   Q   R   L   L   L   L   D   Y   P   P   D   R   V   328

1201 ACC CTT TTC CTG CAC AAC AAC GAG GTC TTC CAT GAA CCC CAC ATC GCT GAC TCC TGG CCG  1260
329  T   L   F   L   H   N   N   E   V   F   H   E   P   H   I   A   D   S   W   P   348

1261 CAG CTC CAG GAC CAC TTC TCA GCT GTG AAG CTC GTG GGG CCG GAG GAG GCT CTG AGC CCA  1320
349  Q   L   Q   D   H   F   S   A   V   K   L   V   G   P   E   E   A   L   S   P   368

1321 GGC GAG GCC AGG GAC ATG GCC ATG GAC CTG TGT CGG CAG GAC CCC GAG TGT GAG TTC TAC  1380
369  G   E   A   R   D   M   A   M   D   L   C   R   Q   D   P   E   C   E   F   Y   388

1381 TTC AGC CTG GAC GCC GAC GCT GTC CTC ACC AAC CTG CAG ACC CTG CGT ATC CTC ATT GAG  1440
389  F   S   L   D   A   D   A   V   L   T   N   L   Q   T   L   R   I   L   I   E   408

1441 GAG AAC AGG AAG GTG ATC GCC CCC ATG CTG TCC CGC CAC GGC AAG CTG TGG TCC AAC TTC  1500
409  E   N   R   K   V   I   A   P   M   L   S   R   H   G   K   L   W   S   N   F   428

1501 TGG GGC GCC CTG AGC CCC GAT GAG TAC TAC GCC CGC TCC GAG GAC TAC GTG GAG CTG GTG  1560
429  W   G   A   L   S   P   D   E   Y   Y   A   R   S   E   D   Y   V   E   L   V   448

1561 CAG CGG AAG CGA GTG GGT GTG TGG AAT GTA CCA TAC ATC TCC CAG GCC TAT GTG ATC CGG  1620
449  Q   R   K   R   V   G   V   W   N   V   P   Y   I   S   Q   A   Y   V   I   R   468

1621 GGT GAT ACC CTG CGG ATG GAG CTG CCC CAG AGG GAT GTG TTC TCG GGC AGT GAC ACA GAC  1680
469  G   D   T   L   R   M   E   L   P   Q   R   D   V   F   S   G   S   D   T   D   488

1681 CCG GAC ATG GCC TTC TGT AAG AGC TTT CGA GAC AAG GGC ATC TTC CTC CAT CTG AGC AAT  1740
489  P   D   M   A   F   C   K   S   F   R   D   K   G   I   F   L   H   L   S   N   508

1741 CAG CAT GAA TTT GGC CGG CTC CTG GCC ACT TCC AGA TAC GAC ACG GAG CAC CTG CAC CCC  1800
509  Q   H   E   F   G   R   L   L   A   T   S   R   Y   D   T   E   H   L   H   P   528
```

Fig. 11A

```
1801 GAC CTC TGG CAG ATC TTC GAC AAC CCC GTC GAC TGG AAG GAG CAG TAC ATC CAC GAG AAC 1860
 529  D   L   W   Q   I   F   D   N   P   V   D   W   K   E   Q   Y   I   H   E   N   548

1861 TAC AGC CGG GCC CTG GAA GGG GAA GGA ATC GTG GAG CAG CCA TGC CCG GAC GTG TAC TGG 1920
 549  Y   S   R   A   L   E   G   E   G   I   V   E   Q   P   C   P   D   V   Y   W   568

1921 TTC CCA CTG CTG TCA GAA CAA ATG TGT GAT GAG CTG GTG GCA GAG ATG GAG CAC TAC GGC 1980
 569  F   P   L   L   S   E   Q   M   C   D   E   L   V   A   E   M   E   H   Y   G   588

1981 CAG TGG TCA GGC GGC CGG CAT GAG GAT TCA AGG CTG GCT GGA GGC TAC GAG AAT GTG CCC 2040
 589  Q   W   S   G   G   R   H   E   D   S   R   L   A   G   G   Y   E   N   V   P   608

2041 ACC GTG GAC ATC CAC ATG AAG CAG GTG GGG TAC GAG GAC CAG TGG CTG CAG CTG CTG CGG 2100
 609  T   V   D   I   H   M   K   Q   V   G   Y   E   D   Q   W   L   Q   L   L   R   628

2101 ACG TAT GTG GGC CCC ATG ACC GAG AGC CTG TTT CCC GGT TAC CAC ACC AAG GCG CGG GCG 2160
 629  T   Y   V   G   P   M   T   E   S   L   F   P   G   Y   H   T   K   A   R   A   648

2161 GTG ATG AAC TTT GTG GTT CGC TAC CGG CCA GAC GAG CAG CCG TCT CTG CGG CCA CAC CAC 2220
 649  V   M   N   F   V   V   R   Y   R   P   D   E   Q   P   S   L   R   P   H   H   668

2221 GCT CAT CCA CCT TCA CCC TCA ACG TTG CCC TCA ACC ACA AGG GCC TGG ACT ATG AGG GAG 2280
 669  A   H   P   P   S   P   S   T   L   P   S   T   T   R   A   W   T   M   R   E   688

2281 GTG GCT GCC GCT TCC TGC GCT ACG ACT GTG TGA TCT CCT CCC CGA GGA AGG GCT GGG CAC 2340
 689  V   A   A   A   S   C   A   T   T   V   *                                       698

2341 TCC TGC ACC CCG GCC GCC TCA CCC ACT ACC ACG AGG GGC TGC AAC GAC CT GGG GCA CAC 2400

2401 GCT ACA TCA TGG TGT CCT TTG TCG ACC CCT GAC ACT CAA CCA CTC TGC AAA ACC 2455
```

Fig. 11B

SEQUENCE LISTING

<160> NUMBER OF SEQ ID NOS: 27

<210> SEQ ID NO 1
<211> LENGTH: 2592
<212> TYPE: DNA
<213> ORGANISM: mouse
<220> FEATURE:
<221> NAME/KEY: CDS
<222> LOCATION: (76)..(2301)

<400> SEQUENCE: 1

```
gcggccgcgt cgacatccag gcgctcagct cagcgccggt gcgggcctgg gtgtagccta      60
agcgtgctgc tagcc atg gct gcg gca ggc ccg gaa ccc cgg ctt ttg ctc     111
                 Met Ala Ala Ala Gly Pro Glu Pro Arg Leu Leu Leu
                  1               5                   10 ctg ctc ctg ctg ctg ctg ccg ccg ctg ccc ccc gta act tct gcc tcc     159
Leu Leu Leu Leu Leu Leu Pro Pro Leu Pro Pro Val Thr Ser Ala Ser
            15                  20                  25 gat cga ccc cgg ggc gcc aat gct gtc aac cca gac aaa ttg ctg gtg     207
Asp Arg Pro Arg Gly Ala Asn Ala Val Asn Pro Asp Lys Leu Leu Val
        30                  35                  40 atc act gtg gct acg gca gag aca gag ggg tac cgg cgt ttt ctg cag     255
Ile Thr Val Ala Thr Ala Glu Thr Glu Gly Tyr Arg Arg Phe Leu Gln
 45                  50                  55                  60 tct gcg gag ttc ttt aac tac act gta cgg acc ctg ggc ctg gga cag     303
Ser Ala Glu Phe Phe Asn Tyr Thr Val Arg Thr Leu Gly Leu Gly Gln
                 65                  70                  75 gag tgg cga ggg ggt gat gtg gct cga aca gtt ggt gga ggc cag aag     351
Glu Trp Arg Gly Gly Asp Val Ala Arg Thr Val Gly Gly Gly Gln Lys
             80                  85                  90 gtc agg tgg ctc aag aag gaa atg gag aaa tat gca gat cag aaa gac     399
Val Arg Trp Leu Lys Lys Glu Met Glu Lys Tyr Ala Asp Gln Lys Asp
         95                 100                 105 atg atc atc atg ttt gtg gac agc tac gac gtg att ctg gca agc agc     447
Met Ile Ile Met Phe Val Asp Ser Tyr Asp Val Ile Leu Ala Ser Ser
    110                 115                 120 ccg aca gag ctg ctg aag aag ttt gtt cag agt ggc agt cat ctg ctg     495
Pro Thr Glu Leu Leu Lys Lys Phe Val Gln Ser Gly Ser His Leu Leu
125                 130                 135                 140 ttc tct gct gag agc ttc tgc tgg cct gag tgg ggg ctg gca gag cag     543
Phe Ser Ala Glu Ser Phe Cys Trp Pro Glu Trp Gly Leu Ala Glu Gln
                145                 150                 155 tac cct gag gtg ggc atg ggg aag cgc ttc ctc aac tct ggt gga ttc     591
Tyr Pro Glu Val Gly Met Gly Lys Arg Phe Leu Asn Ser Gly Gly Phe
            160                 165                 170 atc ggc ttt gct ccc acc atc cat cag att gtc cgc cag tgg aac tac     639
```

```
                                        -continued

Ile Gly Phe Ala Pro Thr Ile His Gln Ile Val Arg Gln Trp Asn Tyr
        175                 180                 185 aaa gac gac gat gat gat caa ttg ttc tac act caa ctg tac ctg gac      687
Lys Asp Asp Asp Asp Asp Gln Leu Phe Tyr Thr Gln Leu Tyr Leu Asp
190                 195                 200 cca ggg ctg cgg gag aaa ctc aaa ctg agt ctg gac cat aaa tcc cgg      735
Pro Gly Leu Arg Glu Lys Leu Lys Leu Ser Leu Asp His Lys Ser Arg
205                 210                 215                 220 atc ttt cag aac ctc aat gga gcc tta gat gaa gtg atc tta aag ttt      783
Ile Phe Gln Asn Leu Asn Gly Ala Leu Asp Glu Val Ile Leu Lys Phe
                225                 230                 235 gac cag aat cgt gtg cgc atc cgg aat gtg gcc tac gac aca ctt cct      831
Asp Gln Asn Arg Val Arg Ile Arg Asn Val Ala Tyr Asp Thr Leu Pro
                240                 245                 250 gtt gtg gtc cat gga aat ggt ccc act aag ctc cag ctc aac tac ctg      879
Val Val Val His Gly Asn Gly Pro Thr Lys Leu Gln Leu Asn Tyr Leu
        255                 260                 265 ggg aac tat gtc ccc aat ggc tgg act ccc cag gga ggc tgt gga ttc      927
Gly Asn Tyr Val Pro Asn Gly Trp Thr Pro Gln Gly Gly Cys Gly Phe
        270                 275                 280 tgc aac cag acc ctg agg aca ctc ccg ggg ggg cag cct ccc ccc cgg      975
Cys Asn Gln Thr Leu Arg Thr Leu Pro Gly Gly Gln Pro Pro Pro Arg
285                 290                 295                 300 gtg ctt ctg gcc gtg ttt gtg gag cag cct act ccc ttc ctg cct cgg     1023
Val Leu Leu Ala Val Phe Val Glu Gln Pro Thr Pro Phe Leu Pro Arg
                305                 310                 315 ttc ctg cag cgc cta ctg ctc ctg gat tac ccc ccg gac agg atc tct     1071
Phe Leu Gln Arg Leu Leu Leu Leu Asp Tyr Pro Pro Asp Arg Ile Ser
                320                 325                 330 ctc ttc ctt cac aac agc gag gtg tac cac gag cct cat att gca gat     1119
Leu Phe Leu His Asn Ser Glu Val Tyr His Glu Pro His Ile Ala Asp
        335                 340                 345 gcc tgg cca cag ctc cag gac cat ttt tca gct gta aag ctg gtg ggg     1167
Ala Trp Pro Gln Leu Gln Asp His Phe Ser Ala Val Lys Leu Val Gly
        350                 355                 360 cca gag gag gcc ctg agc gca ggg gag gcc agg gac atg gcc atg gac     1215
Pro Glu Glu Ala Leu Ser Ala Gly Glu Ala Arg Asp Met Ala Met Asp
365                 370                 375                 380 agc tgt cgg cag aac cct gag tgt gag ttc tac ttt agc ctg gat gct     1263
Ser Cys Arg Gln Asn Pro Glu Cys Glu Phe Tyr Phe Ser Leu Asp Ala
                385                 390                 395 gat gcc gtc ctt acg aac ccg gag acc ttg cgt gtc ttg att gaa caa     1311
Asp Ala Val Leu Thr Asn Pro Glu Thr Leu Arg Val Leu Ile Glu Gln
                400                 405                 410 aac agg aag gta ata gct ccc atg ctt tcc cgc cat ggc aag ctc tgg     1359
Asn Arg Lys Val Ile Ala Pro Met Leu Ser Arg His Gly Lys Leu Trp
        415                 420                 425 tcc aac ttc tgg ggt gcc ctg agc ccc aat gag tac tac gcc cgc tcc     1407
Ser Asn Phe Trp Gly Ala Leu Ser Pro Asn Glu Tyr Tyr Ala Arg Ser
        430                 435                 440 gaa gac tac gtg gaa ctg gtg cag cgg aag cga gtg ggc gtg tgg aat     1455
Glu Asp Tyr Val Glu Leu Val Gln Arg Lys Arg Val Gly Val Trp Asn
445                 450                 455                 460 gta ccc tac ata tct cag gca tat gtg atc cgc ggg gag acc ctg agg     1503
Val Pro Tyr Ile Ser Gln Ala Tyr Val Ile Arg Gly Glu Thr Leu Arg
                465                 470                 475 act gaa ctg ccc caa aag gag gta ttc tcc agc agc gac aca gac cca     1551
Thr Glu Leu Pro Gln Lys Glu Val Phe Ser Ser Ser Asp Thr Asp Pro
                480                 485                 490
```

```
                                                           -continued
gat atg gct ttc tgc aag agc gtc cgg gac aag ggc atc ttc ctc cac         1599
Asp Met Ala Phe Cys Lys Ser Val Arg Asp Lys Gly Ile Phe Leu His
        495                 500                 505 ctc agc aac cag cac gag ttt ggc cgg ctg ctg gct act tct cgc tat         1647
Leu Ser Asn Gln His Glu Phe Gly Arg Leu Leu Ala Thr Ser Arg Tyr
    510                 515                 520 gac aca gac cac cta cac cca gac ctc tgg cag atc ttt gac aac cct         1695
Asp Thr Asp His Leu His Pro Asp Leu Trp Gln Ile Phe Asp Asn Pro
525                 530                 535                 540 gtg gac tgg aga gaa cag tac att cac gag aat tac agc cgg gcc ctg         1743
Val Asp Trp Arg Glu Gln Tyr Ile His Glu Asn Tyr Ser Arg Ala Leu
            545                 550                 555 gat ggg gaa ggg cta gtg gaa cag cca tgc cca gat gtg tac tgg ttc         1791
Asp Gly Glu Gly Leu Val Glu Gln Pro Cys Pro Asp Val Tyr Trp Phe
        560                 565                 570 cca ctg ctg acc gag cag atg tgt gat gag ctg gtg gag gaa atg gaa         1839
Pro Leu Leu Thr Glu Gln Met Cys Asp Glu Leu Val Glu Glu Met Glu
    575                 580                 585 cac tat ggc cag tgg tct gga ggc cgg cac gag gat tcc agg ttg gct         1887
His Tyr Gly Gln Trp Ser Gly Gly Arg His Glu Asp Ser Arg Leu Ala
590                 595                 600 gga gga tac gag aat gtt ccc acc gtt gat atc cac atg aaa cag gtg         1935
Gly Gly Tyr Glu Asn Val Pro Thr Val Asp Ile His Met Lys Gln Val
605                 610                 615                 620 gga tac gag gac cag tgg ctt cag ctg ctg cgg aca tat gtg ggg ccc         1983
Gly Tyr Glu Asp Gln Trp Leu Gln Leu Leu Arg Thr Tyr Val Gly Pro
            625                 630                 635 atg acg gag tac ctg ttc cct ggc tac cac acc aag aca cgg gca gtg         2031
Met Thr Glu Tyr Leu Phe Pro Gly Tyr His Thr Lys Thr Arg Ala Val
        640                 645                 650 atg aac ttc gtg gtc cgc tac cgg cca gat gag cag ccc tcg ctt cgg         2079
Met Asn Phe Val Val Arg Tyr Arg Pro Asp Glu Gln Pro Ser Leu Arg
    655                 660                 665 cca cac cat gac tcg tcc acc ttc act ctc aat gtc gcc ctc aac cac         2127
Pro His His Asp Ser Ser Thr Phe Thr Leu Asn Val Ala Leu Asn His
670                 675                 680 aag ggt gta gat tat gag gga ggc ggc tgc cgc ttc ctg cgt tac gac         2175
Lys Gly Val Asp Tyr Glu Gly Gly Gly Cys Arg Phe Leu Arg Tyr Asp
685                 690                 695                 700 tgc aga atc tcc tct ccg agg aaa ggc tgg gcc ctc ctg cac cct ggc         2223
Cys Arg Ile Ser Ser Pro Arg Lys Gly Trp Ala Leu Leu His Pro Gly
            705                 710                 715 cgc ctc aca cac tac cat gag ggg ctg ccc acc acc cgg ggt act cga         2271
Arg Leu Thr His Tyr His Glu Gly Leu Pro Thr Thr Arg Gly Thr Arg
        720                 725                 730 tac atc atg gtg tcc ttt gtt gac ccc tga cactcaacca gtctgccaaa          2321
Tyr Ile Met Val Ser Phe Val Asp Pro
        735                 740 ccttctctgc cactgtgcct tgttggacaa cctgggtcgc cattctcaga gagagggac       2381 gctgcccgtc tcatctcccg agagtgtctg tgtgcctggg atggaatgtg ctggtcccaa      2441
cagtcctcag gaggtccctg gagtcttcca cttgcccact gacccatgg actcaggaa        2501 agtggacttc tgagggtccc ctgcctgata aattattaag cttcctcagc ctcactttca      2561 ataaaggat gtttgtaaaa aaaaaaaaa a                                       2592

<210> SEQ ID NO 2
<211> LENGTH: 741
<212> TYPE: PRT
<213> ORGANISM: mouse
```

<400> SEQUENCE: 2

```
Met Ala Ala Gly Pro Glu Pro Arg Leu Leu Leu Leu Leu Leu Leu
 1               5                  10                  15

Leu Leu Pro Pro Leu Pro Val Thr Ser Ala Ser Asp Arg Pro Arg
             20                  25                  30

Gly Ala Asn Ala Val Asn Pro Asp Lys Leu Leu Val Ile Thr Val Ala
             35                  40                  45

Thr Ala Glu Thr Glu Gly Tyr Arg Arg Phe Leu Gln Ser Ala Glu Phe
 50                  55                  60

Phe Asn Tyr Thr Val Arg Thr Leu Gly Leu Gly Gln Glu Trp Arg Gly
 65                  70                  75                  80

Gly Asp Val Ala Arg Thr Val Gly Gly Gln Lys Val Arg Trp Leu
                 85                  90                  95

Lys Lys Glu Met Glu Lys Tyr Ala Asp Gln Lys Asp Met Ile Ile Met
             100                 105                 110

Phe Val Asp Ser Tyr Asp Val Ile Leu Ala Ser Ser Pro Thr Glu Leu
             115                 120                 125

Leu Lys Lys Phe Val Gln Ser Gly Ser His Leu Leu Phe Ser Ala Glu
     130                 135                 140

Ser Phe Cys Trp Pro Glu Trp Gly Leu Ala Glu Gln Tyr Pro Glu Val
145                 150                 155                 160

Gly Met Gly Lys Arg Phe Leu Asn Ser Gly Gly Phe Ile Gly Phe Ala
                 165                 170                 175

Pro Thr Ile His Gln Ile Val Arg Gln Trp Asn Tyr Lys Asp Asp Asp
             180                 185                 190

Asp Asp Gln Leu Phe Tyr Thr Gln Leu Tyr Leu Asp Pro Gly Leu Arg
         195                 200                 205

Glu Lys Leu Lys Leu Ser Leu Asp His Lys Ser Arg Ile Phe Gln Asn
     210                 215                 220

Leu Asn Gly Ala Leu Asp Glu Val Ile Leu Lys Phe Asp Gln Asn Arg
225                 230                 235                 240

Val Arg Ile Arg Asn Val Ala Tyr Asp Thr Leu Pro Val Val Val His
                 245                 250                 255

Gly Asn Gly Pro Thr Lys Leu Gln Leu Asn Tyr Leu Gly Asn Tyr Val
             260                 265                 270

Pro Asn Gly Trp Thr Pro Gln Gly Gly Cys Gly Phe Cys Asn Gln Thr
         275                 280                 285

Leu Arg Thr Leu Pro Gly Gly Gln Pro Pro Arg Val Leu Leu Ala
     290                 295                 300

Val Phe Val Glu Gln Pro Thr Pro Phe Leu Pro Arg Phe Leu Gln Arg
305                 310                 315                 320

Leu Leu Leu Leu Asp Tyr Pro Pro Asp Arg Ile Ser Leu Phe Leu His
                 325                 330                 335

Asn Ser Glu Val Tyr His Glu Pro His Ile Ala Asp Ala Trp Pro Gln
             340                 345                 350

Leu Gln Asp His Phe Ser Ala Val Lys Leu Val Gly Pro Glu Glu Ala
         355                 360                 365

Leu Ser Ala Gly Glu Ala Arg Asp Met Ala Met Asp Ser Cys Arg Gln
     370                 375                 380

Asn Pro Glu Cys Glu Phe Tyr Phe Ser Leu Asp Ala Asp Ala Val Leu
385                 390                 395                 400

Thr Asn Pro Glu Thr Leu Arg Val Leu Ile Glu Gln Asn Arg Lys Val
```

-continued

```
                    405                 410                 415
Ile Ala Pro Met Leu Ser Arg His Gly Lys Leu Trp Ser Asn Phe Trp
            420                 425                 430
Gly Ala Leu Ser Pro Asn Glu Tyr Tyr Ala Arg Ser Glu Asp Tyr Val
        435                 440                 445
Glu Leu Val Gln Arg Lys Arg Val Gly Val Trp Asn Val Pro Tyr Ile
    450                 455                 460
Ser Gln Ala Tyr Val Ile Arg Gly Glu Thr Leu Arg Thr Glu Leu Pro
465                 470                 475                 480
Gln Lys Glu Val Phe Ser Ser Asp Thr Asp Pro Asp Met Ala Phe
            485                 490                 495
Cys Lys Ser Val Arg Asp Lys Gly Ile Phe Leu His Leu Ser Asn Gln
        500                 505                 510
His Glu Phe Gly Arg Leu Leu Ala Thr Ser Arg Tyr Asp Thr Asp His
    515                 520                 525
Leu His Pro Asp Leu Trp Gln Ile Phe Asp Asn Pro Val Asp Trp Arg
530                 535                 540
Glu Gln Tyr Ile His Glu Asn Tyr Ser Arg Ala Leu Asp Gly Glu Gly
545                 550                 555                 560
Leu Val Glu Gln Pro Cys Pro Asp Val Tyr Trp Phe Pro Leu Leu Thr
            565                 570                 575
Glu Gln Met Cys Asp Glu Leu Val Glu Glu Met Glu His Tyr Gly Gln
        580                 585                 590
Trp Ser Gly Gly Arg His Glu Asp Ser Arg Leu Ala Gly Gly Tyr Glu
    595                 600                 605
Asn Val Pro Thr Val Asp Ile His Met Lys Gln Val Gly Tyr Glu Asp
    610                 615                 620
Gln Trp Leu Gln Leu Leu Arg Thr Tyr Val Gly Pro Met Thr Glu Tyr
625                 630                 635                 640
Leu Phe Pro Gly Tyr His Thr Lys Thr Arg Ala Val Met Asn Phe Val
            645                 650                 655
Val Arg Tyr Arg Pro Asp Glu Gln Pro Ser Leu Arg Pro His His Asp
        660                 665                 670
Ser Ser Thr Phe Thr Leu Asn Val Ala Leu Asn His Lys Gly Val Asp
    675                 680                 685
Tyr Glu Gly Gly Gly Cys Arg Phe Leu Arg Tyr Asp Cys Arg Ile Ser
    690                 695                 700
Ser Pro Arg Lys Gly Trp Ala Leu Leu His Pro Gly Arg Leu Thr His
705                 710                 715                 720
Tyr His Glu Gly Leu Pro Thr Thr Arg Gly Thr Arg Tyr Ile Met Val
            725                 730                 735
Ser Phe Val Asp Pro
            740

<210> SEQ ID NO 3
<211> LENGTH: 2193
<212> TYPE: DNA
<213> ORGANISM: Caenorhabditis elegans
<220> FEATURE:
<221> NAME/KEY: CDS
<222> LOCATION: (1)..(2193)

<400> SEQUENCE: 3 atg agg gtt ctc cct ttt cta cta cca cta ata ccc gtt ctc ctg gca      48
Met Arg Val Leu Pro Phe Leu Leu Pro Leu Ile Pro Val Leu Leu Ala
  1               5                  10                  15
```

-continued

| | |
|---|---|
| acc aca ata acc gat tta ccc gaa ctg gtt gta gtc aca gtt gca act<br>Thr Thr Ile Thr Asp Leu Pro Glu Leu Val Val Val Thr Val Ala Thr<br>            20                   25                  30 | 96 |
| gaa aat aca gat ggg ctt aaa cgt ctt cta gaa tct gca aaa gca ttc<br>Glu Asn Thr Asp Gly Leu Lys Arg Leu Leu Glu Ser Ala Lys Ala Phe<br>        35                   40                   45 | 144 |
| gac atc aat att gaa gtt ctt gga ttg ggc gag aag tgg aat ggt ggt<br>Asp Ile Asn Ile Glu Val Leu Gly Leu Gly Glu Lys Trp Asn Gly Gly<br>50                   55                   60 | 192 |
| gac aca aga atc gaa caa ggt gga ggc caa aaa att cga att ctt tcc<br>Asp Thr Arg Ile Glu Gln Gly Gly Gly Gln Lys Ile Arg Ile Leu Ser<br>65                   70                   75                   80 | 240 |
| gat tgg att gaa aaa tac aaa gac gct tcg gat aca atg atc atg ttt<br>Asp Trp Ile Glu Lys Tyr Lys Asp Ala Ser Asp Thr Met Ile Met Phe<br>            85                   90                   95 | 288 |
| gtg gat gct tat gat gtt gta ttc aat gct gat tct aca aca atc ctc<br>Val Asp Ala Tyr Asp Val Val Phe Asn Ala Asp Ser Thr Thr Ile Leu<br>            100                 105               110 | 336 |
| agg aag ttt ttc gaa cat tac tct gaa aag cgt ctt cta ttc gga gct<br>Arg Lys Phe Phe Glu His Tyr Ser Glu Lys Arg Leu Leu Phe Gly Ala<br>         115                 120               125 | 384 |
| gag cca ttc tgc tgg cca gat cag agt ttg gca cca gaa tat cct att<br>Glu Pro Phe Cys Trp Pro Asp Gln Ser Leu Ala Pro Glu Tyr Pro Ile<br>130                   135               140 | 432 |
| gtt gag ttc ggg aaa cga ttc ttg aat tct ggc ctc ttc atg ggt tac<br>Val Glu Phe Gly Lys Arg Phe Leu Asn Ser Gly Leu Phe Met Gly Tyr<br>145                   150               155               160 | 480 |
| ggt ccg gaa atg cac aaa att ctg aag ttg aag tcc gtt gag gat aag<br>Gly Pro Glu Met His Lys Ile Leu Lys Leu Lys Ser Val Glu Asp Lys<br>         165                 170               175 | 528 |
| gat gat gac cag ttg tac tac aca atg att tat ctt gat gag aag ttg<br>Asp Asp Asp Gln Leu Tyr Tyr Thr Met Ile Tyr Leu Asp Glu Lys Leu<br>            180                 185               190 | 576 |
| aga aaa gaa ttg aat atg gat ctt gat tca atg tcc aag atc ttc caa<br>Arg Lys Glu Leu Asn Met Asp Leu Asp Ser Met Ser Lys Ile Phe Gln<br>         195                 200               205 | 624 |
| aac ttg aat gga gtt att gaa gat gtt gaa ctt caa ttc aaa gaa gat<br>Asn Leu Asn Gly Val Ile Glu Asp Val Glu Leu Gln Phe Lys Glu Asp<br>210                   215               220 | 672 |
| gga act cca gaa gca tat aat gca gct tat aac acc aaa cca ttg att<br>Gly Thr Pro Glu Ala Tyr Asn Ala Ala Tyr Asn Thr Lys Pro Leu Ile<br>225                   230               235               240 | 720 |
| gtt cat ggt aac ggt cct agc aaa tcc cat ttg aac tac ctt gga aat<br>Val His Gly Asn Gly Pro Ser Lys Ser His Leu Asn Tyr Leu Gly Asn<br>         245                 250               255 | 768 |
| tat ctc gga aac cgt tgg aat tca caa ctc gga tgt aga act tgt ggg<br>Tyr Leu Gly Asn Arg Trp Asn Ser Gln Leu Gly Cys Arg Thr Cys Gly<br>         260                 265               270 | 816 |
| ctt gaa gtg aaa gaa tct gaa gaa gtg cca ctg att gca ttg aac ctt<br>Leu Glu Val Lys Glu Ser Glu Glu Val Pro Leu Ile Ala Leu Asn Leu<br>         275                 280               285 | 864 |
| ttc att tcg aaa cct att cca ttc att gaa gaa gtt cta caa aaa atc<br>Phe Ile Ser Lys Pro Ile Pro Phe Ile Glu Glu Val Leu Gln Lys Ile<br>290                   295               300 | 912 |
| gct gag ttt gac tat ccg aaa gag aaa att gca ttg tat atc tac aat<br>Ala Glu Phe Asp Tyr Pro Lys Glu Lys Ile Ala Leu Tyr Ile Tyr Asn<br>305                   310               315               320 | 960 |
| aat cag cca ttt tca att aag aac att caa gac ttt ttg caa aaa cat<br>Asn Gln Pro Phe Ser Ile Lys Asn Ile Gln Asp Phe Leu Gln Lys His | 1008 |

-continued

```
              325                 330                 335
ggg aag tca tat tat aca aag agg gtt atc aat gga gtc aca gag att    1056
Gly Lys Ser Tyr Tyr Thr Lys Arg Val Ile Asn Gly Val Thr Glu Ile
            340                 345                 350 gga gac aga gaa gct agg aat gaa gca ata gaa tgg aat aaa gca cga    1104
Gly Asp Arg Glu Ala Arg Asn Glu Ala Ile Glu Trp Asn Lys Ala Arg
        355                 360                 365 aac gta gaa ttc gcc ttc ctc atg gac gga gat gcc tat ttc tcc gaa    1152
Asn Val Glu Phe Ala Phe Leu Met Asp Gly Asp Ala Tyr Phe Ser Glu
    370                 375                 380 ccc aaa gta atc aag gat ctg att caa tac tcc aag acc tac gat gtt    1200
Pro Lys Val Ile Lys Asp Leu Ile Gln Tyr Ser Lys Thr Tyr Asp Val
385                 390                 395                 400 gga ata att gct cca atg att ggt caa cct gga aaa ctc ttc acc aac    1248
Gly Ile Ile Ala Pro Met Ile Gly Gln Pro Gly Lys Leu Phe Thr Asn
                405                 410                 415 ttc tgg ggt gca att gct gca aat gga tac tac gct aga agt gaa gat    1296
Phe Trp Gly Ala Ile Ala Ala Asn Gly Tyr Tyr Ala Arg Ser Glu Asp
            420                 425                 430 tat atg gca att gtc aaa gga aat aga gtt gga tat tgg aat gtt cca    1344
Tyr Met Ala Ile Val Lys Gly Asn Arg Val Gly Tyr Trp Asn Val Pro
        435                 440                 445 ttc atc aca tca gct gtt cta ttt aac aag gaa aag ctt gaa gcc atg    1392
Phe Ile Thr Ser Ala Val Leu Phe Asn Lys Glu Lys Leu Glu Ala Met
    450                 455                 460 aaa gac gca tat agt tat aac aaa aac ttg gat cca gac atg tca atg    1440
Lys Asp Ala Tyr Ser Tyr Asn Lys Asn Leu Asp Pro Asp Met Ser Met
465                 470                 475                 480 tgc aag ttt gca agg gac aat gga cat ttc ttg tat atc gac aat gaa    1488
Cys Lys Phe Ala Arg Asp Asn Gly His Phe Leu Tyr Ile Asp Asn Glu
                485                 490                 495 aaa tat tat ggt ttt ttg att gtt agt gat gag tat gct gaa act gta    1536
Lys Tyr Tyr Gly Phe Leu Ile Val Ser Asp Glu Tyr Ala Glu Thr Val
            500                 505                 510 aca gaa gga aaa tgg cat ccc gaa atg tgg cag att ttt gag aat cga    1584
Thr Glu Gly Lys Trp His Pro Glu Met Trp Gln Ile Phe Glu Asn Arg
        515                 520                 525 gag ctt tgg gag gct cgt tac atc cat cca ggc tac cat aaa atc atg    1632
Glu Leu Trp Glu Ala Arg Tyr Ile His Pro Gly Tyr His Lys Ile Met
    530                 535                 540 gaa cct gaa cat gta gta gat caa gcc tgt cca gat gtc tac gat ttc    1680
Glu Pro Glu His Val Val Asp Gln Ala Cys Pro Asp Val Tyr Asp Phe
545                 550                 555                 560 cca ctg atg tct gag aga ttc tgt gaa gag ctt att gaa gaa atg gaa    1728
Pro Leu Met Ser Glu Arg Phe Cys Glu Glu Leu Ile Glu Glu Met Glu
                565                 570                 575 gga ttt gga cga tgg agt gat gga agt aac aac gac aaa cgt ctt gcg    1776
Gly Phe Gly Arg Trp Ser Asp Gly Ser Asn Asn Asp Lys Arg Leu Ala
            580                 585                 590 ggt gga tat gag aat gta cca act cga gat att cat atg aat caa gtt    1824
Gly Gly Tyr Glu Asn Val Pro Thr Arg Asp Ile His Met Asn Gln Val
        595                 600                 605 ggt ttt gag aga caa tgg ttg tac ttt atg gac acg tat gtt cgt cca    1872
Gly Phe Glu Arg Gln Trp Leu Tyr Phe Met Asp Thr Tyr Val Arg Pro
    610                 615                 620 gta caa gag aag act ttc ata gga tat tat cat cag cca gtt gag tcc    1920
Val Gln Glu Lys Thr Phe Ile Gly Tyr Tyr His Gln Pro Val Glu Ser
625                 630                 635                 640 aat atg atg ttc gtt gtt cgt tac aaa cct gaa gag caa cca tcg ctc    1968
```

```
                                    -continued
Asn Met Met Phe Val Val Arg Tyr Lys Pro Glu Glu Gln Pro Ser Leu
            645                 650                 655 cgc cca cat cat gat gca agc act ttc agt att gat att gca ctg aac    2016
Arg Pro His His Asp Ala Ser Thr Phe Ser Ile Asp Ile Ala Leu Asn
            660                 665                 670 aag aag gga aga gac tat gaa ggt gga ggt gta cga tat atc aga tat    2064
Lys Lys Gly Arg Asp Tyr Glu Gly Gly Gly Val Arg Tyr Ile Arg Tyr
            675                 680                 685 aat tgc acg gtg cca gca gat gaa gtt ggc tat gca atg atg ttc ccc    2112
Asn Cys Thr Val Pro Ala Asp Glu Val Gly Tyr Ala Met Met Phe Pro
690                 695                 700 gga aga ttg aca cat ctt cat gag ggt ctt gcc acc aca aag ggt acc    2160
Gly Arg Leu Thr His Leu His Glu Gly Leu Ala Thr Thr Lys Gly Thr
705             710                 715                 720 aga tat atc atg gta tcc ttt att aac cca taa                        2193
Arg Tyr Ile Met Val Ser Phe Ile Asn Pro
                725                 730

<210> SEQ ID NO 4
<211> LENGTH: 730
<212> TYPE: PRT
<213> ORGANISM: Caenorhabditis elegans

<400> SEQUENCE: 4

Met Arg Val Leu Pro Phe Leu Leu Pro Leu Ile Pro Val Leu Leu Ala
1               5                   10                  15

Thr Thr Ile Thr Asp Leu Pro Glu Leu Val Val Thr Val Ala Thr
                20                  25                  30

Glu Asn Thr Asp Gly Leu Lys Arg Leu Leu Glu Ser Ala Lys Ala Phe
            35                  40                  45

Asp Ile Asn Ile Glu Val Leu Gly Leu Gly Glu Lys Trp Asn Gly Gly
        50                  55                  60

Asp Thr Arg Ile Glu Gln Gly Gly Gly Gln Lys Ile Arg Ile Leu Ser
65                  70                  75                  80

Asp Trp Ile Glu Lys Tyr Lys Asp Ala Ser Asp Thr Met Ile Met Phe
                85                  90                  95

Val Asp Ala Tyr Asp Val Val Phe Asn Ala Asp Ser Thr Thr Ile Leu
            100                 105                 110

Arg Lys Phe Phe Glu His Tyr Ser Glu Lys Arg Leu Leu Phe Gly Ala
        115                 120                 125

Glu Pro Phe Cys Trp Pro Asp Gln Ser Leu Ala Pro Glu Tyr Pro Ile
130                 135                 140

Val Glu Phe Gly Lys Arg Phe Leu Asn Ser Gly Leu Phe Met Gly Tyr
145                 150                 155                 160

Gly Pro Glu Met His Lys Ile Leu Lys Leu Lys Ser Val Glu Asp Lys
                165                 170                 175

Asp Asp Asp Gln Leu Tyr Tyr Thr Met Ile Tyr Leu Asp Glu Lys Leu
            180                 185                 190

Arg Lys Glu Leu Asn Met Asp Leu Asp Ser Met Ser Lys Ile Phe Gln
        195                 200                 205

Asn Leu Asn Gly Val Ile Glu Asp Val Glu Leu Gln Phe Lys Glu Asp
    210                 215                 220

Gly Thr Pro Glu Ala Tyr Asn Ala Ala Tyr Asn Thr Lys Pro Leu Ile
225                 230                 235                 240

Val His Gly Asn Gly Pro Ser Lys Ser His Leu Asn Tyr Leu Gly Asn
                245                 250                 255
```

-continued

```
Tyr Leu Gly Asn Arg Trp Asn Ser Gln Leu Gly Cys Arg Thr Cys Gly
            260                 265                 270

Leu Glu Val Lys Glu Ser Glu Val Pro Leu Ile Ala Leu Asn Leu
        275                 280                 285

Phe Ile Ser Lys Pro Ile Pro Phe Ile Glu Glu Val Leu Gln Lys Ile
    290                 295                 300

Ala Glu Phe Asp Tyr Pro Lys Glu Lys Ile Ala Leu Tyr Ile Tyr Asn
305                 310                 315                 320

Asn Gln Pro Phe Ser Ile Lys Asn Ile Gln Asp Phe Leu Gln Lys His
                325                 330                 335

Gly Lys Ser Tyr Tyr Thr Lys Arg Val Ile Asn Gly Val Thr Glu Ile
            340                 345                 350

Gly Asp Arg Glu Ala Arg Asn Glu Ala Ile Glu Trp Asn Lys Ala Arg
        355                 360                 365

Asn Val Glu Phe Ala Phe Leu Met Asp Gly Asp Ala Tyr Phe Ser Glu
    370                 375                 380

Pro Lys Val Ile Lys Asp Leu Ile Gln Tyr Ser Lys Thr Tyr Asp Val
385                 390                 395                 400

Gly Ile Ile Ala Pro Met Ile Gly Gln Pro Gly Lys Leu Phe Thr Asn
                405                 410                 415

Phe Trp Gly Ala Ile Ala Ala Asn Gly Tyr Tyr Ala Arg Ser Glu Asp
            420                 425                 430

Tyr Met Ala Ile Val Lys Gly Asn Arg Val Gly Tyr Trp Asn Val Pro
        435                 440                 445

Phe Ile Thr Ser Ala Val Leu Phe Asn Lys Glu Lys Leu Glu Ala Met
    450                 455                 460

Lys Asp Ala Tyr Ser Tyr Asn Lys Asn Leu Asp Pro Asp Met Ser Met
465                 470                 475                 480

Cys Lys Phe Ala Arg Asp Asn Gly His Phe Leu Tyr Ile Asp Asn Glu
                485                 490                 495

Lys Tyr Tyr Gly Phe Leu Ile Val Ser Asp Glu Tyr Ala Glu Thr Val
            500                 505                 510

Thr Glu Gly Lys Trp His Pro Glu Met Trp Gln Ile Phe Glu Asn Arg
        515                 520                 525

Glu Leu Trp Glu Ala Arg Tyr Ile His Pro Gly Tyr His Lys Ile Met
    530                 535                 540

Glu Pro Glu His Val Val Asp Gln Ala Cys Pro Asp Val Tyr Asp Phe
545                 550                 555                 560

Pro Leu Met Ser Glu Arg Phe Cys Glu Glu Leu Ile Glu Glu Met Glu
                565                 570                 575

Gly Phe Gly Arg Trp Ser Asp Gly Ser Asn Asn Asp Lys Arg Leu Ala
            580                 585                 590

Gly Gly Tyr Glu Asn Val Pro Thr Arg Asp Ile His Met Asn Gln Val
        595                 600                 605

Gly Phe Glu Arg Gln Trp Leu Tyr Phe Met Asp Thr Tyr Val Arg Pro
    610                 615                 620

Val Gln Glu Lys Thr Phe Ile Gly Tyr Tyr His Gln Pro Val Glu Ser
625                 630                 635                 640

Asn Met Met Phe Val Val Arg Tyr Lys Pro Glu Glu Gln Pro Ser Leu
                645                 650                 655

Arg Pro His His Asp Ala Ser Thr Phe Ser Ile Asp Ile Ala Leu Asn
            660                 665                 670

Lys Lys Gly Arg Asp Tyr Glu Gly Gly Gly Val Arg Tyr Ile Arg Tyr
```

```
              675                 680                 685
Asn Cys Thr Val Pro Ala Asp Glu Val Gly Tyr Ala Met Met Phe Pro
    690                 695                 700

Gly Arg Leu Thr His Leu His Glu Gly Leu Ala Thr Thr Lys Gly Thr
705                 710                 715                 720

Arg Tyr Ile Met Val Ser Phe Ile Asn Pro
                725                 730

<210> SEQ ID NO 5
<211> LENGTH: 2234
<212> TYPE: DNA
<213> ORGANISM: Homo sapiens

<400> SEQUENCE: 5
accatgacct cctcggggcc tggaccccgg ttcctgctgc tgctgccgct gctgctgccc     60
cctgcggcct cagcctccga ccggcccggg ggccgagacc cggtcaaccc agagaagctg    120
ctggtgatca ctgtggccac agctgaaacc gaggggtacc tgcgtttcct gcgctctgcg    180
gagttcttca actacactgt gcggaccctg ggcctgggag aggagtggcg aggggggtgat   240 gtggctcgaa cagttggtgg aggacagaag gtccggtggt taaagaagga aatggagaaa    300
tacgctgacc gggaggatat gatcatcatg tttgtggata gctacgacgt gattctggcc    360
ggcagcccca cagagctgct gaagaagttc gtccagagtg cagccgcct gctcttctct     420 gcagagagct tctgctggcc cgagtggggg ctggcggagc agtaccctga ggtgggcacg    480
gggaagcgct cctcaattc tggtggattc atcggttttg ccaccaccat ccaccaaatc     540
gtgcgccagt ggaagtacaa ggatgatgac gacgaccagc tgttctacac acggctctac    600
ctggacccag gactgaggga gaaactcagc cttaatctgg atcataagtc tcggatcttt    660
cagaacctca cggggctttt agatgaagtg gttttaaagt ttgatcggaa ccgtgtgcgt    720
atccggaacg tggcctacga cacgctcccc attgtggtcc atggaaacgg tcccactaag    780
ctgcagctca actacctggg aaactacgtc cccaatggct ggactcctga gggaggctgt    840
ggcttctgca accaggaccg gaggacactc cggggggggc agcctccccc cgggtgttt     900 ctggccgtgt ttgtggaaca gcctactccg tttctgcccc gcttcctgca gcggctgcta    960
ctcctggact atccccccga cagggtcacc cttttcctgc acaacaacga ggtcttccat   1020
gaaccccaca tcgctgactc ctggccgcag ctccaggacc acttctcagc tgtgaagctc   1080
gtggggccgg aggaggctct gagcccaggc gaggccaggg acatggccat ggacctgtgt   1140
cggcaggacc ccgagtgtga gttctacttc agcctggacg ccgacgctgt cctcaccaac   1200
ctgcagaccc tgcgtatcct cattgaggag aacaggaagg tgatcgcccc catgctgtcc   1260
cgccacggca gctgtggtc caacttctgg ggcgccctga gccccgatga gtactacgcc    1320
cgctccgagg actacgtgga gctggtgcag cggaagcgag tggtgtgtg aatgtacca     1380 tacatctccc aggcctatgt gatccggggt gataccctgc ggatggagct gccccagagg   1440
gatgtgttct cggcagtgac acagacccg gacatggcct ctgtaagag ctttcgagac     1500 aagggcatct tcctccatct gagcaatcag catgaatttg gccggctcct ggccacttcc   1560
agatacgaca cggagcacct gcaccccgac tctggcagag tcttcgacaa ccccgtcgac   1620
tggaaggagc agtacatcca cgagaactac agccgggccc tggaagggga aggaatcgtg   1680
gagcagccat gccgggacgt gtactggttc ccactgctgt cagaacaaat gtgtgatgag   1740
ctggtggcag agatggagca ctacggccag tggtcaggcg gccggcatga ggattcaagg   1800
```

```
ctggctggag gctacgagaa tgtgcccacc gtggacatcc acatgaagca ggtggggtac    1860
gaggaccagt ggctgcagct gctgcggacg tatgtgggcc ccatgaccga gagcctgttt    1920
cccggttacc acaccaaggc gcgggcggtg atgaactttg tggttcgcta ccggccagac    1980
gagcagccgt ctctgcggcc acaccacgac tcatccacct tcaccctcaa cgttgccctc    2040
aaccacaagg gcctggacta tgagggaggt ggctgccgct tcctgcgcta cgactgtgtg    2100
atctcctccc cgaggaaggg ctgggcactc ctgcaccccg gccgcctcac ccactaccac    2160
gaggggctgc caacgacctg gggcacacgc tacatcatgg tgtcctttgt cgacccctga    2220
cactcaacca ctct                                                       2234
```

```
<210> SEQ ID NO 6
<211> LENGTH: 2167
<212> TYPE: DNA
<213> ORGANISM: Homo sapiens

<400> SEQUENCE: 6
```

```
tccgaccggc cccggggccg agacccggtc aacccagaga agctgctggt gatcactgtg     60
gccacagctg aaaccgaggg gtacctgcgt ttcctgcgct ctgcggagtt cttcaactac    120
actgtgcgga ccctgggcct gggagaggag tggcgagggg gtgatgtggc tcgaacagtt    180
ggtggaggac agaaggtccg gtggttaaag aaggaaatgg agaaatacgc tgaccgggag    240
gatatgatca tcatgtttgt ggatagctac gacgtgattc tggccggcag ccccacagag    300
ctgctgaaga agttcgtcca gagtggcagc cgcctgctct tctctgcaga gagcttctgc    360
tggcccgagt gggggctggc ggagcagtac cctgaggtgg gcacggggaa gcgcttcctc    420
aattctggtg gattcatcgg ttttgccacc accatccacc aaatcgtgcg ccagtggaag    480
tacaaggatg atgacgacga ccagctgttc tacacacggc tctacctgga cccaggactg    540
agggagaaac tcagccttaa tctggatcat aagtctcgga tctttcagaa cctcaacggg    600
gctttagatg aagtggtttt aaagtttgat cggaaccgtg tgcgtatccg gaacgtggcc    660
tacgacacgc tccccattgt ggtccatgga aacggtccca ctaagctgca gctcaactac    720
ctgggaaact acgtccccaa tggctggact cctgagggag gctgtggctt ctgcaaccag    780
gaccggagga cactcccggg ggggcagcct ccccccccggg tgtttctggc cgtgtttgtg    840
gaacagccta ctccgtttct gccccgcttc ctgcagcggc tgctactcct ggactatccc    900
cccgacaggg tcacccttttt cctgcacaac aacgaggtct ccatgaaccc cacatcgct    960 gactcctggc cgcagctcca ggaccacttc tcagctgtga agctcgtggg gccggaggag   1020
gctctgagcc caggcgaggc cagggacatg ccatggacc tgtgtcggca ggaccccgag   1080
tgtgagttct acttcagcct ggacgccgac gctgtcctca ccaacctgca gaccctgcgt   1140
atcctcattg aggagaacag gaaggtgatc gccccccatgc tgtcccgcca cggcaagctg   1200
tggtccaact tctgggcgc cctgagcccc gatgagtact acgcccgctc cgaggactac   1260
gtggagctgg tgcagcggaa gcgagtgggt gtgtggaatg taccatacat ctcccaggcc   1320
tatgtgatcc ggggtgatac cctgcggatg gagctgcccc agagggatgt gttctcgggc   1380
agtgacacag acccggacat ggccttctgt aagagctttc gagacaaggg catcttcctc   1440
catctgagca atcagcatga atttggccgg ctcctggcca cttccagata cgacacggag   1500
cacctgcacc ccgacctctg gcagatcttc gacaaccccg tcgactggaa ggagcagtac   1560
atccacgaga actacagccg ggccctggaa gggaaggaa tcgtggagca gccatgcccg   1620
gacgtgtact ggttcccact gctgtcagaa caaatgtgtg atgagctggt ggcagagatg   1680
```

```
gagcactacg gccagtggtc aggcggccgg catgaggatt caaggctggc tggaggctac    1740
gagaatgtgc ccaccgtgga catccacatg aagcaggtgg ggtacgagga ccagtggctg    1800
cagctgctgc ggacgtatgt gggcccatg accgagagcc tgtttccgg ttaccacacc    1860 aaggcgcggg cggtgatgaa ctttgtggtt cgctaccggc cagacgagca gccgtctctg    1920
cggccacacc acgactcatc caccttcacc ctcaacgttg ccctcaacca caagggcctg    1980
gactatgagg gaggtggctg ccgcttcctg cgctacgact gtgtgatctc ctccccgagg    2040
aagggctggg cactcctgca ccccggccgc ctcacccact accacgaggg gctgccaacg    2100
acctggggca cacgctacat catggtgtcc tttgtcgacc cctgacactc aaccactctg    2160
ccaaacc                                                               2167

<210> SEQ ID NO 7
<211> LENGTH: 2166
<212> TYPE: DNA
<213> ORGANISM: Homo sapiens

<400> SEQUENCE: 7
tccgaccggc cccggggccg agacccggtc aacccagaga agctgctggt gatcactgtg      60
gccacagctg aaaccgaggg gtacctgcgt ttcctgcgct ctgcggagtt cttcaactac     120
actgtgcgga ccctgggcct gggagaggag tggcgagggg gtgatgtggc tcgaacagtt     180
ggtggaggac agaaggtccg gtggttaaag aaggaaatgg agaaatacgc tgaccgggag     240
gatatgatca tcatgtttgt ggatagctac gacgtgattc tggccggcag ccccacagag     300
ctgctgaaga gttcgtcca gagtggcagc cgcctgctct ctctctgcaga gagcttctgc     360 tggcccgagt gggggctggc ggagcagtac cctgaggtgg gcacggggaa gcgcttcctc     420
aattctggtg gattcatcgg ttttgccacc accatccacc aaatcgtgcg ccagtggaag     480
tacaaggatg atgacgacga ccagctgttc tacacacggc tctacctgga cccaggactg     540
agggagaaac tcagccttaa tctggatcat aagtctcgga tctttcagaa cctcaacggg     600
gctttagatg aagtggtttt aagtttgatc ggaaccgtgt gcgtatccgg aacgtggcct     660
acgacacgct cccccattgtg gtccatggaa acggtcccac taagctgcag ctcaactacc     720
tgggaaacta cgtccccaat ggctggactc ctgagggagg ctgtggcttc tgcaaccagg     780
accggaggac actcccgggg gggcagcctc cccccgggt gtttctggcc gtgtttgtgg     840
aacagcctac tccgtttctg ccccgcttcc tgcagcggct gctactcctg gactatcccc     900
ccgacagggt cacccttttc ctgcacaaca acgaggtctt ccatgaaccc cacatcgctg     960
actcctggcc gcagctccag gaccacttct cagctgtgaa gctcgtgggg ccggaggagg    1020
ctctgagccc aggcgaggcc agggacatgg ccatggacct gtgtcggcag gaccccgagt    1080
gtgagttcta cttcagcctg gacgccgacg ctgtcctcac caacctgcag accctgcgta    1140
tcctcattga ggagaacagg aaggtgatcg cccccatgct gtcccgccac ggcaagctgt    1200
ggtccaactt ctggggcgcc ctgagcccg atgagtacta cgcccgctcc gaggactacg    1260
tggagctggt gcagcggaag cgagtggggtg tgtggaatgt accatacatc tcccaggcct    1320
atgtgatccg gggtgatacc ctgccggatg agctgcccca gagggatgtg ttctcgggca    1380
gtgacacaga cccggacatg gccttctgta agagctttcg agacaagggc atcttcctcc    1440
atctgagcaa tcagcatgaa tttgccggcc tcctggccac ttccagatac gacacggagc    1500
acctgcaccc cgacctctgg cagatcttcg acaacccgt cgactggaag gagcagtaca    1560
```

| | |
|---|---:|
| tccacgagaa ctacagccgg gccctggaag gggaaggaat cgtggagcag ccatgcccgg | 1620 |
| acgtgtactg gttcccactg ctgtcagaac aaatgtgtga tgagctggtg gcagagatgg | 1680 |
| agcactacgg ccagtggtca ggcggccggc atgaggattc aaggctggct ggaggctacg | 1740 |
| agaatgtgcc caccgtggac atccacatga agcaggtggg gtacgaggac cagtggctgc | 1800 |
| agctgctgcg gacgtatgtg ggccccatga ccgagagcct gtttcccggt taccacacca | 1860 |
| aggcgcgggc ggtgatgaac tttgtggttc gctaccggcc agacgagcag ccgtctctgc | 1920 |
| ggccacacca cgactcatcc accttcaccc tcaacgttgc cctcaaccac aagggcctgg | 1980 |
| actatgaggg aggtggctgc cgcttcctgc gctacgactg tgtgatctcc tccccgagga | 2040 |
| agggctgggc actcctgcac cccggccgcc tcacccacta ccacgagggg ctgccaacga | 2100 |
| cctggggcac acgctacatc atggtgtcct tgtcgaccc ctgacactca accactctgc | 2160 |
| caaacc | 2166 |

<210> SEQ ID NO 8
<211> LENGTH: 2167
<212> TYPE: DNA
<213> ORGANISM: Homo sapiens

<400> SEQUENCE: 8

| | |
|---|---:|
| tccgaccggc cccggggccg agacccggtc aacccagaga agctgctggt gatcactgtg | 60 |
| gccacagctg aaaccgaggg gtacctgcgt ttcctgcgct ctgcggagtt cttcaactac | 120 |
| actgtgcgga ccctgggcct gggagaggag tggcgagggg gtgatgtggc tcgaacagtt | 180 |
| ggtggaggac agaaggtccg gtggttaaag aaggaaatgg agaaatacgc tgaccgggag | 240 |
| gatatgatca tcatgtttgt ggatagctac gacgtgattc tggccggcag ccccacagag | 300 |
| ctgctgaaga agttcgtcca gagtggcagc cgcctgctct tctctgcaga gagcttctgc | 360 |
| tggcccgagt gggggctggc ggagcagtac cctgaggtgg gcacggggaa gcgcttcctc | 420 |
| aattctggtg gattcatcgg ttttgccacc accatccacc aaatcgtgcg ccagtggaag | 480 |
| tacaaggatg atgacgacga ccagctgttc tacacacggc tctacctgga cccaggactg | 540 |
| agggagaaac tcagccttaa tctggatcat aagtctcgga tctttcagaa cctcaacggg | 600 |
| gctttagatg aagtggtttt aaagtttgat cggaaccgtg tgcgtatccg gaacgtggcc | 660 |
| tacgacacgc tccccattgt ggtccatgga aacggtccca ctaagctgca gctcaactac | 720 |
| ctgggaaact acgtccccaa tggctggact cctgagggag gctgtggctt ctgcaaccag | 780 |
| gaccggagga cactcccggg ggggcagcct cccccccggg tgtttctggc cgtgtttgtg | 840 |
| gaacagccta ctccgtttct gccccgcttc ctgcagcggc tgctactcct ggactatccc | 900 |
| cccgacaggg tcacccttttt cctgcacaac aacgaggtct ccatgaacc ccacatcgct | 960 |
| gactcctggc cgcagctcca ggaccacttc tcagctgtga agctcgtggg gccggaggag | 1020 |
| gctctgagcc aggcgaggc cagggacatg ccatggacc tgtgtcggca ggaccccgag | 1080 |
| tgtgagttct acttcagcct ggacgccgac gctgtcctca ccaacctgca gaccctgcgt | 1140 |
| atcctcattg aggagaacag gaaggtgatc gcccccatgc tgtcccgcca cggcaagctg | 1200 |
| tggtccaact tctggggcgc cctgagcccc gatgagtact acgcccgctc cgaggactac | 1260 |
| gtggagctgg tgcagcggaa cgagtgggt gtgtggaatg taccatacat ctcccaggcc | 1320 |
| tatgtgatcc ggggtgatac cctgcggatg gagctgcccc agagggatgt gttctcgggc | 1380 |
| agtgacacag acccggacat ggccttctgt aagagctttc gagacaaggg catcttcctc | 1440 |
| catctgagca atcagcatga atttggccgg ctcctggcca cttccagata agacacggag | 1500 |

```
cacctgcacc ccgacctctg gcagatcttc gacaaccccg tcgactggaa ggagcagtac    1560
atccacgaga actacagccg ggccctggaa ggggaaggaa tcgtggagca gccatgcccg    1620
gacgtgtact ggttcccact gctgtcagaa caaatgtgtg atgagctggt ggcagagatg    1680
gagcactacg gccagtggtc aggcggccgg catgaggatt caaggctggc tggaggctac    1740
gagaatgtgc ccaccgtgga catccacatg aagcaggtgg ggtacgagga ccagtggctg    1800
cagctgctgc ggacgtatgt gggccccatg accgagagcc tgtttcccgg ttaccacacc    1860
aaggcgcggg cggtgatgaa ctttgtggtt cgctaccggc cagacgagca gccgtctctg    1920
cggccacacc acgactcatc caccttcacc ctcaacgttg ccctcaacca aagggcctg    1980 gactatgagg gaggtggctg ccgcttcctg cgctacgact gtgtgatctc ctccccgagg    2040
aagggctggg cactcctgca ccccggccgc ctcacccact accacgaggg gctgccaacg    2100
acctggggca cacgctacat catggtgtcc tttgtcgacc cctgacactc aaccactctg    2160
ccaaacc                                                              2167

<210> SEQ ID NO 9
<211> LENGTH: 2167
<212> TYPE: DNA
<213> ORGANISM: Homo sapiens

<400> SEQUENCE: 9
tccgaccggc cccggggccg agacccggtc aacccagaga agctgctggt gatcactgtg     60
gccacagctg aaaccgaggg gtacctgcgt ttcctgcgct ctgcggagtt cttcaactac    120
actgtgcgga ccctgggcct gggagaggag tggcgagggg gtgatgtggc tcgaacagtt    180
ggtggaggac agaaggtccg gtggttaaag aaggaaatgg agaaatacgc tgaccgggag    240
gatatgatca tcatgtttgt ggatagctac gacgtgattc tggccggcag ccccacagag    300
ctgctgaaga agttcgtcca gagtggcagc cgcctgctct ctctgcagag agcttctgc     360 tggcccgagt gggggctggc ggagcagtac cctgaggtgg cacggggaa gcgcttcctc    420 aattctggtg gattcatcgg ttttgccacc accatccacc aaatcgtgcg ccagtggaag    480
tacaaggatg atgacgacga ccagctgttc tacacacggc tctacctgga cccaggactg    540
agggagaaac tcagccttaa tctggatcat aagtctcgga tctttcagaa cctcaacggg    600
gctttagatg aagtggtttt aaagtttgat cggaaccgtg tgcgtatccg gaacgtggcc    660
tacgacacgc tccccattgt ggtccatgga acggtcccaa ctaagctgca gctcaactac    720
ctgggaaact acgtccccaa tggctggact cctgagggag gctgtggctt ctgcaaccag    780
gaccggagga cactcccggg ggggcagcct ccccccccggg tgtttctggc cgtgtttgtg    840
gaacagccta ctccgtttct gccccgcttc ctgcagcggc tgctactcct ggactatccc    900
cccgacaggg tcaccttttt cctgcacaac aacgaggtct ccatgaacc ccacatcgct    960 gactcctggc cgcagctcca ggaccacttc tcagctgtga agctcgtggg gccggaggag   1020
gctctgagcc caggcgaggc cagggacatg gccatggacc tgtgtcggca ggaccccgag   1080
tgtgagttct acttcagcct ggacgccgac gctgtcctca ccaacctgca gaccctgcgt   1140
atcctcattg aggagaacag gaaggtgatc gcccccatgc tgtcccgcca cggcaagctg   1200
tggtccaact tctgggggcgc cctgagcccc gatgagtact acgcccgctc cgaggactac   1260
gtggagctgg tgcagcggaa cgagtgggt gtgtggaatg taccatacat ctcccaggcc   1320
tatgtgatcc ggggtgatac cctgcggatg gagctgcccc agaggatgt gttctcgggc   1380
```

| | |
|---|---|
| agtgacacag acccggacat ggccttctgt aagagctttc gagacaaggg catcttcctc | 1440 |
| catctgagca atcagcatga atttggccgg ctcctggcca cttccagata cgacacggag | 1500 |
| cacctgcacc ccgacctctg gcagatcttc gacaaccccg tcgactggaa ggagcagtac | 1560 |
| atccacgaga actacagccg ggccctggaa ggggaaggaa tcgtggagca gccatgcccg | 1620 |
| gacgtgtact ggttcccact gctgtcagaa caaatgtgtg atgagctggt ggcagagatg | 1680 |
| gagcactacg ccagtggtc aggcggccgg catgaggatt caaggctggc tggaggctac | 1740 |
| gagaatgtgc ccaccgtgga catccacatg aagcaggtgg ggtacgagga ccagtggctg | 1800 |
| cagctgctgc ggacgtatgt gggccccatg accgagagcc tgtttcccgg ttaccacacc | 1860 |
| aaggcgcggg cggtgatgaa ctttgtggtt cgctaccggc cagacgagca gccgtctctg | 1920 |
| cggccacacc acgcctcatc caccttcacc ctcaacgttg ccctcaacca caagggcctg | 1980 |
| gactatgagg gaggtggctg ccgcttcctg cgctacgact gtgtgatctc ctccccgagg | 2040 |
| aagggctggg cactcctgca ccccggccgc ctcacccact accacgaggg gctgccaacg | 2100 |
| acctggggca cacgctacat catggtgtcc tttgtcgacc cctgacactc aaccactctg | 2160 |
| ccaaacc | 2167 |

<210> SEQ ID NO 10
<211> LENGTH: 2166
<212> TYPE: DNA
<213> ORGANISM: Homo sapiens

<400> SEQUENCE: 10

| | |
|---|---|
| tccgaccggc cccggggccg agaccggtc aacccagaga agctgctggt gatcactgtg | 60 |
| gccacagctg aaaccgaggg gtacctgcgt ttcctgcgct ctgcggagtt cttcaactac | 120 |
| actgtgcgga ccctgggcct gggagaggag tggcgagggg gtgatgtggc tcgaacagtt | 180 |
| ggtggaggac agaaggtccg gtggttaaag aaggaaatgg agaaatacgc tgaccgggag | 240 |
| gatatgatca tcatgtttgt ggatagctac gacgtgattc tggccggcag ccccacagag | 300 |
| ctgctgaaga agttcgtcca gagtggcagc cgcctgctct tctctgcaga gagcttctgc | 360 |
| tggcccgagt gggggctggc ggagcagtac cctgaggtgg gcacggggaa gcgcttcctc | 420 |
| aattctggtg gattcatcgg ttttgccacc accatccacc aaatcgtgcg ccagtggaag | 480 |
| tacaaggatg atgacgacga ccagctgttc tacacacggc tctacctgga cccaggactg | 540 |
| agggagaaac tcagccttaa tctggatcat aagtctcgga tctttcagaa cctcaacggg | 600 |
| gctttagatg aagtggtttt aaagtttgat cggaaccgtg tgcgtatccg gaacgtggcc | 660 |
| tacgacacgc tccccattgt ggtccatgga acggtccca ctaagctgca gctcaactac | 720 |
| ctgggaaaact acgtccccaa tggctggact cctgagggag gctgtggctt ctgcaaccag | 780 |
| gaccggagga cactcccggg ggggcagcct cccccccggg tgtttctggc cgtgtttgtg | 840 |
| gaacagccta ctccgtttct gccccgcttc ctgcagcggc tgctactcct ggactatccc | 900 |
| cccgacaggg tcaccctttt cctgcacaac aacgaggtct ccatgaaccc cacatcgct | 960 |
| gactcctggc cgcagctcca ggaccacttc tcagctgtga agctcgtggg gccggaggag | 1020 |
| gctctgagcc caggcgaggc caggacatg ccatggacc tgtgtcggca ggaccccgag | 1080 |
| tgtgagttct acttcagcct ggacgccgac gctgtcctca ccaacctgca gaccctgcgt | 1140 |
| atcctcattg aggagaacag gaaggtgatc gcccccatgc tgtcccgcca cggcaagctg | 1200 |
| tggtccaact tctgggcgc cctgagcccc gatgagtact acgcccgctc cgaggactac | 1260 |
| gtggagctgg tgcagcggaa gcgagtgggt gtgtggaatg taccatacat ctcccaggcc | 1320 |

```
tatgtgatcc ggggtgatac cctgcggatg gagctgcccc agagggatgt gttctcgggc   1380
agtgacacag acccggacat ggccttctgt aagagctttc gagacaaggg catcttcctc   1440
catctgagca atcagcatga atttggccgg ctcctggcca cttccagata cgacacggag   1500
cacctgcacc ccgacctctg cagatcttc gacaaccccg tcgactggaa ggagcagtac    1560
atccacgaga actacagccg ggccctggaa ggggaaggaa tcgtggagca gccatgcccg   1620
gacgtgtact ggttcccact gctgtcagaa caaatgtgtg atgagctggt ggcagagatg   1680
gagcactacg ccagtggtc aggcggccgg catgaggatt caaggctggc tggaggctac    1740
gagaatgtgc ccaccgtgga catccacatg aagcaggtgg ggtacgagga ccagtggctg   1800
cagctgctgc ggacgtatgt gggcccatg accgagagcc tgtttcccgg ttaccacacc    1860
aaggcgcggg cggtgatgaa ctttgtggtt cgctaccggc agacgagca gccgtctctg     1920 cggccacacc acgctcatcc accttcaccc tcaacgttgc cctcaaccac aagggcctgg   1980
actatgaggg aggtggctgc cgcttcctgc gctacgactg tgtgatctcc tccccgagga   2040
agggctgggc actcctgcac cccggccgcc tcacccacta ccacgagggg ctgccaacga   2100
cctggggcac acgctacatc atggtgtcct ttgtcgaccc ctgacactca accactctgc   2160
caaacc                                                              2166

<210> SEQ ID NO 11
<211> LENGTH: 738
<212> TYPE: PRT
<213> ORGANISM: Homo sapiens

<400> SEQUENCE: 11

Met Thr Ser Ser Gly Pro Gly Pro Arg Phe Leu Leu Leu Pro Leu
  1               5                  10                  15

Leu Leu Pro Pro Ala Ala Ser Ala Ser Asp Arg Pro Arg Gly Arg Asp
             20                  25                  30

Pro Val Asn Pro Glu Lys Leu Leu Val Ile Thr Val Ala Thr Ala Glu
         35                  40                  45

Thr Glu Gly Tyr Leu Arg Phe Leu Arg Ser Ala Glu Phe Phe Asn Tyr
     50                  55                  60

Thr Val Arg Thr Leu Gly Leu Gly Glu Glu Trp Arg Gly Gly Asp Val
 65                  70                  75                  80

Ala Arg Thr Val Gly Gly Gly Gln Lys Val Arg Trp Leu Lys Lys Glu
                 85                  90                  95

Met Glu Lys Tyr Ala Asp Arg Glu Asp Met Ile Ile Met Phe Val Asp
            100                 105                 110

Ser Tyr Asp Val Ile Leu Ala Gly Ser Pro Thr Glu Leu Leu Lys Lys
        115                 120                 125

Phe Val Gln Ser Gly Ser Arg Leu Leu Phe Ser Ala Glu Ser Phe Cys
    130                 135                 140

Trp Pro Glu Trp Gly Leu Ala Glu Gln Tyr Pro Glu Val Gly Thr Gly
145                 150                 155                 160

Lys Arg Phe Leu Asn Ser Gly Gly Phe Ile Gly Phe Ala Thr Thr Ile
                165                 170                 175

His Gln Ile Val Arg Gln Trp Lys Tyr Lys Asp Asp Asp Asp Gln
            180                 185                 190

Leu Phe Tyr Thr Arg Leu Tyr Leu Asp Pro Gly Leu Arg Glu Lys Leu
        195                 200                 205

Ser Leu Asn Leu Asp His Lys Ser Arg Ile Phe Gln Asn Leu Asn Gly
```

-continued

```
            210                 215                 220
Ala Leu Asp Glu Val Val Leu Lys Phe Asp Arg Asn Arg Val Arg Ile
225                 230                 235                 240
Arg Asn Val Ala Tyr Asp Thr Leu Pro Ile Val Val His Gly Asn Gly
                    245                 250                 255
Pro Thr Lys Leu Gln Leu Asn Tyr Leu Gly Asn Tyr Val Pro Asn Gly
                    260                 265                 270
Trp Thr Pro Glu Gly Gly Cys Gly Phe Cys Asn Gln Asp Arg Arg Thr
                    275                 280                 285
Leu Pro Gly Gly Gln Pro Pro Arg Val Phe Leu Ala Val Phe Val
290                 295                 300
Glu Gln Pro Thr Pro Phe Leu Pro Arg Phe Leu Gln Arg Leu Leu Leu
305                 310                 315                 320
Leu Asp Tyr Pro Pro Asp Arg Val Thr Leu Phe Leu His Asn Asn Glu
                    325                 330                 335
Val Phe His Glu Pro His Ile Ala Asp Ser Trp Pro Gln Leu Gln Asp
                    340                 345                 350
His Phe Ser Ala Val Lys Leu Val Gly Pro Glu Glu Ala Leu Ser Pro
                    355                 360                 365
Gly Glu Ala Arg Asp Met Ala Met Asp Leu Cys Arg Gln Asp Pro Glu
                    370                 375                 380
Cys Glu Phe Tyr Phe Ser Leu Asp Ala Asp Ala Val Leu Thr Asn Leu
385                 390                 395                 400
Gln Thr Leu Arg Ile Leu Ile Glu Glu Asn Arg Lys Val Ile Ala Pro
                    405                 410                 415
Met Leu Ser Arg His Gly Lys Leu Trp Ser Asn Phe Trp Gly Ala Leu
                    420                 425                 430
Ser Pro Asp Glu Tyr Tyr Ala Arg Ser Glu Asp Tyr Val Glu Leu Val
                    435                 440                 445
Gln Arg Lys Arg Val Gly Val Trp Asn Val Pro Tyr Ile Ser Gln Ala
                    450                 455                 460
Tyr Val Ile Arg Gly Asp Thr Leu Arg Met Glu Leu Pro Gln Arg Asp
465                 470                 475                 480
Val Phe Ser Gly Ser Asp Thr Asp Pro Asp Met Ala Phe Cys Lys Ser
                    485                 490                 495
Phe Arg Asp Lys Gly Ile Phe Leu His Leu Ser Asn Gln His Glu Phe
                    500                 505                 510
Gly Arg Leu Leu Ala Thr Ser Arg Tyr Asp Thr Glu His Leu His Pro
                    515                 520                 525
Asp Leu Trp Gln Ile Phe Asp Asn Pro Val Asp Trp Lys Glu Gln Tyr
                    530                 535                 540
Ile His Glu Asn Tyr Ser Arg Ala Leu Glu Gly Glu Gly Ile Val Glu
545                 550                 555                 560
Gln Pro Cys Pro Asp Val Tyr Trp Phe Pro Leu Leu Ser Glu Gln Met
                    565                 570                 575
Cys Asp Glu Leu Val Ala Glu Met Glu His Tyr Gly Gln Trp Ser Gly
                    580                 585                 590
Gly Arg His Glu Asp Ser Arg Leu Ala Gly Gly Tyr Glu Asn Val Pro
                    595                 600                 605
Thr Val Asp Ile His Met Lys Gln Val Gly Tyr Glu Asp Gln Trp Leu
                    610                 615                 620
Gln Leu Leu Arg Thr Tyr Val Gly Pro Met Thr Glu Ser Leu Phe Pro
625                 630                 635                 640
```

```
Gly Tyr His Thr Lys Ala Arg Ala Val Met Asn Phe Val Val Arg Tyr
                645                 650                 655

Arg Pro Asp Glu Gln Pro Ser Leu Arg Pro His His Asp Ser Ser Thr
            660                 665                 670

Phe Thr Leu Asn Val Ala Leu Asn His Lys Gly Leu Asp Tyr Glu Gly
        675                 680                 685

Gly Gly Cys Arg Phe Leu Arg Tyr Asp Cys Val Ile Ser Ser Pro Arg
    690                 695                 700

Lys Gly Trp Ala Leu Leu His Pro Gly Arg Leu Thr His Tyr His Glu
705                 710                 715                 720

Gly Leu Pro Thr Thr Trp Gly Thr Arg Tyr Ile Met Val Ser Phe Val
                725                 730                 735

Asp Pro

<210> SEQ ID NO 12
<211> LENGTH: 714
<212> TYPE: PRT
<213> ORGANISM: Homo sapiens

<400> SEQUENCE: 12

Ser Asp Arg Pro Arg Gly Arg Asp Pro Val Asn Pro Glu Lys Leu Leu
  1               5                  10                  15

Val Ile Thr Val Ala Thr Ala Glu Thr Glu Gly Tyr Leu Arg Phe Leu
                 20                  25                  30

Arg Ser Ala Glu Phe Phe Asn Tyr Thr Val Arg Thr Leu Gly Leu Gly
             35                  40                  45

Glu Glu Trp Arg Gly Gly Asp Val Ala Arg Thr Val Gly Gly Gly Gln
         50                  55                  60

Lys Val Arg Trp Leu Lys Lys Glu Met Glu Lys Tyr Ala Asp Arg Glu
 65                  70                  75                  80

Asp Met Ile Ile Met Phe Val Asp Ser Tyr Asp Val Ile Leu Ala Gly
                 85                  90                  95

Ser Pro Thr Glu Leu Leu Lys Lys Phe Val Gln Ser Gly Ser Arg Leu
            100                 105                 110

Leu Phe Ser Ala Glu Ser Phe Cys Trp Pro Glu Trp Gly Leu Ala Glu
        115                 120                 125

Gln Tyr Pro Glu Val Gly Thr Gly Lys Arg Phe Leu Asn Ser Gly Gly
    130                 135                 140

Phe Ile Gly Phe Ala Thr Thr Ile His Gln Ile Val Arg Gln Trp Lys
145                 150                 155                 160

Tyr Lys Asp Asp Asp Asp Gln Leu Phe Tyr Thr Arg Leu Tyr Leu
                165                 170                 175

Asp Pro Gly Leu Arg Glu Lys Leu Ser Leu Asn Leu Asp His Lys Ser
            180                 185                 190

Arg Ile Phe Gln Asn Leu Asn Gly Ala Leu Asp Glu Val Val Leu Lys
        195                 200                 205

Phe Asp Arg Asn Arg Val Arg Ile Arg Asn Val Ala Tyr Asp Thr Leu
    210                 215                 220

Pro Ile Val Val His Gly Asn Gly Pro Thr Lys Leu Gln Leu Asn Tyr
225                 230                 235                 240

Leu Gly Asn Tyr Val Pro Asn Gly Trp Thr Pro Glu Gly Gly Cys Gly
                245                 250                 255

Phe Cys Asn Gln Asp Arg Arg Thr Leu Pro Gly Gly Gln Pro Pro Pro
            260                 265                 270
```

```
Arg Val Phe Leu Ala Val Phe Val Glu Gln Pro Thr Pro Phe Leu Pro
        275                 280                 285

Arg Phe Leu Gln Arg Leu Leu Leu Asp Tyr Pro Pro Asp Arg Val
        290                 295                 300

Thr Leu Phe Leu His Asn Asn Glu Val Phe His Glu Pro His Ile Ala
305                 310                 315                 320

Asp Ser Trp Pro Gln Leu Gln Asp His Phe Ser Ala Val Lys Leu Val
                    325                 330                 335

Gly Pro Glu Glu Ala Leu Ser Pro Gly Glu Ala Arg Asp Met Ala Met
                340                 345                 350

Asp Leu Cys Arg Gln Asp Pro Glu Cys Glu Phe Tyr Phe Ser Leu Asp
            355                 360                 365

Ala Asp Ala Val Leu Thr Asn Leu Gln Thr Leu Arg Ile Leu Ile Glu
        370                 375                 380

Glu Asn Arg Lys Val Ile Ala Pro Met Leu Ser Arg His Gly Lys Leu
385                 390                 395                 400

Trp Ser Asn Phe Trp Gly Ala Leu Ser Pro Asp Glu Tyr Tyr Ala Arg
                    405                 410                 415

Ser Glu Asp Tyr Val Glu Leu Val Gln Arg Lys Arg Val Gly Val Trp
                420                 425                 430

Asn Val Pro Tyr Ile Ser Gln Ala Tyr Val Ile Arg Gly Asp Thr Leu
            435                 440                 445

Arg Met Glu Leu Pro Gln Arg Asp Val Phe Ser Gly Ser Asp Thr Asp
        450                 455                 460

Pro Asp Met Ala Phe Cys Lys Ser Phe Arg Asp Lys Gly Ile Phe Leu
465                 470                 475                 480

His Leu Ser Asn Gln His Glu Phe Gly Arg Leu Leu Ala Thr Ser Arg
                    485                 490                 495

Tyr Asp Thr Glu His Leu His Pro Asp Leu Trp Gln Ile Phe Asp Asn
                500                 505                 510

Pro Val Asp Trp Lys Glu Gln Tyr Ile His Glu Asn Tyr Ser Arg Ala
            515                 520                 525

Leu Glu Gly Glu Gly Ile Val Glu Gln Pro Cys Pro Asp Val Tyr Trp
        530                 535                 540

Phe Pro Leu Leu Ser Glu Gln Met Cys Asp Glu Leu Val Ala Glu Met
545                 550                 555                 560

Glu His Tyr Gly Gln Trp Ser Gly Gly Arg His Glu Asp Ser Arg Leu
                    565                 570                 575

Ala Gly Gly Tyr Glu Asn Val Pro Thr Val Asp Ile His Met Lys Gln
                580                 585                 590

Val Gly Tyr Glu Asp Gln Trp Leu Gln Leu Arg Thr Tyr Val Gly
            595                 600                 605

Pro Met Thr Glu Ser Leu Phe Pro Gly Tyr His Thr Lys Ala Arg Ala
        610                 615                 620

Val Met Asn Phe Val Val Arg Tyr Arg Pro Asp Glu Gln Pro Ser Leu
625                 630                 635                 640

Arg Pro His His Asp Ser Ser Thr Phe Thr Leu Asn Val Ala Leu Asn
                    645                 650                 655

His Lys Gly Leu Asp Tyr Glu Gly Gly Gly Cys Arg Phe Leu Arg Tyr
                660                 665                 670

Asp Cys Val Ile Ser Ser Pro Arg Lys Gly Trp Ala Leu Leu His Pro
            675                 680                 685
```

```
Gly Arg Leu Thr His Tyr His Glu Gly Leu Pro Thr Thr Trp Gly Thr
690                 695                 700

Arg Tyr Ile Met Val Ser Phe Val Asp Pro
705                 710

<210> SEQ ID NO 13
<211> LENGTH: 332
<212> TYPE: PRT
<213> ORGANISM: Homo sapiens

<400> SEQUENCE: 13

Ser Asp Arg Pro Arg Gly Arg Asp Pro Val Asn Pro Glu Lys Leu Leu
1               5                   10                  15

Val Ile Thr Val Ala Thr Ala Glu Thr Glu Gly Tyr Leu Arg Phe Leu
                20                  25                  30

Arg Ser Ala Glu Phe Phe Asn Tyr Thr Val Arg Thr Leu Gly Leu Gly
            35                  40                  45

Glu Glu Trp Arg Gly Gly Asp Val Ala Arg Thr Val Gly Gly Gly Gln
        50                  55                  60

Lys Val Arg Trp Leu Lys Lys Glu Met Glu Lys Tyr Ala Asp Arg Glu
65                  70                  75                  80

Asp Met Ile Ile Met Phe Val Asp Ser Tyr Asp Val Ile Leu Ala Gly
                85                  90                  95

Ser Pro Thr Glu Leu Leu Lys Lys Phe Val Gln Ser Gly Ser Arg Leu
            100                 105                 110

Leu Phe Ser Ala Glu Ser Phe Cys Trp Pro Glu Trp Gly Leu Ala Glu
        115                 120                 125

Gln Tyr Pro Glu Val Gly Thr Gly Lys Arg Phe Leu Asn Ser Gly Gly
    130                 135                 140

Phe Ile Gly Phe Ala Thr Thr Ile His Gln Ile Val Arg Gln Trp Lys
145                 150                 155                 160

Tyr Lys Asp Asp Asp Asp Gln Leu Phe Tyr Thr Arg Leu Tyr Leu
                165                 170                 175

Asp Pro Gly Leu Arg Glu Lys Leu Ser Leu Asn Leu Asp His Lys Ser
            180                 185                 190

Arg Ile Phe Gln Asn Leu Asn Gly Ala Leu Asp Glu Val Val Leu Ser
        195                 200                 205

Leu Ile Gly Thr Val Cys Val Ser Gly Thr Trp Pro Thr Thr Arg Ser
    210                 215                 220

Pro Leu Trp Ser Met Glu Thr Val Pro Leu Ser Cys Ser Ser Thr Thr
225                 230                 235                 240

Trp Glu Thr Thr Ser Pro Met Ala Gly Leu Leu Arg Glu Ala Val Ala
                245                 250                 255

Ser Ala Thr Arg Thr Gly Gly His Ser Arg Gly Gly Ser Leu Pro Pro
            260                 265                 270

Gly Cys Phe Trp Pro Cys Leu Trp Asn Ser Leu Leu Arg Phe Cys Pro
        275                 280                 285

Ala Ser Cys Ser Gly Cys Tyr Ser Trp Thr Ile Pro Pro Thr Gly Ser
    290                 295                 300

Pro Phe Ser Cys Thr Thr Thr Arg Ser Ser Met Asn Pro Thr Ser Leu
305                 310                 315                 320

Thr Pro Gly Arg Ser Ser Arg Thr Thr Ser Gln Leu
                325                 330

<210> SEQ ID NO 14
```

<211> LENGTH: 496
<212> TYPE: PRT
<213> ORGANISM: Homo sapiens

<400> SEQUENCE: 14

```
Ser Asp Arg Pro Arg Gly Arg Asp Pro Val Asn Pro Glu Lys Leu Leu
  1               5                  10                  15

Val Ile Thr Val Ala Thr Ala Glu Thr Glu Gly Tyr Leu Arg Phe Leu
                 20                  25                  30

Arg Ser Ala Glu Phe Phe Asn Tyr Thr Val Arg Thr Leu Gly Leu Gly
             35                  40                  45

Glu Glu Trp Arg Gly Gly Asp Val Ala Arg Thr Val Gly Gly Gly Gln
     50                  55                  60

Lys Val Arg Trp Leu Lys Lys Glu Met Glu Lys Tyr Ala Asp Arg Glu
 65                  70                  75                  80

Asp Met Ile Ile Met Phe Val Asp Ser Tyr Asp Val Ile Leu Ala Gly
                 85                  90                  95

Ser Pro Thr Glu Leu Leu Lys Lys Phe Val Gln Ser Gly Ser Arg Leu
            100                 105                 110

Leu Phe Ser Ala Glu Ser Phe Cys Trp Pro Glu Trp Gly Leu Ala Glu
        115                 120                 125

Gln Tyr Pro Glu Val Gly Thr Gly Lys Arg Phe Leu Asn Ser Gly Gly
    130                 135                 140

Phe Ile Gly Phe Ala Thr Thr Ile His Gln Ile Val Arg Gln Trp Lys
145                 150                 155                 160

Tyr Lys Asp Asp Asp Asp Gln Leu Phe Tyr Thr Arg Leu Tyr Leu
                165                 170                 175

Asp Pro Gly Leu Arg Glu Lys Leu Ser Leu Asn Leu Asp His Lys Ser
            180                 185                 190

Arg Ile Phe Gln Asn Leu Asn Gly Ala Leu Asp Glu Val Val Leu Lys
        195                 200                 205

Phe Asp Arg Asn Arg Val Arg Ile Arg Asn Val Ala Tyr Asp Thr Leu
    210                 215                 220

Pro Ile Val Val His Gly Asn Gly Pro Thr Lys Leu Gln Leu Asn Tyr
225                 230                 235                 240

Leu Gly Asn Tyr Val Pro Asn Gly Trp Thr Pro Glu Gly Gly Cys Gly
                245                 250                 255

Phe Cys Asn Gln Asp Arg Arg Thr Leu Pro Gly Gly Gln Pro Pro Pro
            260                 265                 270

Arg Val Phe Leu Ala Val Phe Val Glu Gln Pro Thr Pro Phe Leu Pro
        275                 280                 285

Arg Phe Leu Gln Arg Leu Leu Leu Asp Tyr Pro Pro Asp Arg Val
    290                 295                 300

Thr Leu Phe Leu His Asn Asn Glu Val Phe His Glu Pro His Ile Ala
305                 310                 315                 320

Asp Ser Trp Pro Gln Leu Gln Asp His Phe Ser Ala Val Lys Leu Val
                325                 330                 335

Gly Pro Glu Glu Ala Leu Ser Pro Gly Glu Ala Arg Asp Met Ala Met
            340                 345                 350

Asp Leu Cys Arg Gln Asp Pro Glu Cys Glu Phe Tyr Phe Ser Leu Asp
        355                 360                 365

Ala Asp Ala Val Leu Thr Asn Leu Gln Thr Leu Arg Ile Leu Ile Glu
    370                 375                 380

Glu Asn Arg Lys Val Ile Ala Pro Met Leu Ser Arg His Gly Lys Leu
```

```
                385                 390                 395                 400
Trp Ser Asn Phe Trp Gly Ala Leu Ser Pro Asp Glu Tyr Tyr Ala Arg
                405                 410                 415

Ser Glu Asp Tyr Val Glu Leu Val Gln Arg Lys Arg Val Gly Val Trp
            420                 425                 430

Asn Val Pro Tyr Ile Ser Gln Ala Tyr Val Ile Arg Gly Asp Thr Leu
            435                 440                 445

Arg Met Glu Leu Pro Gln Arg Asp Val Phe Ser Gly Ser Asp Thr Asp
        450                 455                 460

Pro Asp Met Ala Phe Cys Lys Ser Phe Arg Asp Lys Gly Ile Phe Leu
465                 470                 475                 480

His Leu Ser Asn Gln His Glu Phe Gly Arg Leu Leu Ala Thr Ser Arg
                485                 490                 495

<210> SEQ ID NO 15
<211> LENGTH: 714
<212> TYPE: PRT
<213> ORGANISM: Homo sapiens

<400> SEQUENCE: 15

Ser Asp Arg Pro Arg Gly Arg Asp Pro Val Asn Pro Glu Lys Leu Leu
1               5                   10                  15

Val Ile Thr Val Ala Thr Ala Glu Thr Glu Gly Tyr Leu Arg Phe Leu
            20                  25                  30

Arg Ser Ala Glu Phe Phe Asn Tyr Thr Val Arg Thr Leu Gly Leu Gly
        35                  40                  45

Glu Glu Trp Arg Gly Gly Asp Val Ala Arg Thr Val Gly Gly Gly Gln
    50                  55                  60

Lys Val Arg Trp Leu Lys Lys Glu Met Glu Lys Tyr Ala Asp Arg Glu
65                  70                  75                  80

Asp Met Ile Ile Met Phe Val Asp Ser Tyr Asp Val Ile Leu Ala Gly
                85                  90                  95

Ser Pro Thr Glu Leu Leu Lys Lys Phe Val Gln Ser Gly Ser Arg Leu
            100                 105                 110

Leu Phe Ser Ala Glu Ser Phe Cys Trp Pro Glu Trp Gly Leu Ala Glu
        115                 120                 125

Gln Tyr Pro Glu Val Gly Thr Gly Lys Arg Phe Leu Asn Ser Gly Gly
    130                 135                 140

Phe Ile Gly Phe Ala Thr Thr Ile His Gln Ile Val Arg Gln Trp Lys
145                 150                 155                 160

Tyr Lys Asp Asp Asp Asp Gln Leu Phe Tyr Thr Arg Leu Tyr Leu
                165                 170                 175

Asp Pro Gly Leu Arg Glu Lys Leu Ser Leu Asn Leu Asp His Lys Ser
            180                 185                 190

Arg Ile Phe Gln Asn Leu Asn Gly Ala Leu Asp Glu Val Val Leu Lys
        195                 200                 205

Phe Asp Arg Asn Arg Val Arg Ile Arg Asn Val Ala Tyr Asp Thr Leu
    210                 215                 220

Pro Ile Val Val His Gly Asn Gly Pro Thr Lys Leu Gln Leu Asn Tyr
225                 230                 235                 240

Leu Gly Asn Tyr Val Pro Asn Gly Trp Thr Pro Glu Gly Gly Cys Gly
                245                 250                 255

Phe Cys Asn Gln Asp Arg Arg Thr Leu Pro Gly Gly Gln Pro Pro Pro
            260                 265                 270
```

-continued

```
Arg Val Phe Leu Ala Val Phe Val Glu Gln Pro Thr Pro Phe Leu Pro
        275                 280                 285

Arg Phe Leu Gln Arg Leu Leu Leu Asp Tyr Pro Pro Asp Arg Val
        290                 295                 300

Thr Leu Phe Leu His Asn Asn Glu Val Phe His Glu Pro His Ile Ala
305                 310                 315                 320

Asp Ser Trp Pro Gln Leu Gln Asp His Phe Ser Ala Val Lys Leu Val
                325                 330                 335

Gly Pro Glu Glu Ala Leu Ser Pro Gly Glu Ala Arg Asp Met Ala Met
                340                 345                 350

Asp Leu Cys Arg Gln Asp Pro Glu Cys Glu Phe Tyr Phe Ser Leu Asp
            355                 360                 365

Ala Asp Ala Val Leu Thr Asn Leu Gln Thr Leu Arg Ile Leu Ile Glu
370                 375                 380

Glu Asn Arg Lys Val Ile Ala Pro Met Leu Ser Arg His Gly Lys Leu
385                 390                 395                 400

Trp Ser Asn Phe Trp Gly Ala Leu Ser Pro Asp Glu Tyr Tyr Ala Arg
                405                 410                 415

Ser Glu Asp Tyr Val Glu Leu Val Gln Arg Lys Arg Val Gly Val Trp
                420                 425                 430

Asn Val Pro Tyr Ile Ser Gln Ala Tyr Val Ile Arg Gly Asp Thr Leu
            435                 440                 445

Arg Met Glu Leu Pro Gln Arg Asp Val Phe Ser Gly Ser Asp Thr Asp
        450                 455                 460

Pro Asp Met Ala Phe Cys Lys Ser Phe Arg Asp Lys Gly Ile Phe Leu
465                 470                 475                 480

His Leu Ser Asn Gln His Glu Phe Gly Arg Leu Leu Ala Thr Ser Arg
                485                 490                 495

Tyr Asp Thr Glu His Leu His Pro Asp Leu Trp Gln Ile Phe Asp Asn
                500                 505                 510

Pro Val Asp Trp Lys Glu Gln Tyr Ile His Glu Asn Tyr Ser Arg Ala
            515                 520                 525

Leu Glu Gly Glu Gly Ile Val Glu Gln Pro Cys Pro Asp Val Tyr Trp
        530                 535                 540

Phe Pro Leu Leu Ser Glu Gln Met Cys Asp Glu Leu Val Ala Glu Met
545                 550                 555                 560

Glu His Tyr Gly Gln Trp Ser Gly Gly Arg His Glu Asp Ser Arg Leu
                565                 570                 575

Ala Gly Gly Tyr Glu Asn Val Pro Thr Val Asp Ile His Met Lys Gln
                580                 585                 590

Val Gly Tyr Glu Asp Gln Trp Leu Gln Leu Leu Arg Thr Tyr Val Gly
            595                 600                 605

Pro Met Thr Glu Ser Leu Phe Pro Gly Tyr His Thr Lys Ala Arg Ala
        610                 615                 620

Val Met Asn Phe Val Val Arg Tyr Arg Pro Asp Glu Gln Pro Ser Leu
625                 630                 635                 640

Arg Pro His His Ala Ser Ser Thr Phe Thr Leu Asn Val Ala Leu Asn
                645                 650                 655

His Lys Gly Leu Asp Tyr Glu Gly Gly Gly Cys Arg Phe Leu Arg Tyr
                660                 665                 670

Asp Cys Val Ile Ser Ser Pro Arg Lys Gly Trp Ala Leu Leu His Pro
            675                 680                 685

Gly Arg Leu Thr His Tyr His Glu Gly Leu Pro Thr Thr Trp Gly Thr
```

```
                690               695               700
Arg Tyr Ile Met Val Ser Phe Val Asp Pro
705                 710

<210> SEQ ID NO 16
<211> LENGTH: 674
<212> TYPE: PRT
<213> ORGANISM: Homo sapiens

<400> SEQUENCE: 16

Ser Asp Arg Pro Arg Gly Arg Asp Pro Val Asn Pro Glu Lys Leu Leu
  1               5                  10                  15

Val Ile Thr Val Ala Thr Ala Glu Thr Glu Gly Tyr Leu Arg Phe Leu
             20                  25                  30

Arg Ser Ala Glu Phe Phe Asn Tyr Thr Val Arg Thr Leu Gly Leu Gly
         35                  40                  45

Glu Glu Trp Arg Gly Gly Asp Val Ala Arg Thr Val Gly Gly Gly Gln
     50                  55                  60

Lys Val Arg Trp Leu Lys Lys Glu Met Glu Lys Tyr Ala Asp Arg Glu
 65                  70                  75                  80

Asp Met Ile Ile Met Phe Val Asp Ser Tyr Asp Val Ile Leu Ala Gly
                 85                  90                  95

Ser Pro Thr Glu Leu Leu Lys Lys Phe Val Gln Ser Gly Ser Arg Leu
            100                 105                 110

Leu Phe Ser Ala Glu Ser Phe Cys Trp Pro Glu Trp Gly Leu Ala Glu
        115                 120                 125

Gln Tyr Pro Glu Val Gly Thr Gly Lys Arg Phe Leu Asn Ser Gly Gly
    130                 135                 140

Phe Ile Gly Phe Ala Thr Thr Ile His Gln Ile Val Arg Gln Trp Lys
145                 150                 155                 160

Tyr Lys Asp Asp Asp Asp Gln Leu Phe Tyr Thr Arg Leu Tyr Leu
                165                 170                 175

Asp Pro Gly Leu Arg Glu Lys Leu Ser Leu Asn Leu Asp His Lys Ser
            180                 185                 190

Arg Ile Phe Gln Asn Leu Asn Gly Ala Leu Asp Glu Val Val Leu Lys
        195                 200                 205

Phe Asp Arg Asn Arg Val Arg Ile Arg Asn Val Ala Tyr Asp Thr Leu
    210                 215                 220

Pro Ile Val Val His Gly Asn Gly Pro Thr Lys Leu Gln Leu Asn Tyr
225                 230                 235                 240

Leu Gly Asn Tyr Val Pro Asn Gly Trp Thr Pro Glu Gly Gly Cys Gly
                245                 250                 255

Phe Cys Asn Gln Asp Arg Arg Thr Leu Pro Gly Gly Gln Pro Pro
            260                 265                 270

Arg Val Phe Leu Ala Val Phe Val Glu Gln Pro Thr Pro Phe Leu Pro
        275                 280                 285

Arg Phe Leu Gln Arg Leu Leu Leu Asp Tyr Pro Pro Asp Arg Val
    290                 295                 300

Thr Leu Phe Leu His Asn Asn Glu Val Phe His Glu Pro His Ile Ala
305                 310                 315                 320

Asp Ser Trp Pro Gln Leu Gln Asp His Phe Ser Ala Val Lys Leu Val
                325                 330                 335

Gly Pro Glu Glu Ala Leu Ser Pro Gly Glu Ala Arg Asp Met Ala Met
            340                 345                 350
```

-continued

Asp Leu Cys Arg Gln Asp Pro Glu Cys Glu Phe Tyr Phe Ser Leu Asp
            355                 360                 365

Ala Asp Ala Val Leu Thr Asn Leu Gln Thr Leu Arg Ile Leu Ile Glu
    370                 375                 380

Glu Asn Arg Lys Val Ile Ala Pro Met Leu Ser Arg His Gly Lys Leu
385                 390                 395                 400

Trp Ser Asn Phe Trp Gly Ala Leu Ser Pro Asp Glu Tyr Tyr Ala Arg
                405                 410                 415

Ser Glu Asp Tyr Val Glu Leu Val Gln Arg Lys Arg Val Gly Val Trp
            420                 425                 430

Asn Val Pro Tyr Ile Ser Gln Ala Tyr Val Ile Arg Gly Asp Thr Leu
        435                 440                 445

Arg Met Glu Leu Pro Gln Arg Asp Val Phe Ser Gly Ser Asp Thr Asp
    450                 455                 460

Pro Asp Met Ala Phe Cys Lys Ser Phe Arg Asp Lys Gly Ile Phe Leu
465                 470                 475                 480

His Leu Ser Asn Gln His Glu Phe Gly Arg Leu Leu Ala Thr Ser Arg
                485                 490                 495

Tyr Asp Thr Glu His Leu His Pro Asp Leu Trp Gln Ile Phe Asp Asn
            500                 505                 510

Pro Val Asp Trp Lys Glu Gln Tyr Ile His Glu Asn Tyr Ser Arg Ala
        515                 520                 525

Leu Glu Gly Glu Gly Ile Val Glu Gln Pro Cys Pro Asp Val Tyr Trp
    530                 535                 540

Phe Pro Leu Leu Ser Glu Gln Met Cys Asp Glu Leu Val Ala Glu Met
545                 550                 555                 560

Glu His Tyr Gly Gln Trp Ser Gly Gly Arg His Glu Asp Ser Arg Leu
                565                 570                 575

Ala Gly Gly Tyr Glu Asn Val Pro Thr Val Asp Ile His Met Lys Gln
            580                 585                 590

Val Gly Tyr Glu Asp Gln Trp Leu Gln Leu Leu Arg Thr Tyr Val Gly
        595                 600                 605

Pro Met Thr Glu Ser Leu Phe Pro Gly Tyr His Thr Lys Ala Arg Ala
    610                 615                 620

Val Met Asn Phe Val Val Arg Tyr Arg Pro Asp Glu Gln Pro Ser Leu
625                 630                 635                 640

Arg Pro His His Ala His Pro Pro Ser Pro Ser Thr Leu Pro Ser Thr
                645                 650                 655

Thr Arg Ala Trp Thr Met Arg Glu Val Ala Ala Ser Cys Ala Thr
            660                 665                 670

Thr Val

<210> SEQ ID NO 17
<211> LENGTH: 2745
<212> TYPE: DNA
<213> ORGANISM: Homo sapiens
<220> FEATURE:
<221> NAME/KEY: CDS
<222> LOCATION: (217)..(2433)

<400> SEQUENCE: 17
acaatcctcg ccttgtctgt ggcgccggca tctggagctt tctgtagcct ccggatacgc      60 cttttttttca gggcgtagcc cctagccaag ctgctccccg cggcggccgc acagcagccc    120
gagcgccccc tttccagagc tcccctccgg agctgggatc caggcgcgta gcggagatcc    180

```
caggatcctg ggtgctgttt gggcccgctc cccacc atg acc tcc tcg ggg cct        234
                                       Met Thr Ser Ser Gly Pro
                                         1               5 gga ccc cgg ttc ctg ctg ctg ccg ctg ctg ccc cct gcg gcc                282
Gly Pro Arg Phe Leu Leu Leu Pro Leu Leu Pro Pro Ala Ala
        10              15              20 tca gcc tcc gac cgg ccc cgg ggc cga gac ccg gtc aac cca gag aag        330
Ser Ala Ser Asp Arg Pro Arg Gly Arg Asp Pro Val Asn Pro Glu Lys
            25                  30                  35 ctg ctg gtg atc act gtg gcc aca gct gaa acc gag ggg tac ctg cgt        378
Leu Leu Val Ile Thr Val Ala Thr Ala Glu Thr Glu Gly Tyr Leu Arg
 40                  45                  50 ttc ctg cgc tct gcg gag ttc ttc aac tac act gtg cgg acc ctg ggc        426
Phe Leu Arg Ser Ala Glu Phe Phe Asn Tyr Thr Val Arg Thr Leu Gly
 55                  60                  65                  70 ctg gga gag gag tgg cga ggg ggt gat gtg gct cga aca gtt ggt gga        474
Leu Gly Glu Glu Trp Arg Gly Gly Asp Val Ala Arg Thr Val Gly Gly
                 75                  80                  85 gga cag aag gtc cgg tgg tta aag aag gaa atg gag aaa tac gct gac        522
Gly Gln Lys Val Arg Trp Leu Lys Lys Glu Met Glu Lys Tyr Ala Asp
             90                  95                 100 cgg gag gat atg atc atc atg ttt gtg gat agc tac gac gtg att ctg        570
Arg Glu Asp Met Ile Ile Met Phe Val Asp Ser Tyr Asp Val Ile Leu
        105                 110                 115 gcc ggc agc ccc aca gag ctg ctg aag aag ttc gtc cag agt ggc agc        618
Ala Gly Ser Pro Thr Glu Leu Leu Lys Lys Phe Val Gln Ser Gly Ser
120                 125                 130 cgc ctg ctc ttc tct gca gag agc ttc tgc tgg ccc gag tgg ggg ctg        666
Arg Leu Leu Phe Ser Ala Glu Ser Phe Cys Trp Pro Glu Trp Gly Leu
135                 140                 145                 150 gcg gag cag tac cct gag gtg ggc acg ggg aag cgc ttc ctc aat tct        714
Ala Glu Gln Tyr Pro Glu Val Gly Thr Gly Lys Arg Phe Leu Asn Ser
                155                 160                 165 ggt gga ttc atc ggt ttt gcc acc acc atc cac caa atc gtg cgc cag        762
Gly Gly Phe Ile Gly Phe Ala Thr Thr Ile His Gln Ile Val Arg Gln
            170                 175                 180 tgg aag tac aag gat gat gac gac gac cag ctg ttc tac aca cgg ctc        810
Trp Lys Tyr Lys Asp Asp Asp Asp Asp Gln Leu Phe Tyr Thr Arg Leu
        185                 190                 195 tac ctg gac cca gga ctg agg gag aaa ctc agc ctt aat ctg gat cat        858
Tyr Leu Asp Pro Gly Leu Arg Glu Lys Leu Ser Leu Asn Leu Asp His
200                 205                 210 aag tct cgg atc ttt cag aac ctc aac ggg gct tta gat gaa gtg gtt        906
Lys Ser Arg Ile Phe Gln Asn Leu Asn Gly Ala Leu Asp Glu Val Val
215                 220                 225                 230 tta aag ttt gat cgg aac cgt gtg cgt atc cgg aac gtg gcc tac gac        954
Leu Lys Phe Asp Arg Asn Arg Val Arg Ile Arg Asn Val Ala Tyr Asp
                235                 240                 245 acg ctc ccc att gtg gtc cat gga aac ggt ccc act aag ctg cag ctc       1002
Thr Leu Pro Ile Val Val His Gly Asn Gly Pro Thr Lys Leu Gln Leu
            250                 255                 260 aac tac ctg gga aac tac gtc ccc aat ggc tgg act cct gag gga ggc       1050
Asn Tyr Leu Gly Asn Tyr Val Pro Asn Gly Trp Thr Pro Glu Gly Gly
        265                 270                 275 tgt ggc ttc tgc aac cag gac cgg agg aca ctc ccg ggg ggg cag cct       1098
Cys Gly Phe Cys Asn Gln Asp Arg Arg Thr Leu Pro Gly Gly Gln Pro
280                 285                 290 ccc ccc cgg gtg ttt ctg gcc gtg ttt gtg gaa cag cct act ccg ttt       1146
Pro Pro Arg Val Phe Leu Ala Val Phe Val Glu Gln Pro Thr Pro Phe
295                 300                 305                 310
```

-continued

| | |
|---|---|
| ctg ccc cgc ttc ctg cag cgg ctg cta ctc ctg gac tat ccc ccc gac<br>Leu Pro Arg Phe Leu Gln Arg Leu Leu Leu Leu Asp Tyr Pro Pro Asp<br>315                   320                     325 | 1194 |
| agg gtc acc ctt ttc ctg cac aac aac gag gtc ttc cat gaa ccc cac<br>Arg Val Thr Leu Phe Leu His Asn Asn Glu Val Phe His Glu Pro His<br>          330                   335                 340 | 1242 |
| atc gct gac tcc tgg ccg cag ctc cag gac cac ttc tca gct gtg aag<br>Ile Ala Asp Ser Trp Pro Gln Leu Gln Asp His Phe Ser Ala Val Lys<br>                345                   350              355 | 1290 |
| ctc gtg ggg ccg gag gag gct ctg agc cca ggc gag gcc agg gac atg<br>Leu Val Gly Pro Glu Glu Ala Leu Ser Pro Gly Glu Ala Arg Asp Met<br>360                     365                     370 | 1338 |
| gcc atg gac ctg tgt cgg cag gac ccc gag tgt gag ttc tac ttc agc<br>Ala Met Asp Leu Cys Arg Gln Asp Pro Glu Cys Glu Phe Tyr Phe Ser<br>375                   380                   385              390 | 1386 |
| ctg gac gcc gac gct gtc ctc acc aac ctg cag acc ctg cgt atc ctc<br>Leu Asp Ala Asp Ala Val Leu Thr Asn Leu Gln Thr Leu Arg Ile Leu<br>                   395                   400              405 | 1434 |
| att gag gag aac agg aag gtg atc gcc ccc atg ctg tcc cgc cac ggc<br>Ile Glu Glu Asn Arg Lys Val Ile Ala Pro Met Leu Ser Arg His Gly<br>          410                   415                 420 | 1482 |
| aag ctg tgg tcc aac ttc tgg ggc gcc ctg agc ccc gat gag tac tac<br>Lys Leu Trp Ser Asn Phe Trp Gly Ala Leu Ser Pro Asp Glu Tyr Tyr<br>                425                   430              435 | 1530 |
| gcc cgc tcc gag gac tac gtg gag ctg gtg cag cgg aag cga gtg ggt<br>Ala Arg Ser Glu Asp Tyr Val Glu Leu Val Gln Arg Lys Arg Val Gly<br>440                     445                     450 | 1578 |
| gtg tgg aat gta cca tac atc tcc cag gcc tat gtg atc cgg ggt gat<br>Val Trp Asn Val Pro Tyr Ile Ser Gln Ala Tyr Val Ile Arg Gly Asp<br>455                   460                   465              470 | 1626 |
| acc ctg cgg atg gag ctg ccc cag agg gat gtg ttc tcg ggc agt gac<br>Thr Leu Arg Met Glu Leu Pro Gln Arg Asp Val Phe Ser Gly Ser Asp<br>                475                   480              485 | 1674 |
| aca gac ccg gac atg gcc ttc tgt aag agc ttt cga gac aag ggc atc<br>Thr Asp Pro Asp Met Ala Phe Cys Lys Ser Phe Arg Asp Lys Gly Ile<br>          490                   495                 500 | 1722 |
| ttc ctc cat ctg agc aat cag cat gaa ttt ggc cgg ctc ctg gcc act<br>Phe Leu His Leu Ser Asn Gln His Glu Phe Gly Arg Leu Leu Ala Thr<br>                505                   510              515 | 1770 |
| tcc aga tac gac acg gag cac ctg cac ccc gac ctc tgg cag atc ttc<br>Ser Arg Tyr Asp Thr Glu His Leu His Pro Asp Leu Trp Gln Ile Phe<br>520                     525                     530 | 1818 |
| gac aac ccc gtc gac tgg aag gag cag tac atc cac gag aac tac agc<br>Asp Asn Pro Val Asp Trp Lys Glu Gln Tyr Ile His Glu Asn Tyr Ser<br>535                   540                   545              550 | 1866 |
| cgg gcc ctg gaa ggg gaa gga atc gtg gag cag cca tgc ccg gac gtg<br>Arg Ala Leu Glu Gly Glu Gly Ile Val Glu Gln Pro Cys Pro Asp Val<br>                555                   560              565 | 1914 |
| tac tgg ttc cca ctg ctg tca gaa caa atg tgt gat gag ctg gtg gca<br>Tyr Trp Phe Pro Leu Leu Ser Glu Gln Met Cys Asp Glu Leu Val Ala<br>                   570                   575              580 | 1962 |
| gag atg gag cac tac ggc cag tgg tca ggc ggc cgg cat gag gat tca<br>Glu Met Glu His Tyr Gly Gln Trp Ser Gly Gly Arg His Glu Asp Ser<br>585                     590                   595 | 2010 |
| agg ctg gct gga ggc tac gag aat gtg ccc acc gtg gac atc cac atg<br>Arg Leu Ala Gly Gly Tyr Glu Asn Val Pro Thr Val Asp Ile His Met<br>600                     605                   610 | 2058 |
| aag cag gtg ggg tac gag gac cag tgg ctg cag ctg ctg cgg acg tat<br>Lys Gln Val Gly Tyr Glu Asp Gln Trp Leu Gln Leu Leu Arg Thr Tyr | 2106 |

-continued

```
          615                 620                 625                 630
gtg ggc ccc atg acc gag agc ctg ttt ccc ggt tac cac acc aag gcg         2154
Val Gly Pro Met Thr Glu Ser Leu Phe Pro Gly Tyr His Thr Lys Ala
                    635                 640                 645 cgg gcg gtg atg aac ttt gtg gtt cgc tac cgg cca gac gag cag ccg         2202
Arg Ala Val Met Asn Phe Val Val Arg Tyr Arg Pro Asp Glu Gln Pro
                650                 655                 660 tct ctg cgg cca cac cac gac tca tcc acc ttc acc ctc aac gtt gcc         2250
Ser Leu Arg Pro His His Asp Ser Ser Thr Phe Thr Leu Asn Val Ala
            665                 670                 675 ctc aac cac aag ggc ctg gac tat gag gga ggt ggc tgc cgc ttc ctg         2298
Leu Asn His Lys Gly Leu Asp Tyr Glu Gly Gly Gly Cys Arg Phe Leu
        680                 685                 690 cgc tac gac tgt gtg atc tcc tcc ccg agg aag ggc tgg gca ctc ctg         2346
Arg Tyr Asp Cys Val Ile Ser Ser Pro Arg Lys Gly Trp Ala Leu Leu
695                 700                 705                 710 cac ccc ggc cgc ctc acc cac tac cac gag ggg ctg cca acg acc tgg         2394
His Pro Gly Arg Leu Thr His Tyr His Glu Gly Leu Pro Thr Thr Trp
                    715                 720                 725 ggc aca cgc tac atc atg gtg tcc ttt gtc gac ccc tga cactcaacca         2443
Gly Thr Arg Tyr Ile Met Val Ser Phe Val Asp Pro
                730                 735 ctctgccaaa cctgccctgc cattgtgcct ttttaggggg cctggccccc gtcctgggag      2503
ttgggggatg ggtctctctg tctccccact tcctgagttc atgttccgcg tgcctgaact      2563
gaatatgtca ccttgctccc aagacacggc cctctcagga agctcccgga gtccccgcct     2623
ctctcctccg cccacagggg ttcgtgggca cagggcttct ggggactccc cgcgtgataa     2683
attattaatg ttccgcagtc tcactctgaa taaaggacag tttgtaaatc ttaaaaaaaa     2743
aa                                                                     2745
```

<210> SEQ ID NO 18
<211> LENGTH: 738
<212> TYPE: PRT
<213> ORGANISM: Homo sapiens

<400> SEQUENCE: 18

```
Met Thr Ser Ser Gly Pro Gly Pro Arg Phe Leu Leu Leu Pro Leu
1               5                   10                  15

Leu Leu Pro Pro Ala Ser Ala Ser Asp Arg Pro Arg Gly Arg Asp
                20                  25                  30

Pro Val Asn Pro Glu Lys Leu Leu Val Ile Thr Val Ala Thr Ala Glu
            35                  40                  45

Thr Glu Gly Tyr Leu Arg Phe Leu Arg Ser Ala Glu Phe Phe Asn Tyr
        50                  55                  60

Thr Val Arg Thr Leu Gly Leu Gly Glu Glu Trp Arg Gly Gly Asp Val
65                  70                  75                  80

Ala Arg Thr Val Gly Gly Gly Gln Lys Val Arg Trp Leu Lys Lys Glu
                85                  90                  95

Met Glu Lys Tyr Ala Asp Arg Glu Asp Met Ile Ile Met Phe Val Asp
                100                 105                 110

Ser Tyr Asp Val Ile Leu Ala Gly Ser Pro Thr Glu Leu Leu Lys Lys
            115                 120                 125

Phe Val Gln Ser Gly Ser Arg Leu Leu Phe Ser Ala Glu Ser Phe Cys
        130                 135                 140

Trp Pro Glu Trp Gly Leu Ala Glu Gln Tyr Pro Glu Val Gly Thr Gly
145                 150                 155                 160
```

```
Lys Arg Phe Leu Asn Ser Gly Gly Phe Ile Gly Phe Ala Thr Thr Ile
                165                 170                 175

His Gln Ile Val Arg Gln Trp Lys Tyr Lys Asp Asp Asp Asp Gln
            180                 185                 190

Leu Phe Tyr Thr Arg Leu Tyr Leu Asp Pro Gly Leu Arg Glu Lys Leu
            195                 200             205

Ser Leu Asn Leu Asp His Lys Ser Arg Ile Phe Gln Asn Leu Asn Gly
    210                 215                 220

Ala Leu Asp Glu Val Val Leu Lys Phe Asp Arg Asn Arg Val Arg Ile
225                 230                 235                 240

Arg Asn Val Ala Tyr Asp Thr Leu Pro Ile Val His Gly Asn Gly
                245                 250                 255

Pro Thr Lys Leu Gln Leu Asn Tyr Leu Gly Asn Tyr Val Pro Asn Gly
                260                 265                 270

Trp Thr Pro Glu Gly Gly Cys Gly Phe Cys Asn Gln Asp Arg Arg Thr
            275                 280                 285

Leu Pro Gly Gly Gln Pro Pro Arg Val Phe Leu Ala Val Phe Val
    290                 295                 300

Glu Gln Pro Thr Pro Phe Leu Pro Arg Phe Leu Gln Arg Leu Leu Leu
305                 310                 315                 320

Leu Asp Tyr Pro Pro Asp Arg Val Thr Leu Phe Leu His Asn Asn Glu
                325                 330                 335

Val Phe His Glu Pro His Ile Ala Asp Ser Trp Pro Gln Leu Gln Asp
            340                 345                 350

His Phe Ser Ala Val Lys Leu Val Gly Pro Glu Glu Ala Leu Ser Pro
            355                 360                 365

Gly Glu Ala Arg Asp Met Ala Met Asp Leu Cys Arg Gln Asp Pro Glu
            370                 375                 380

Cys Glu Phe Tyr Phe Ser Leu Asp Ala Asp Ala Val Leu Thr Asn Leu
385                 390                 395                 400

Gln Thr Leu Arg Ile Leu Ile Glu Glu Asn Arg Lys Val Ile Ala Pro
                405                 410                 415

Met Leu Ser Arg His Gly Lys Leu Trp Ser Asn Phe Trp Gly Ala Leu
            420                 425                 430

Ser Pro Asp Glu Tyr Tyr Ala Arg Ser Glu Asp Tyr Val Glu Leu Val
        435                 440                 445

Gln Arg Lys Arg Val Gly Val Trp Asn Val Pro Tyr Ile Ser Gln Ala
    450                 455                 460

Tyr Val Ile Arg Gly Asp Thr Leu Arg Met Glu Leu Pro Gln Arg Asp
465                 470                 475                 480

Val Phe Ser Gly Ser Asp Thr Asp Pro Asp Met Ala Phe Cys Lys Ser
                485                 490                 495

Phe Arg Asp Lys Gly Ile Phe Leu His Leu Ser Asn Gln His Glu Phe
            500                 505                 510

Gly Arg Leu Leu Ala Thr Ser Arg Tyr Asp Thr Glu His Leu His Pro
        515                 520                 525

Asp Leu Trp Gln Ile Phe Asp Asn Pro Val Asp Trp Lys Glu Gln Tyr
    530                 535                 540

Ile His Glu Asn Tyr Ser Arg Ala Leu Glu Gly Glu Gly Ile Val Glu
545                 550                 555                 560

Gln Pro Cys Pro Asp Val Tyr Trp Phe Pro Leu Leu Ser Glu Gln Met
                565                 570                 575
```

```
Cys Asp Glu Leu Val Ala Glu Met Glu His Tyr Gly Gln Trp Ser Gly
            580                 585                 590

Gly Arg His Glu Asp Ser Arg Leu Ala Gly Gly Tyr Glu Asn Val Pro
            595                 600                 605

Thr Val Asp Ile His Met Lys Gln Val Gly Tyr Glu Asp Gln Trp Leu
        610                 615                 620

Gln Leu Leu Arg Thr Tyr Val Gly Pro Met Thr Glu Ser Leu Phe Pro
625                 630                 635                 640

Gly Tyr His Thr Lys Ala Arg Ala Val Met Asn Phe Val Val Arg Tyr
                645                 650                 655

Arg Pro Asp Glu Gln Pro Ser Leu Arg Pro His His Asp Ser Ser Thr
                    660                 665                 670

Phe Thr Leu Asn Val Ala Leu Asn His Lys Gly Leu Asp Tyr Glu Gly
            675                 680                 685

Gly Gly Cys Arg Phe Leu Arg Tyr Asp Cys Val Ile Ser Ser Pro Arg
        690                 695                 700

Lys Gly Trp Ala Leu Leu His Pro Gly Arg Leu Thr His Tyr His Glu
705                 710                 715                 720

Gly Leu Pro Thr Thr Trp Gly Thr Arg Tyr Ile Met Val Ser Phe Val
                725                 730                 735

Asp Pro

<210> SEQ ID NO 19
<211> LENGTH: 258
<212> TYPE: DNA
<213> ORGANISM: Homo sapiens
<220> FEATURE:
<221> NAME/KEY: CDS
<222> LOCATION: (1)..(258)

<400> SEQUENCE: 19 aat ggc tgg act cct gag gga ggc tgt ggc ttc tgc aac cag gac cgg     48
Asn Gly Trp Thr Pro Glu Gly Gly Cys Gly Phe Cys Asn Gln Asp Arg
 1               5                  10                  15 agg aca ctc ccg ggg ggg cag cct ccc ccc cgg gtg ttt ctg gcc gtg     96
Arg Thr Leu Pro Gly Gly Gln Pro Pro Pro Arg Val Phe Leu Ala Val
             20                  25                  30 ttt gtg gaa cag cct act ccg ttt ctg ccc cgc ttc ctg cag cgg ctg    144
Phe Val Glu Gln Pro Thr Pro Phe Leu Pro Arg Phe Leu Gln Arg Leu
         35                  40                  45 cta ctc ctg gac tat ccc ccc gac agg gtc acc ctt ttc ctg cac aac    192
Leu Leu Leu Asp Tyr Pro Pro Asp Arg Val Thr Leu Phe Leu His Asn
     50                  55                  60 aac gag gtc ttc cat gaa ccc cac atc gct gac tcc tgg ccg cag ctc    240
Asn Glu Val Phe His Glu Pro His Ile Ala Asp Ser Trp Pro Gln Leu
 65                  70                  75                  80 cag gac cac ttc tca gct                                            258
Gln Asp His Phe Ser Ala
                 85

<210> SEQ ID NO 20
<211> LENGTH: 86
<212> TYPE: PRT
<213> ORGANISM: Homo sapiens

<400> SEQUENCE: 20

Asn Gly Trp Thr Pro Glu Gly Gly Cys Gly Phe Cys Asn Gln Asp Arg
 1               5                  10                  15

Arg Thr Leu Pro Gly Gly Gln Pro Pro Pro Arg Val Phe Leu Ala Val
```

-continued

```
                    20                  25                  30
Phe Val Glu Gln Pro Thr Pro Phe Leu Pro Arg Phe Leu Gln Arg Leu
            35                  40                  45

Leu Leu Leu Asp Tyr Pro Pro Asp Arg Val Thr Leu Phe Leu His Asn
        50                  55                  60

Asn Glu Val Phe His Glu Pro His Ile Ala Asp Ser Trp Pro Gln Leu
65                  70                  75                  80

Gln Asp His Phe Ser Ala
                85

<210> SEQ ID NO 21
<211> LENGTH: 2184
<212> TYPE: DNA
<213> ORGANISM: Homo sapiens
<220> FEATURE:
<221> NAME/KEY: CDS
<222> LOCATION: (1)..(2184)

<400> SEQUENCE: 21 atg cgg ccc ctg ctg cta ctg gcc ctg ctg ggc tgg ctg ctg ctg gcc    48
Met Arg Pro Leu Leu Leu Leu Ala Leu Leu Gly Trp Leu Leu Leu Ala
1               5                   10                  15 gaa gcg aag ggc gac gcc aag ccg gag gac aac ctt tta gtc ctc acg    96
Glu Ala Lys Gly Asp Ala Lys Pro Glu Asp Asn Leu Leu Val Leu Thr
            20                  25                  30 gtg gcc act aag gag acc gag gga ttc cgt cgc ttc aag cgc tca gct   144
Val Ala Thr Lys Glu Thr Glu Gly Phe Arg Arg Phe Lys Arg Ser Ala
        35                  40                  45 cag ttc ttc aac tac aag atc cag gcg ctt ggc cta ggg gag gac tgg   192
Gln Phe Phe Asn Tyr Lys Ile Gln Ala Leu Gly Leu Gly Glu Asp Trp
    50                  55                  60 aat gtg gag aag ggg acg tcg gca ggt gga ggg cag aag gtc cgg ctg   240
Asn Val Glu Lys Gly Thr Ser Ala Gly Gly Gly Gln Lys Val Arg Leu
65                  70                  75                  80 ctg aag aaa gct ctg gag aag cac gca gac aag gag gat ctg gtc att   288
Leu Lys Lys Ala Leu Glu Lys His Ala Asp Lys Glu Asp Leu Val Ile
            85                  90                  95 ctc ttc aca gac agc tat gac gtg ctg ttt gca tcg ggg ccc cgg gag   336
Leu Phe Thr Asp Ser Tyr Asp Val Leu Phe Ala Ser Gly Pro Arg Glu
        100                 105                 110 ctc ctg aag aag ttc cgg cag gcc agg agc cag gtg gtc ttc tct gct   384
Leu Leu Lys Lys Phe Arg Gln Ala Arg Ser Gln Val Val Phe Ser Ala
    115                 120                 125 gag gag ctc atc tac cca gac cgc agg ctg gag acc aag tat ccg gtg   432
Glu Glu Leu Ile Tyr Pro Asp Arg Arg Leu Glu Thr Lys Tyr Pro Val
130                 135                 140 gtg tcc gat ggc aag agg ttc ctg ggc tct gga ggc ttc atc ggt tat   480
Val Ser Asp Gly Lys Arg Phe Leu Gly Ser Gly Gly Phe Ile Gly Tyr
145                 150                 155                 160 gcc ccc aac ctc agc aaa ctg gtg gcc gag tgg gag ggc cag gac agc   528
Ala Pro Asn Leu Ser Lys Leu Val Ala Glu Trp Glu Gly Gln Asp Ser
                165                 170                 175 gac agc gat cag ctg ttt tac acc aag atc ttc ttg gac ccg gag aag   576
Asp Ser Asp Gln Leu Phe Tyr Thr Lys Ile Phe Leu Asp Pro Glu Lys
            180                 185                 190 agg gag cag atc aat atc acc ctg gac cac cgc tgc cgt atc ttc cag   624
Arg Glu Gln Ile Asn Ile Thr Leu Asp His Arg Cys Arg Ile Phe Gln
        195                 200                 205 aac ctg gat gga gcc ttg gat gag gtc gtg ctc aag ttt gaa atg ggc   672
Asn Leu Asp Gly Ala Leu Asp Glu Val Val Leu Lys Phe Glu Met Gly
```

-continued

```
           210                 215                 220
cat gtg aga gcg agg aac ctg gcc tat gac acc ctc ccg gtc ctg atc       720
His Val Arg Ala Arg Asn Leu Ala Tyr Asp Thr Leu Pro Val Leu Ile
225                 230                 235                 240 cat ggc aac ggg cca acc aag ctg cag ttg aac tac ctg ggc aac tac       768
His Gly Asn Gly Pro Thr Lys Leu Gln Leu Asn Tyr Leu Gly Asn Tyr
                    245                 250                 255 atc ccg cgc ttc tgg acc ttc gaa aca ggc tgc acc gtg tgt gac gaa       816
Ile Pro Arg Phe Trp Thr Phe Glu Thr Gly Cys Thr Val Cys Asp Glu
            260                 265                 270 ggc ttg cgc agc ctc aag ggc att ggg gat gaa gct ctg ccc acg gtc       864
Gly Leu Arg Ser Leu Lys Gly Ile Gly Asp Glu Ala Leu Pro Thr Val
        275                 280                 285 ctg gtc ggc gtg ttc atc gaa cag ccc acg ccg ttt gtg tcc ctg ttc       912
Leu Val Gly Val Phe Ile Glu Gln Pro Thr Pro Phe Val Ser Leu Phe
    290                 295                 300 ttc cag cgg ctc ctg cgg ctc cac tac ccc cag aaa cac atg cga ctt       960
Phe Gln Arg Leu Leu Arg Leu His Tyr Pro Gln Lys His Met Arg Leu
305                 310                 315                 320 ttc atc cac aac cac gag cag cac cac aag gct cag gtg gaa gag ttc      1008
Phe Ile His Asn His Glu Gln His His Lys Ala Gln Val Glu Glu Phe
                    325                 330                 335 ctg gca cag cat ggc agc gag tac cag tct gtg aag ctg gtg ggc cct      1056
Leu Ala Gln His Gly Ser Glu Tyr Gln Ser Val Lys Leu Val Gly Pro
            340                 345                 350 gag gtg cgg atg gcg aat gca gat gcc agg aac atg ggc gca gac ctg      1104
Glu Val Arg Met Ala Asn Ala Asp Ala Arg Asn Met Gly Ala Asp Leu
        355                 360                 365 tgc cgg cag gac cgc agc tgc acc tac tac ttc agc gtg gat gct gac      1152
Cys Arg Gln Asp Arg Ser Cys Thr Tyr Tyr Phe Ser Val Asp Ala Asp
    370                 375                 380 gtg gcc ctg acc gag ccc aac agc ctg cgg ctg ctg atc caa cag aac      1200
Val Ala Leu Thr Glu Pro Asn Ser Leu Arg Leu Leu Ile Gln Gln Asn
385                 390                 395                 400 aag aat gtc att gcc ccg ctg atg acc cgg cat ggg agg ctg tgg tcg      1248
Lys Asn Val Ile Ala Pro Leu Met Thr Arg His Gly Arg Leu Trp Ser
                    405                 410                 415 aac ttc tgg ggg gct ctc agt gca gat ggc tac tat gcc cgt tcc gag      1296
Asn Phe Trp Gly Ala Leu Ser Ala Asp Gly Tyr Tyr Ala Arg Ser Glu
            420                 425                 430 gac tac gtg gac att gtg cag ggg cgg cgt gtt ggt gtc tgg aat gtg      1344
Asp Tyr Val Asp Ile Val Gln Gly Arg Arg Val Gly Val Trp Asn Val
        435                 440                 445 ccc tat att tca aac atc tac ttg atc aag ggc agt gcc ctg cgg ggt      1392
Pro Tyr Ile Ser Asn Ile Tyr Leu Ile Lys Gly Ser Ala Leu Arg Gly
    450                 455                 460 gag ctg cag tcc tca gat ctc ttc cac cac agc aag ctg gac ccc gac      1440
Glu Leu Gln Ser Ser Asp Leu Phe His His Ser Lys Leu Asp Pro Asp
465                 470                 475                 480 atg gcc ttc tgt gcc aac atc cgg cag cag gat gtg ttc atg ttc ctg      1488
Met Ala Phe Cys Ala Asn Ile Arg Gln Gln Asp Val Phe Met Phe Leu
                    485                 490                 495 acc aac cgg cac acc ctt ggc cat ctg ctc tcc cta gac agc tac cgc      1536
Thr Asn Arg His Thr Leu Gly His Leu Leu Ser Leu Asp Ser Tyr Arg
            500                 505                 510 acc acc cac ctg cac aac gac ctc tgg gag gtg ttc agc aac ccc gag      1584
Thr Thr His Leu His Asn Asp Leu Trp Glu Val Phe Ser Asn Pro Glu
        515                 520                 525 gac tgg aag gag aag tac atc cac cag aac tac acc aaa gcc ctg gca      1632
Asp Trp Lys Glu Lys Tyr Ile His Gln Asn Tyr Thr Lys Ala Leu Ala
```

```
Asp Trp Lys Glu Lys Tyr Ile His Gln Asn Tyr Thr Lys Ala Leu Ala
            530                 535                 540 ggg aag ctg gtg gag acg ccc tgc ccg gat gtc tat tgg ttc ccc atc        1680
Gly Lys Leu Val Glu Thr Pro Cys Pro Asp Val Tyr Trp Phe Pro Ile
545                 550                 555                 560 ttc acg gag gtg gcc tgt gat gag ctg gtg gag gag atg gag cac ttt        1728
Phe Thr Glu Val Ala Cys Asp Glu Leu Val Glu Glu Met Glu His Phe
                565                 570                 575 ggc cag tgg tct ctg ggc aac aac aag gac aac cgc atc cag ggt ggc        1776
Gly Gln Trp Ser Leu Gly Asn Asn Lys Asp Asn Arg Ile Gln Gly Gly
            580                 585                 590 tac gag aac gtg ccg act att gac atc cac atg aac cag atc ggc ttt        1824
Tyr Glu Asn Val Pro Thr Ile Asp Ile His Met Asn Gln Ile Gly Phe
        595                 600                 605 gag cgg gag tgg cac aaa ttc ctg ctg gag tac att gcg ccc atg acg        1872
Glu Arg Glu Trp His Lys Phe Leu Leu Glu Tyr Ile Ala Pro Met Thr
    610                 615                 620 gag aag ctc tac ccc ggc tac tac acc agg gcc cag ttt gac ctg gcc        1920
Glu Lys Leu Tyr Pro Gly Tyr Tyr Thr Arg Ala Gln Phe Asp Leu Ala
625                 630                 635                 640 ttt gtc gtc cgc tac aag cct gat gag cag ccc tca ctg atg cca cac        1968
Phe Val Val Arg Tyr Lys Pro Asp Glu Gln Pro Ser Leu Met Pro His
                645                 650                 655 cat gat gcc tcc acc ttc acc atc aac atc gcc ctg aac cga gtc ggg        2016
His Asp Ala Ser Thr Phe Thr Ile Asn Ile Ala Leu Asn Arg Val Gly
            660                 665                 670 gtg gat tac gag ggc ggg ggc tgt cgg ttc ctg cgc tac aac tgt tcc        2064
Val Asp Tyr Glu Gly Gly Gly Cys Arg Phe Leu Arg Tyr Asn Cys Ser
        675                 680                 685 atc cga gcc cca agg aag ggc tgg acc ctc atg cac cct gga cga ctc        2112
Ile Arg Ala Pro Arg Lys Gly Trp Thr Leu Met His Pro Gly Arg Leu
    690                 695                 700 acg cat tac cat gag ggg ctc ccc acc acc agg ggc acc cgc tac atc        2160
Thr His Tyr His Glu Gly Leu Pro Thr Thr Arg Gly Thr Arg Tyr Ile
705                 710                 715                 720 gca gtc tcc ttc gtc gat ccc taa                                        2184
Ala Val Ser Phe Val Asp Pro
                725

<210> SEQ ID NO 22
<211> LENGTH: 727
<212> TYPE: PRT
<213> ORGANISM: Homo sapiens

<400> SEQUENCE: 22

Met Arg Pro Leu Leu Leu Leu Ala Leu Leu Gly Trp Leu Leu Leu Ala
1               5                   10                  15

Glu Ala Lys Gly Asp Ala Lys Pro Glu Asp Asn Leu Leu Val Leu Thr
            20                  25                  30

Val Ala Thr Lys Glu Thr Glu Gly Phe Arg Arg Phe Lys Arg Ser Ala
        35                  40                  45

Gln Phe Phe Asn Tyr Lys Ile Gln Ala Leu Gly Leu Gly Glu Asp Trp
    50                  55                  60

Asn Val Glu Lys Gly Thr Ser Ala Gly Gly Gln Lys Val Arg Leu Leu
65                  70                  75                  80

Leu Lys Lys Ala Leu Glu Lys His Ala Asp Lys Glu Asp Leu Val Ile
                85                  90                  95

Leu Phe Thr Asp Ser Tyr Asp Val Leu Phe Ala Ser Gly Pro Arg Glu
            100                 105                 110
```

-continued

```
Leu Leu Lys Lys Phe Arg Gln Ala Arg Ser Gln Val Val Phe Ser Ala
        115                 120                 125

Glu Glu Leu Ile Tyr Pro Asp Arg Arg Leu Glu Thr Lys Tyr Pro Val
130                 135                 140

Val Ser Asp Gly Lys Arg Phe Leu Gly Ser Gly Phe Ile Gly Tyr
145                 150                 155                 160

Ala Pro Asn Leu Ser Lys Leu Val Ala Glu Trp Glu Gly Gln Asp Ser
                165                 170                 175

Asp Ser Asp Gln Leu Phe Tyr Thr Lys Ile Phe Leu Asp Pro Glu Lys
            180                 185                 190

Arg Glu Gln Ile Asn Ile Thr Leu Asp His Arg Cys Arg Ile Phe Gln
        195                 200                 205

Asn Leu Asp Gly Ala Leu Asp Glu Val Val Leu Lys Phe Glu Met Gly
    210                 215                 220

His Val Arg Ala Arg Asn Leu Ala Tyr Asp Thr Leu Pro Val Leu Ile
225                 230                 235                 240

His Gly Asn Gly Pro Thr Lys Leu Gln Leu Asn Tyr Leu Gly Asn Tyr
                245                 250                 255

Ile Pro Arg Phe Trp Thr Phe Glu Thr Gly Cys Thr Val Cys Asp Glu
            260                 265                 270

Gly Leu Arg Ser Leu Lys Gly Ile Gly Asp Glu Ala Leu Pro Thr Val
        275                 280                 285

Leu Val Gly Val Phe Ile Glu Gln Pro Thr Pro Phe Val Ser Leu Phe
    290                 295                 300

Phe Gln Arg Leu Leu Arg Leu His Tyr Pro Gln Lys His Met Arg Leu
305                 310                 315                 320

Phe Ile His Asn His Glu Gln His His Lys Ala Gln Val Glu Glu Phe
                325                 330                 335

Leu Ala Gln His Gly Ser Glu Tyr Gln Ser Val Lys Leu Val Gly Pro
            340                 345                 350

Glu Val Arg Met Ala Asn Ala Asp Ala Arg Asn Met Gly Ala Asp Leu
        355                 360                 365

Cys Arg Gln Asp Arg Ser Cys Thr Tyr Tyr Phe Ser Val Asp Ala Asp
370                 375                 380

Val Ala Leu Thr Glu Pro Asn Ser Leu Arg Leu Leu Ile Gln Gln Asn
385                 390                 395                 400

Lys Asn Val Ile Ala Pro Leu Met Thr Arg His Gly Arg Leu Trp Ser
                405                 410                 415

Asn Phe Trp Gly Ala Leu Ser Ala Asp Gly Tyr Tyr Ala Arg Ser Glu
            420                 425                 430

Asp Tyr Val Asp Ile Val Gln Gly Arg Arg Val Gly Val Trp Asn Val
        435                 440                 445

Pro Tyr Ile Ser Asn Ile Tyr Leu Ile Lys Gly Ser Ala Leu Arg Gly
    450                 455                 460

Glu Leu Gln Ser Ser Asp Leu Phe His His Ser Lys Leu Asp Pro Asp
465                 470                 475                 480

Met Ala Phe Cys Ala Asn Ile Arg Gln Gln Asp Val Phe Met Phe Leu
                485                 490                 495

Thr Asn Arg His Thr Leu Gly His Leu Leu Ser Leu Asp Ser Tyr Arg
            500                 505                 510

Thr Thr His Leu His Asn Asp Leu Trp Glu Val Phe Ser Asn Pro Glu
        515                 520                 525
```

```
Asp Trp Lys Glu Lys Tyr Ile His Gln Asn Tyr Thr Lys Ala Leu Ala
    530                 535                 540

Gly Lys Leu Val Glu Thr Pro Cys Pro Asp Val Tyr Trp Phe Pro Ile
545                 550                 555                 560

Phe Thr Glu Val Ala Cys Asp Glu Leu Val Glu Glu Met Glu His Phe
                565                 570                 575

Gly Gln Trp Ser Leu Gly Asn Asn Lys Asp Asn Arg Ile Gln Gly Gly
            580                 585                 590

Tyr Glu Asn Val Pro Thr Ile Asp Ile His Met Asn Gln Ile Gly Phe
        595                 600                 605

Glu Arg Glu Trp His Lys Phe Leu Leu Glu Tyr Ile Ala Pro Met Thr
    610                 615                 620

Glu Lys Leu Tyr Pro Gly Tyr Tyr Thr Arg Ala Gln Phe Asp Leu Ala
625                 630                 635                 640

Phe Val Val Arg Tyr Lys Pro Asp Glu Gln Pro Ser Leu Met Pro His
                645                 650                 655

His Asp Ala Ser Thr Phe Thr Ile Asn Ile Ala Leu Asn Arg Val Gly
            660                 665                 670

Val Asp Tyr Glu Gly Gly Gly Cys Arg Phe Leu Arg Tyr Asn Cys Ser
        675                 680                 685

Ile Arg Ala Pro Arg Lys Gly Trp Thr Leu Met His Pro Gly Arg Leu
    690                 695                 700

Thr His Tyr His Glu Gly Leu Pro Thr Thr Arg Gly Thr Arg Tyr Ile
705                 710                 715                 720

Ala Val Ser Phe Val Asp Pro
                725

<210> SEQ ID NO 23
<211> LENGTH: 3503
<212> TYPE: DNA
<213> ORGANISM: Homo sapiens
<220> FEATURE:
<221> NAME/KEY: CDS
<222> LOCATION: (1)..(2211)

<400> SEQUENCE: 23 atg ggg gga tgc acg gtg aag cct cag ctg ctg ctc ctg gcg ctc gtc      48
Met Gly Gly Cys Thr Val Lys Pro Gln Leu Leu Leu Leu Ala Leu Val
1               5                   10                  15 ctc cac ccc tgg aat ccc tgt ctg ggt gcg gac tcg gag aag ccc tcg      96
Leu His Pro Trp Asn Pro Cys Leu Gly Ala Asp Ser Glu Lys Pro Ser
                20                  25                  30 agc atc ccc aca gat aaa tta tta gtc ata act gta gca aca aaa gaa     144
Ser Ile Pro Thr Asp Lys Leu Leu Val Ile Thr Val Ala Thr Lys Glu
            35                  40                  45 agt gat gga ttc cat cga ttt atg cag tca gcc aaa tat ttc aat tat     192
Ser Asp Gly Phe His Arg Phe Met Gln Ser Ala Lys Tyr Phe Asn Tyr
        50                  55                  60 act gtg aag gtc ctt ggt caa gga gaa gaa tgg aga ggt ggt gat gga     240
Thr Val Lys Val Leu Gly Gln Gly Glu Glu Trp Arg Gly Gly Asp Gly
65                  70                  75                  80 att aat agt att gga ggg ggc cag aaa gtg aga tta atg aaa gaa gtc     288
Ile Asn Ser Ile Gly Gly Gly Gln Lys Val Arg Leu Met Lys Glu Val
                85                  90                  95 atg gaa cac tat gct gat caa gat gat ctg gtt gtc atg ttt act gaa     336
Met Glu His Tyr Ala Asp Gln Asp Asp Leu Val Val Met Phe Thr Glu
                100                 105                 110 tgc ttt gat gtc ata ttt gct ggt ggt cca gaa gaa gtt cta aaa aaa     384
```

```
              Cys Phe Asp Val Ile Phe Ala Gly Gly Pro Glu Glu Val Leu Lys Lys
                      115                 120                 125 ttc caa aag gca aac cac aaa gtg gtc ttt gca gca gat gga att ttg            432
Phe Gln Lys Ala Asn His Lys Val Val Phe Ala Ala Asp Gly Ile Leu
    130                 135                 140 tgg cca gat aaa aga cta gca gac aag tat cct gtt gtg cac att ggg            480
Trp Pro Asp Lys Arg Leu Ala Asp Lys Tyr Pro Val Val His Ile Gly
145                 150                 155                 160 aaa cgc tat ctg aat tca gga gga ttt att ggc tat gct cca tat gtc            528
Lys Arg Tyr Leu Asn Ser Gly Gly Phe Ile Gly Tyr Ala Pro Tyr Val
                165                 170                 175 aac cgt ata gtt caa caa tgg aat ctc cag gat aat gat gat gat cag            576
Asn Arg Ile Val Gln Gln Trp Asn Leu Gln Asp Asn Asp Asp Asp Gln
            180                 185                 190 ctc ttt tac act aaa gtt tac att gat cca ctg aaa agg gaa gct att            624
Leu Phe Tyr Thr Lys Val Tyr Ile Asp Pro Leu Lys Arg Glu Ala Ile
        195                 200                 205 aac atc aca ttg gat cac aaa tgc aaa att ttc cag acc tta aat gga            672
Asn Ile Thr Leu Asp His Lys Cys Lys Ile Phe Gln Thr Leu Asn Gly
    210                 215                 220 gct gta gat gaa gtt gtt tta aaa ttt gaa aat ggc aaa gcc aga gct            720
Ala Val Asp Glu Val Val Leu Lys Phe Glu Asn Gly Lys Ala Arg Ala
225                 230                 235                 240 aag aat aca ttt tat gaa aca tta cca gtg gca att aat gga aat gga            768
Lys Asn Thr Phe Tyr Glu Thr Leu Pro Val Ala Ile Asn Gly Asn Gly
                245                 250                 255 ccc acc aag att ctc ctg aat tat ttt gga aac tat gta ccc aat tca            816
Pro Thr Lys Ile Leu Leu Asn Tyr Phe Gly Asn Tyr Val Pro Asn Ser
            260                 265                 270 tgg aca cag gat aat ggc tgc act ctt tgt gaa ttc gat aca gtc gac            864
Trp Thr Gln Asp Asn Gly Cys Thr Leu Cys Glu Phe Asp Thr Val Asp
        275                 280                 285 ttg tct gca gta gat gtc cat cca aac gta tca ata ggt gtt ttt att            912
Leu Ser Ala Val Asp Val His Pro Asn Val Ser Ile Gly Val Phe Ile
    290                 295                 300 gag caa cca acc cct ttt cta cct cgg ttt ctg gac ata ttg ttg aca            960
Glu Gln Pro Thr Pro Phe Leu Pro Arg Phe Leu Asp Ile Leu Leu Thr
305                 310                 315                 320 ctg gat tac cca aaa gaa gca ctt aaa ctt ttt att cat aac aaa gaa           1008
Leu Asp Tyr Pro Lys Glu Ala Leu Lys Leu Phe Ile His Asn Lys Glu
                325                 330                 335 gtt tat cat gaa aag gac atc aag gta ttt ttt gat aaa gct aag cat           1056
Val Tyr His Glu Lys Asp Ile Lys Val Phe Phe Asp Lys Ala Lys His
            340                 345                 350 gaa atc aaa act ata aaa ata gta gga cca gaa gaa aat cta agt caa           1104
Glu Ile Lys Thr Ile Lys Ile Val Gly Pro Glu Glu Asn Leu Ser Gln
        355                 360                 365 gcg gaa gcc aga aac atg gga atg gac ttt tgc cgt cag gat gaa aag           1152
Ala Glu Ala Arg Asn Met Gly Met Asp Phe Cys Arg Gln Asp Glu Lys
    370                 375                 380 tgt gat tat tac ttt agt gtg gat gca gat gtt gtt ttg aca aat cca           1200
Cys Asp Tyr Tyr Phe Ser Val Asp Ala Asp Val Val Leu Thr Asn Pro
385                 390                 395                 400 agg act tta aaa att ttg att gaa caa aac aga aag atc att gct cct           1248
Arg Thr Leu Lys Ile Leu Ile Glu Gln Asn Arg Lys Ile Ile Ala Pro
                405                 410                 415 ctt gta act cgt cat gga aag ctg tgg tcc aat ttc tgg gga gca ttg           1296
Leu Val Thr Arg His Gly Lys Leu Trp Ser Asn Phe Trp Gly Ala Leu
            420                 425                 430
```

```
agt cct gat gga tac tat gca cga tct gaa gat tat gtg gat att gtt      1344
Ser Pro Asp Gly Tyr Tyr Ala Arg Ser Glu Asp Tyr Val Asp Ile Val
        435                 440                 445 caa ggg aat aga gta gga gta tgg aat gtc cca tat atg gct aat gtg      1392
Gln Gly Asn Arg Val Gly Val Trp Asn Val Pro Tyr Met Ala Asn Val
    450                 455                 460 tac tta att aaa gga aag aca ctc cga tca gag atg aat gaa agg aac      1440
Tyr Leu Ile Lys Gly Lys Thr Leu Arg Ser Glu Met Asn Glu Arg Asn
465                 470                 475                 480 tat ttt gtt cgt gat aaa ctg gat cct gat atg gct ctt tgc cga aat      1488
Tyr Phe Val Arg Asp Lys Leu Asp Pro Asp Met Ala Leu Cys Arg Asn
                485                 490                 495 gct aga gaa atg ggt gta ttt atg tac att tct aat aga cat gaa ttt      1536
Ala Arg Glu Met Gly Val Phe Met Tyr Ile Ser Asn Arg His Glu Phe
            500                 505                 510 gga agg cta tta tcc act gct aat tac aat act tcc cat tat aac aat      1584
Gly Arg Leu Leu Ser Thr Ala Asn Tyr Asn Thr Ser His Tyr Asn Asn
        515                 520                 525 gac ctc tgg cag att ttt gaa aat cct gtg gac tgg aag gaa aag tat      1632
Asp Leu Trp Gln Ile Phe Glu Asn Pro Val Asp Trp Lys Glu Lys Tyr
    530                 535                 540 ata aac cgt gat tat tca aag att ttc act gaa aat ata gtt gaa cag      1680
Ile Asn Arg Asp Tyr Ser Lys Ile Phe Thr Glu Asn Ile Val Glu Gln
545                 550                 555                 560 ccc tgt cca gat gtc ttt tgg ttc ccc ata ttt tct gaa aaa gcc tgt      1728
Pro Cys Pro Asp Val Phe Trp Phe Pro Ile Phe Ser Glu Lys Ala Cys
                565                 570                 575 gat gaa ttg gta gaa gaa atg gaa cat tac ggc aaa tgg tct ggg gga      1776
Asp Glu Leu Val Glu Glu Met Glu His Tyr Gly Lys Trp Ser Gly Gly
            580                 585                 590 aaa cat cat gat agc cgt ata tct ggt ggt tat gaa aat gtc cca act      1824
Lys His His Asp Ser Arg Ile Ser Gly Gly Tyr Glu Asn Val Pro Thr
        595                 600                 605 gat gat atc cac atg aag caa gtt gat ctg gag aat gta tgg ctt gat      1872
Asp Asp Ile His Met Lys Gln Val Asp Leu Glu Asn Val Trp Leu Asp
    610                 615                 620 ttt atc cgg gag ttc att gca cca gtt aca ctg aag gtc ttt gca ggc      1920
Phe Ile Arg Glu Phe Ile Ala Pro Val Thr Leu Lys Val Phe Ala Gly
625                 630                 635                 640 tat tat acg aag gga ttt gca cta ctg aat ttt gta gta aaa tac tcc      1968
Tyr Tyr Thr Lys Gly Phe Ala Leu Leu Asn Phe Val Val Lys Tyr Ser
                645                 650                 655 cct gaa cga cag cgt tct ctt cgt cct cat cat gat gct tct aca ttt      2016
Pro Glu Arg Gln Arg Ser Leu Arg Pro His His Asp Ala Ser Thr Phe
            660                 665                 670 acc ata aac att gca ctt aat aac gtg gga gaa gac ttt cag gga ggt      2064
Thr Ile Asn Ile Ala Leu Asn Asn Val Gly Glu Asp Phe Gln Gly Gly
        675                 680                 685 ggt tgc aaa ttt cta agg tac aat tgc tct att gag tca cca cga aaa      2112
Gly Cys Lys Phe Leu Arg Tyr Asn Cys Ser Ile Glu Ser Pro Arg Lys
    690                 695                 700 ggc tgg agc ttc atg cat cct ggg aga ctc aca cat ttg cat gaa gga      2160
Gly Trp Ser Phe Met His Pro Gly Arg Leu Thr His Leu His Glu Gly
705                 710                 715                 720 ctt cct gtt aaa aat gga aca aga tac att gca gtg tca ttt ata gat      2208
Leu Pro Val Lys Asn Gly Thr Arg Tyr Ile Ala Val Ser Phe Ile Asp
                725                 730                 735 ccc taa gtt att tac ttt tca ttg aat tga aatttatttt gggtgaatga        2258
Pro
```

```
ctggcatgaa cacgtctttg aagttgtggc tgagaagatg agaggaatat ttaaataaca    2318
tcaacagaac aacttcactt tgggccaaac atttgaaaaa cttttttataa aaaattgttt   2378
gatatttctt aatgtctgct ctgagcctta aaacacagat tgaagaagaa agaaagaaa     2438
aaacttaaat atttatttct atgctttgtt gcctctgaga ataatgacaa tttatgaatt    2498
tgtgtttcaa attgataaaa tatttaggta caaataacaa gactaataat attttcttat    2558
ttaaaaaaag catgggaaga tttttatttta tcaaaatata gaggaaatgt agacaaaatg   2618
gatataaatg aaaattacca tgttgtaaaa ccttgaaaat cagattctaa ctgattgtat    2678
gcaactaagt atttctgaac acctatgcag gtcttattta cagtgttact aagggaacac    2738
acaaagaatt acacaacgtt ttcctcaaga aaatggtaca aaacacaacc gaggagcgta    2798
tacagttgaa aacattttttg ttttgattgg aaggcagatt attttatatt agtattaaaa   2858
atcaaaccct atgtttcttt cagatgaatc ttccaaagtg gattatatta agcaggtatt    2918
agatttagaa aaccttttcca tttcttaaag tattatcaag tgtcaagatc agcaagtgtc   2978
cttaagtcaa ataggttttt ttttgttggt ggttgtgctt gctttccttt tttagaaagt    3038
tctagaaaat aggaaaacga aaaatttcat tgagatgagt agtgcattta attatttttt   3098
aaaaaacttt ttaagtactt gaattttata tcaggaaaac aaagttgttg agccttgctt   3158
cttccgtttt gcccttttgtc tcgctcctta ttctttttttg gggggagggt tatttgcttt  3218
tttatcttcc tggcataatt tccattttat tcttctgagt gtctatgtta acttccctct    3278
atcccgctta taaaaaaatt ctccaacaaa aatacttgtt gacttgatgt tttatcactt    3338
ctctaagtaa ggttgaaata tccttattgt agctactgtt tttaatgtaa aggttaaact    3398
tgaaaagaaa ttcttaatca cggtgccaaa attcattttc taacaccatg tgttagaaaa   3458
ttataaaaaa taaaataatt ttaaaaaaaa aaaaaaaaaa aaaaa                   3503
```

<210> SEQ ID NO 24
<211> LENGTH: 737
<212> TYPE: PRT
<213> ORGANISM: Homo sapiens

<400> SEQUENCE: 24

```
Met Gly Gly Cys Thr Val Lys Pro Gln Leu Leu Leu Ala Leu Val
 1               5                  10                  15

Leu His Pro Trp Asn Pro Cys Leu Gly Ala Asp Ser Glu Lys Pro Ser
                20                  25                  30

Ser Ile Pro Thr Asp Lys Leu Leu Val Ile Thr Val Ala Thr Lys Glu
            35                  40                  45

Ser Asp Gly Phe His Arg Phe Met Gln Ser Ala Lys Tyr Phe Asn Tyr
        50                  55                  60

Thr Val Lys Val Leu Gly Gln Gly Glu Glu Trp Arg Gly Gly Asp Gly
    65                  70                  75                  80

Ile Asn Ser Ile Gly Gly Gln Lys Val Arg Leu Met Lys Glu Val
                85                  90                  95

Met Glu His Tyr Ala Asp Gln Asp Leu Val Val Met Phe Thr Glu
            100                 105                 110

Cys Phe Asp Val Ile Phe Ala Gly Gly Pro Glu Glu Val Leu Lys Lys
        115                 120                 125

Phe Gln Lys Ala Asn His Lys Val Val Phe Ala Ala Asp Gly Ile Leu
    130                 135                 140

Trp Pro Asp Lys Arg Leu Ala Asp Lys Tyr Pro Val Val His Ile Gly
145                 150                 155                 160
```

-continued

```
Lys Arg Tyr Leu Asn Ser Gly Gly Phe Ile Gly Tyr Ala Pro Tyr Val
                165                 170                 175
Asn Arg Ile Val Gln Gln Trp Asn Leu Gln Asp Asn Asp Asp Asp Gln
            180                 185                 190
Leu Phe Tyr Thr Lys Val Tyr Ile Asp Pro Leu Lys Arg Glu Ala Ile
        195                 200                 205
Asn Ile Thr Leu Asp His Lys Cys Lys Ile Phe Gln Thr Leu Asn Gly
    210                 215                 220
Ala Val Asp Glu Val Val Leu Lys Phe Glu Asn Gly Lys Ala Arg Ala
225                 230                 235                 240
Lys Asn Thr Phe Tyr Glu Thr Leu Pro Val Ala Ile Asn Gly Asn Gly
                245                 250                 255
Pro Thr Lys Ile Leu Leu Asn Tyr Phe Gly Asn Tyr Val Pro Asn Ser
            260                 265                 270
Trp Thr Gln Asp Asn Gly Cys Thr Leu Cys Glu Phe Asp Thr Val Asp
        275                 280                 285
Leu Ser Ala Val Asp Val His Pro Asn Val Ser Ile Gly Val Phe Ile
    290                 295                 300
Glu Gln Pro Thr Pro Phe Leu Pro Arg Phe Leu Asp Ile Leu Leu Thr
305                 310                 315                 320
Leu Asp Tyr Pro Lys Glu Ala Leu Lys Leu Phe Ile His Asn Lys Glu
                325                 330                 335
Val Tyr His Glu Lys Asp Ile Lys Val Phe Phe Asp Lys Ala Lys His
            340                 345                 350
Glu Ile Lys Thr Ile Lys Ile Val Gly Pro Glu Glu Asn Leu Ser Gln
        355                 360                 365
Ala Glu Ala Arg Asn Met Gly Met Asp Phe Cys Arg Gln Asp Glu Lys
    370                 375                 380
Cys Asp Tyr Tyr Phe Ser Val Asp Ala Asp Val Val Leu Thr Asn Pro
385                 390                 395                 400
Arg Thr Leu Lys Ile Leu Ile Glu Gln Asn Arg Lys Ile Ile Ala Pro
                405                 410                 415
Leu Val Thr Arg His Gly Lys Leu Trp Ser Asn Phe Trp Gly Ala Leu
            420                 425                 430
Ser Pro Asp Gly Tyr Tyr Ala Arg Ser Glu Asp Tyr Val Asp Ile Val
        435                 440                 445
Gln Gly Asn Arg Val Gly Val Trp Asn Val Pro Tyr Met Ala Asn Val
    450                 455                 460
Tyr Leu Ile Lys Gly Lys Thr Leu Arg Ser Glu Met Asn Glu Arg Asn
465                 470                 475                 480
Tyr Phe Val Arg Asp Lys Leu Asp Pro Asp Met Ala Leu Cys Arg Asn
                485                 490                 495
Ala Arg Glu Met Gly Val Phe Met Tyr Ile Ser Asn Arg His Glu Phe
            500                 505                 510
Gly Arg Leu Leu Ser Thr Ala Asn Tyr Asn Thr Ser His Tyr Asn Asn
        515                 520                 525
Asp Leu Trp Gln Ile Phe Glu Asn Pro Val Asp Trp Lys Glu Lys Tyr
    530                 535                 540
Ile Asn Arg Asp Tyr Ser Lys Ile Phe Thr Glu Asn Ile Val Glu Gln
545                 550                 555                 560
Pro Cys Pro Asp Val Phe Trp Phe Pro Ile Phe Ser Glu Lys Ala Cys
                565                 570                 575
```

```
Asp Glu Leu Val Glu Glu Met Glu His Tyr Gly Lys Trp Ser Gly Gly
            580                 585                 590

Lys His His Asp Ser Arg Ile Ser Gly Gly Tyr Glu Asn Val Pro Thr
            595                 600                 605

Asp Asp Ile His Met Lys Gln Val Asp Leu Glu Asn Val Trp Leu Asp
            610                 615                 620

Phe Ile Arg Glu Phe Ile Ala Pro Val Thr Leu Lys Val Phe Ala Gly
625                 630                 635                 640

Tyr Tyr Thr Lys Gly Phe Ala Leu Leu Asn Phe Val Lys Tyr Ser
                645                 650                 655

Pro Glu Arg Gln Arg Ser Leu Arg Pro His His Asp Ala Ser Thr Phe
            660                 665                 670

Thr Ile Asn Ile Ala Leu Asn Asn Val Gly Glu Asp Phe Gln Gly Gly
            675                 680                 685

Gly Cys Lys Phe Leu Arg Tyr Asn Cys Ser Ile Glu Ser Pro Arg Lys
            690                 695                 700

Gly Trp Ser Phe Met His Pro Gly Arg Leu Thr His Leu His Glu Gly
705                 710                 715                 720

Leu Pro Val Lys Asn Gly Thr Arg Tyr Ile Ala Val Ser Phe Ile Asp
                725                 730                 735

Pro

<210> SEQ ID NO 25
<211> LENGTH: 2277
<212> TYPE: DNA
<213> ORGANISM: Homo sapiens
<220> FEATURE:
<221> NAME/KEY: CDS
<222> LOCATION: (1)..(2277)

<400> SEQUENCE: 25 atg ggg gga tgc acg gtg aag cct cag ctg ctg ctc ctg gcg ctc gtc       48
Met Gly Gly Cys Thr Val Lys Pro Gln Leu Leu Leu Leu Ala Leu Val
  1               5                  10                  15 ctc cac ccc tgg aat ccc tgt ctg ggt gcg gac tcg gag aag ccc tcg       96
Leu His Pro Trp Asn Pro Cys Leu Gly Ala Asp Ser Glu Lys Pro Ser
             20                  25                  30 agc atc ccc aca gat aaa tta tta gtc ata act gta gca aca aaa gaa      144
Ser Ile Pro Thr Asp Lys Leu Leu Val Ile Thr Val Ala Thr Lys Glu
         35                  40                  45 agt gat gga ttc cat cga ttt atg cag tca gcc aaa tat ttc aat tat      192
Ser Asp Gly Phe His Arg Phe Met Gln Ser Ala Lys Tyr Phe Asn Tyr
 50                  55                  60 act gtg aag gtc ctt ggt caa gga gaa gaa tgg aga ggt ggt gat gga      240
Thr Val Lys Val Leu Gly Gln Gly Glu Glu Trp Arg Gly Gly Asp Gly
 65                  70                  75                  80 att aat agt att gga ggg ggc cag aaa gtg aga tta atg aaa gaa gtc      288
Ile Asn Ser Ile Gly Gly Gly Gln Lys Val Arg Leu Met Lys Glu Val
             85                  90                  95 atg gaa cac tat gct gat caa gat gat ctg gtt gtc atg ttt act gaa      336
Met Glu His Tyr Ala Asp Gln Asp Asp Leu Val Val Met Phe Thr Glu
            100                 105                 110 tgc ttt gat gtc ata ttt gct ggt ggt cca gaa gaa gtt cta aaa aaa      384
Cys Phe Asp Val Ile Phe Ala Gly Gly Pro Glu Glu Val Leu Lys Lys
        115                 120                 125 ttc caa aag gca aac cac aaa gtg gtc ttt gca gca gat gga att ttg      432
Phe Gln Lys Ala Asn His Lys Val Val Phe Ala Ala Asp Gly Ile Leu
    130                 135                 140
```

-continued

| | | |
|---|---|---|
| tgg cca gat aaa aga cta gca gac aag tat cct gtt gtg cac att ggg<br>Trp Pro Asp Lys Arg Leu Ala Asp Lys Tyr Pro Val Val His Ile Gly<br>145                   150                   155                   160 | 480 |
| aaa cgc tat ctg aat tca gga gga ttt att ggc tat gct cca tat gtc<br>Lys Arg Tyr Leu Asn Ser Gly Gly Phe Ile Gly Tyr Ala Pro Tyr Val<br>                 165                   170                   175 | 528 |
| aac cgt ata gtt caa caa tgg aat ctc cag gat aat gat gat gat cag<br>Asn Arg Ile Val Gln Gln Trp Asn Leu Gln Asp Asn Asp Asp Asp Gln<br>         180                   185                   190 | 576 |
| ctc ttt tac act aaa gtt tac att gat cca ctg aaa agg gaa gct att<br>Leu Phe Tyr Thr Lys Val Tyr Ile Asp Pro Leu Lys Arg Glu Ala Ile<br>              195                   200                   205 | 624 |
| aac atc aca ttg gat cac aaa tgc aaa att ttc cag acc tta aat gga<br>Asn Ile Thr Leu Asp His Lys Cys Lys Ile Phe Gln Thr Leu Asn Gly<br>210                   215                   220 | 672 |
| gct gta gat gaa gtt gtt tta aaa ttt gaa aat ggc aaa gcc aga gct<br>Ala Val Asp Glu Val Val Leu Lys Phe Glu Asn Gly Lys Ala Arg Ala<br>225                   230                   235                   240 | 720 |
| aag aat aca ttt tat gaa aca tta cca gtg gca att aat gga aat gga<br>Lys Asn Thr Phe Tyr Glu Thr Leu Pro Val Ala Ile Asn Gly Asn Gly<br>              245                   250                   255 | 768 |
| ccc acc aag att ctc ctg aat tat ttt gga aac tat gta ccc aat tca<br>Pro Thr Lys Ile Leu Leu Asn Tyr Phe Gly Asn Tyr Val Pro Asn Ser<br>                 260                   265                   270 | 816 |
| tgg aca cag gat aat ggc tgc act ctt tgt gaa ttc gat aca gtc gac<br>Trp Thr Gln Asp Asn Gly Cys Thr Leu Cys Glu Phe Asp Thr Val Asp<br>         275                   280                   285 | 864 |
| ttg tct gca gta gat gtc cat cca aac gta tca ata ggt gtt ttt att<br>Leu Ser Ala Val Asp Val His Pro Asn Val Ser Ile Gly Val Phe Ile<br>290                   295                   300 | 912 |
| gag caa cca acc cct ttt cta cct cgg ttt ctg gac ata ttg ttg aca<br>Glu Gln Pro Thr Pro Phe Leu Pro Arg Phe Leu Asp Ile Leu Leu Thr<br>305                   310                   315                   320 | 960 |
| ctg gat tac cca aaa gaa gca ctt aaa ctt ttt att cat aac aaa gaa<br>Leu Asp Tyr Pro Lys Glu Ala Leu Lys Leu Phe Ile His Asn Lys Glu<br>              325                   330                   335 | 1008 |
| gtt tat cat gaa aag gac atc aag gta ttt ttt gat aaa gct aag cat<br>Val Tyr His Glu Lys Asp Ile Lys Val Phe Phe Asp Lys Ala Lys His<br>         340                   345                   350 | 1056 |
| gaa atc aaa act ata aaa ata gta gga cca gaa gaa aat cta agt caa<br>Glu Ile Lys Thr Ile Lys Ile Val Gly Pro Glu Glu Asn Leu Ser Gln<br>              355                   360                   365 | 1104 |
| gcg gaa gcc aga aac atg gga atg gac ttt tgc cgt cag gat gaa aag<br>Ala Glu Ala Arg Asn Met Gly Met Asp Phe Cys Arg Gln Asp Glu Lys<br>         370                   375                   380 | 1152 |
| tgt gat tat tac ttt agt gtg gat gca gat gtt gtt ttg aca aat cca<br>Cys Asp Tyr Tyr Phe Ser Val Asp Ala Asp Val Val Leu Thr Asn Pro<br>385                   390                   395                   400 | 1200 |
| agg act tta aaa att ttg att gaa caa aac aga aag atc att gct cct<br>Arg Thr Leu Lys Ile Leu Ile Glu Gln Asn Arg Lys Ile Ile Ala Pro<br>              405                   410                   415 | 1248 |
| ctt gta act cgt cat gga aag ctg tgg tcc aat ttc tgg gga gca ttg<br>Leu Val Thr Arg His Gly Lys Leu Trp Ser Asn Phe Trp Gly Ala Leu<br>         420                   425                   430 | 1296 |
| agt cct gat gga tac tat gca cga tct gaa gat tat gtg gat att gtt<br>Ser Pro Asp Gly Tyr Tyr Ala Arg Ser Glu Asp Tyr Val Asp Ile Val<br>              435                   440                   445 | 1344 |
| caa ggg aat aga gta gga gta tgg aat gtc cca tat atg gct aat gtg<br>Gln Gly Asn Arg Val Gly Val Trp Asn Val Pro Tyr Met Ala Asn Val<br>         450                   455                   460 | 1392 |

-continued

```
tac tta att aaa gga aag aca ctc cga tca gag atg aat gaa agg aac      1440
Tyr Leu Ile Lys Gly Lys Thr Leu Arg Ser Glu Met Asn Glu Arg Asn
465                 470                 475                 480 tat ttt gtt cgt gat aaa ctg gat cct gat atg gct ctt tgc cga aat      1488
Tyr Phe Val Arg Asp Lys Leu Asp Pro Asp Met Ala Leu Cys Arg Asn
                485                 490                 495 gct aga gaa atg act tta caa agg gaa aaa gac tcc cct act ccg gaa      1536
Ala Arg Glu Met Thr Leu Gln Arg Glu Lys Asp Ser Pro Thr Pro Glu
        500                 505                 510 aca ttc caa atg ctc agc ccc cca aag ggt gta ttt atg tac att tct      1584
Thr Phe Gln Met Leu Ser Pro Pro Lys Gly Val Phe Met Tyr Ile Ser
            515                 520                 525 aat aga cat gaa ttt gga agg cta tta tcc act gct aat tac aat act      1632
Asn Arg His Glu Phe Gly Arg Leu Leu Ser Thr Ala Asn Tyr Asn Thr
530                 535                 540 tcc cat tat aac aat gac ctc tgg cag att ttt gaa aat cct gtg gac      1680
Ser His Tyr Asn Asn Asp Leu Trp Gln Ile Phe Glu Asn Pro Val Asp
545                 550                 555                 560 tgg aag gaa aag tat ata aac cgt gat tat tca aag att ttc act gaa      1728
Trp Lys Glu Lys Tyr Ile Asn Arg Asp Tyr Ser Lys Ile Phe Thr Glu
                565                 570                 575 aat ata gtt gaa cag ccc tgt cca gat gtc ttt tgg ttc ccc ata ttt      1776
Asn Ile Val Glu Gln Pro Cys Pro Asp Val Phe Trp Phe Pro Ile Phe
            580                 585                 590 tct gaa aaa gcc tgt gat gaa ttg gta gaa gaa atg gaa cat tac ggc      1824
Ser Glu Lys Ala Cys Asp Glu Leu Val Glu Glu Met Glu His Tyr Gly
        595                 600                 605 aaa tgg tct ggg gga aaa cat cat gat agc cgt ata tct ggt ggt tat      1872
Lys Trp Ser Gly Gly Lys His His Asp Ser Arg Ile Ser Gly Gly Tyr
    610                 615                 620 gaa aat gtc cca act gat gat atc cac atg aag caa gtt gat ctg gag      1920
Glu Asn Val Pro Thr Asp Asp Ile His Met Lys Gln Val Asp Leu Glu
625                 630                 635                 640 aat gta tgg ctt gat ttt atc cgg gag ttc att gca cca gtt aca ctg      1968
Asn Val Trp Leu Asp Phe Ile Arg Glu Phe Ile Ala Pro Val Thr Leu
                645                 650                 655 aag gtc ttt gca ggc tat tat acg aag gga ttt gca cta ctg aat ttt      2016
Lys Val Phe Ala Gly Tyr Tyr Thr Lys Gly Phe Ala Leu Leu Asn Phe
            660                 665                 670 gta gta aaa tac tcc cct gaa cga cag cgt tct ctt cgt cct cat cat      2064
Val Val Lys Tyr Ser Pro Glu Arg Gln Arg Ser Leu Arg Pro His His
        675                 680                 685 gat gct tct aca ttt acc ata aac att gca ctt aat aac gtg gga gaa      2112
Asp Ala Ser Thr Phe Thr Ile Asn Ile Ala Leu Asn Asn Val Gly Glu
    690                 695                 700 gac ttt cag gga ggt ggt tgc aaa ttt cta agg tac aat tgc tct att      2160
Asp Phe Gln Gly Gly Gly Cys Lys Phe Leu Arg Tyr Asn Cys Ser Ile
705                 710                 715                 720 gag tca cca cga aaa ggc tgg agc ttc atg cat cct ggg aga ctc aca      2208
Glu Ser Pro Arg Lys Gly Trp Ser Phe Met His Pro Gly Arg Leu Thr
                725                 730                 735 cat ttg cat gaa gga ctt cct gtt aaa aat gga aca aga tac att gca      2256
His Leu His Glu Gly Leu Pro Val Lys Asn Gly Thr Arg Tyr Ile Ala
            740                 745                 750 gtg tca ttt ata gat ccc taa                                          2277
Val Ser Phe Ile Asp Pro
        755
```

<210> SEQ ID NO 26

<211> LENGTH: 758
<212> TYPE: PRT
<213> ORGANISM: Homo sapiens

<400> SEQUENCE: 26

```
Met Gly Gly Cys Thr Val Lys Pro Gln Leu Leu Leu Ala Leu Val
 1               5                  10                  15

Leu His Pro Trp Asn Pro Cys Leu Gly Ala Asp Ser Glu Lys Pro Ser
                20                  25                  30

Ser Ile Pro Thr Asp Lys Leu Leu Val Ile Thr Val Ala Thr Lys Glu
            35                  40                  45

Ser Asp Gly Phe His Arg Phe Met Gln Ser Ala Lys Tyr Phe Asn Tyr
        50                  55                  60

Thr Val Lys Val Leu Gly Gln Gly Glu Trp Arg Gly Gly Asp Gly
 65                  70                  75                  80

Ile Asn Ser Ile Gly Gly Gly Gln Lys Val Arg Leu Met Lys Glu Val
                85                  90                  95

Met Glu His Tyr Ala Asp Gln Asp Asp Leu Val Val Met Phe Thr Glu
            100                 105                 110

Cys Phe Asp Val Ile Phe Ala Gly Gly Pro Glu Glu Val Leu Lys Lys
        115                 120                 125

Phe Gln Lys Ala Asn His Lys Val Val Phe Ala Ala Asp Gly Ile Leu
    130                 135                 140

Trp Pro Asp Lys Arg Leu Ala Asp Lys Tyr Pro Val Val His Ile Gly
145                 150                 155                 160

Lys Arg Tyr Leu Asn Ser Gly Gly Phe Ile Gly Tyr Ala Pro Tyr Val
                165                 170                 175

Asn Arg Ile Val Gln Gln Trp Asn Leu Gln Asp Asn Asp Asp Asp Gln
            180                 185                 190

Leu Phe Tyr Thr Lys Val Tyr Ile Asp Pro Leu Lys Arg Glu Ala Ile
        195                 200                 205

Asn Ile Thr Leu Asp His Lys Cys Lys Ile Phe Gln Thr Leu Asn Gly
    210                 215                 220

Ala Val Asp Glu Val Val Leu Lys Phe Glu Asn Gly Lys Ala Arg Ala
225                 230                 235                 240

Lys Asn Thr Phe Tyr Glu Thr Leu Pro Val Ala Ile Asn Gly Asn Gly
                245                 250                 255

Pro Thr Lys Ile Leu Leu Asn Tyr Phe Gly Asn Tyr Val Pro Asn Ser
            260                 265                 270

Trp Thr Gln Asp Asn Gly Cys Thr Leu Cys Glu Phe Asp Thr Val Asp
        275                 280                 285

Leu Ser Ala Val Asp Val His Pro Asn Val Ser Ile Gly Val Phe Ile
    290                 295                 300

Glu Gln Pro Thr Pro Phe Leu Pro Arg Phe Leu Asp Ile Leu Leu Thr
305                 310                 315                 320

Leu Asp Tyr Pro Lys Glu Ala Leu Lys Leu Phe Ile His Asn Lys Glu
                325                 330                 335

Val Tyr His Glu Lys Asp Ile Lys Val Phe Phe Asp Lys Ala Lys His
            340                 345                 350

Glu Ile Lys Thr Ile Lys Ile Val Gly Pro Glu Glu Asn Leu Ser Gln
        355                 360                 365

Ala Glu Ala Arg Asn Met Gly Met Asp Phe Cys Arg Gln Asp Glu Lys
    370                 375                 380

Cys Asp Tyr Tyr Phe Ser Val Asp Ala Asp Val Val Leu Thr Asn Pro
```

-continued

```
            385                 390                 395                 400
Arg Thr Leu Lys Ile Leu Ile Glu Gln Asn Arg Lys Ile Ile Ala Pro
                405                 410                 415
Leu Val Thr Arg His Gly Lys Leu Trp Ser Asn Phe Trp Gly Ala Leu
                420                 425                 430
Ser Pro Asp Gly Tyr Tyr Ala Arg Ser Glu Asp Tyr Val Asp Ile Val
                435                 440                 445
Gln Gly Asn Arg Val Gly Val Trp Asn Val Pro Tyr Met Ala Asn Val
            450                 455                 460
Tyr Leu Ile Lys Gly Lys Thr Leu Arg Ser Glu Met Asn Glu Arg Asn
465                 470                 475                 480
Tyr Phe Val Arg Asp Lys Leu Asp Pro Asp Met Ala Leu Cys Arg Asn
                485                 490                 495
Ala Arg Glu Met Thr Leu Gln Arg Glu Lys Asp Ser Pro Thr Pro Glu
                500                 505                 510
Thr Phe Gln Met Leu Ser Pro Pro Lys Gly Val Phe Met Tyr Ile Ser
                515                 520                 525
Asn Arg His Glu Phe Gly Arg Leu Leu Ser Thr Ala Asn Tyr Asn Thr
            530                 535                 540
Ser His Tyr Asn Asn Asp Leu Trp Gln Ile Phe Glu Asn Pro Val Asp
545                 550                 555                 560
Trp Lys Glu Lys Tyr Ile Asn Arg Asp Tyr Ser Lys Ile Phe Thr Glu
                565                 570                 575
Asn Ile Val Glu Gln Pro Cys Pro Asp Val Phe Trp Phe Pro Ile Phe
                580                 585                 590
Ser Glu Lys Ala Cys Asp Glu Leu Val Glu Glu Met Glu His Tyr Gly
                595                 600                 605
Lys Trp Ser Gly Gly Lys His His Asp Ser Arg Ile Ser Gly Gly Tyr
            610                 615                 620
Glu Asn Val Pro Thr Asp Asp Ile His Met Lys Gln Val Asp Leu Glu
625                 630                 635                 640
Asn Val Trp Leu Asp Phe Ile Arg Glu Phe Ile Ala Pro Val Thr Leu
                645                 650                 655
Lys Val Phe Ala Gly Tyr Tyr Thr Lys Gly Phe Ala Leu Leu Asn Phe
                660                 665                 670
Val Val Lys Tyr Ser Pro Glu Arg Gln Arg Ser Leu Arg Pro His His
                675                 680                 685
Asp Ala Ser Thr Phe Thr Ile Asn Ile Ala Leu Asn Asn Val Gly Glu
            690                 695                 700
Asp Phe Gln Gly Gly Gly Cys Lys Phe Leu Arg Tyr Asn Cys Ser Ile
705                 710                 715                 720
Glu Ser Pro Arg Lys Gly Trp Ser Phe Met His Pro Gly Arg Leu Thr
                725                 730                 735
His Leu His Glu Gly Leu Pro Val Lys Asn Gly Thr Arg Tyr Ile Ala
                740                 745                 750
Val Ser Phe Ile Asp Pro
            755
```

<210> SEQ ID NO 27
<211> LENGTH: 9
<212> TYPE: PRT
<213> ORGANISM: Artificial sequence
<220> FEATURE:
<223> OTHER INFORMATION: Synthetic peptide used as a substrate in the
      measurement of LH activity

```
<400> SEQUENCE: 27

Ile Lys Gly Ile Lys Gly Ile Lys Gly
1               5
```

METHOD FOR GLYCOSYLATING HYDROXYLYSINE RESIDUES

This application is the U.S. National Stage application of PCT Application No. PCT/FI01/00528, filed Jun. 4, 2001, which claims priority under 35 U.S.C. § 119(a)-(d) of Finnish Patent Application 20001328, filed on Jun. 2, 2000.

This invention relates to a multifunctional enzyme. In particular this invention relates to a method for producing an enzyme capable of glycosylation of hydroxylysyl residues of polypeptides or peptides comprising such residues. This invention relates in particular to a method for producing glucosyltransferase and galactosyltransferase enzyme and to a nucleotide sequence encoding these activities. This invention relates also to a method for glycosylating hydroxylysyl residues of polypeptides or peptides comprising such residues.

Collagens are the extracellular proteins found essentially in all tissues. They play a crucial role in maintenance of the structural integrity of tissues and by binding to cell receptors in regulation of cellular behaviour. They form a diverse range of high organized supra-molecular assemblies in the extracellular matrix generating structural scaffolds to keep cells in their place within the tissue, connect tissues within an organ and facilitate attachment and migration of cells. Furthermore, the collagens like other extracellular proteins, bind to growth factors and other regulatory components of cells and modulate cellular metabolism. To date, 19 genetically distinct collagen types have been identified (Kielty et al., 1993; Kadler, 1994; Prockop and Kivirikko, 1995). The collagen molecule is composed of three polypeptide chains, which coil each other into a triple-helical structure. Some of the collagen types, such as type I, II, and III collagens, have a rod like structure without any interruptions in the helical region, whereas in the other types triple-helical regions are interrupted with multiple short nonhelical sequences. The collagen molecules are aggregated in tissues into supra-molecular structures, where they form fibrils, beaded filaments, net-like or other kind of structures depending on the type of collagen.

The biosynthesis of collagen includes several post-translational modifications, which include hydroxylation of lysyl residues, galactosylation of hydroxylysyl residues and glucosylation of galactosylhydroxylysyl residues. These are events occurring in the endoplasmic reticulum before triple helix formation. Hydroxylysine occurs in Y position of the repeating X-Y-Gly triplet within the helical region of collagen molecule. Hydroxy-lysine also occurs in the sequence of nonhelical telopeptide regions of some collagen types, when glycine is replaced either by serine or alanine (Kivirikko et al., 1992; Kielty et al., 1993). The hydroxy groups of hydroxylysyl residues serve important functions in providing attachment sites for glycosyl residues, either monosaccharide galactose or disaccharide glucosylgalactose. The hydroxy groups also play crucial role in the formation of inter- and intramolecular collagen crosslinks. The biological role of hydroxylysyl linked carbohydrates, collagen-specific structures, is not clear. The extent of lysine hydroxylation as well as glycosylation of hydroxylysyl residues is very variable, both between collagen types and within the same collagen in different tissues and at different ages (Kivirikko et al., 1992; Kielty et al., 1993).

Hydroxylysine occurs also in some proteins which are not defined as collagens but which contain collagenous domain. Collectin proteins contain collagenous regions linked to C-terminal carbohydrate recognition domains common to the family of calcium-dependent carbohydrate-binding proteins known as C-type lectins. At least mannan-binding protein, conglutinin, the pulmonary surfactant proteins A and D and CL-43 belong to the group of collectin proteins. Other examples of proteins having a collagenous domain are core-specific lectin (CLS), C1 q complement and acetylcholinesterases. Bovine serum lectin CL-43 belongs to the group of collagen-like proteins. Some hydroxylysine residues are found in proteins which do not have collagenous domains. Examples of such proteins are anglerfish somatostatin-28, human tissue plasminogen activator (rtPA), human CD4 receptor (rCD4) and a related chimeric protein (rCD4-IgG) (Valtavaara 1999).

Lysyl hydroxylase (EC 1.14.11.4) catalyzes the hydroxylation of lysyl residues in collagens (or in other proteins having lysyl residues) in a reaction that requires $Fe^{2+}$, 2-oxoglutarate, $O_2$, and ascorbate (Kivirikko et al., 1992). Three enzymes (LH1, LH2, LH3) with LH activity have been isolated and characterized in human (Hautala et al., 1992; Valtavaara et al., 1997, 1998; Passoja et al., 1998) and mouse tissues (Ruotsalainen et al., 1999), LH1 from chicken tissues (Myllylä et al. 1991) and from rat (Amstrong and Last 1995). The LH2 isoform is present in two alternatively spliced forms, LH2a and LH2b (Valtavaara 1999; Yeowell and Walker, 1999).

The cDNA sequence and the deduced amino acid sequence of a nematode, *Caenorhabditis elegans*, are also known (SWISS-PROT: 20679). A phylogenetic analysis shows that the lysyl hydroxylase isoforms are derived from an ancestral gene by two gene duplication events. Isoforms 1 and 2 are more closely related, and have been brought about by a more recent duplication than the less closely related isoform 3 (Ruotsalainen et al. 1999), which is an earlier ancestral derivative of *C. elegans* lysyl hydroxylase.

Galactosyl hydroxylysyl glucosyltransferase (GGT, EC 2.4.1.66) adds glucose to some of galactosyl hydroxylysyl residues in the collagen in a reaction that requires $Mn^{2+}$ and UDP-glucose (Kivirikko and Myllylä, 1979). The enzyme has been purified from chicken embryos (Myllylä et al., 1976) and its catalytic and molecular properties has been characterized (see Kivirikko and Myllylä, 1979).

As described in the above referred literature the cDNAs/genes encoding LH 1, LH2 and LH 3 have been characterized in human and in mouse, LH1 from chicken, rat and bovine (GenBank Accession number o77588) and the ancestral parent of LH1, LH2 and LH3 from *C. elegans*. However, the prior art does not describe the genes or cDNAs encoding glucosyltransferase or galactosyltransferase activity from any source. Although glucosyl-transferase has been purified from chicken embryos and its catalytic and molecular properties has been characterized (Kivirikko and Myllylä, 1979) and galactosyltransferase has been partially purified and characterized from chicken Risteli et al. (1976a and b) the molecular cloning of the enzymes has not been successful and the structure of the enzymes is not known. Accordingly, the production of enzymes capable of glycosylation of hydroxylysyl residues by using genetic engineering techniques has not been possible this far.

SUMMARY

It is an aim of the present invention to eliminate the problems associated with the prior art and to provide a method for recombinant production of the enzymes capable of saccharifying the hydroxylysyl residues in polypeptides or peptides having hydroxylysyl residues. In particular this invention provides the nucleotide sequence encoding glucosyltransferase (E.C. 2.4.1.66) and galactosyltransferase (E.C. 2.4.1.50) activity. Glucosyltransferase and galactosyltransferase are enzymes involved in post-translational modifications of collagen biosynthesis. This invention is based on our findings that the protein produced by human LH3 cDNA and *Caenorhabditis elegans* cDNA is responsible for both lysyl hydroxylase (LH) and glucosyltransferase (GGT) and galactosyltransferase (GT) activity, and that there is no need to process the protein in order to get the activity.

This invention provides a method for producing an enzyme activity capable of glycosylation of hydroxylysyl residues in polypeptides or peptides having these residues or an enzyme having the glycosylating activity and lysyl hydroxylase (LH) activity, which comprises that the nucleotide sequence encoding LH is introduced and expressed in a chosen host and the protein product is recovered from the host cell or from the culture medium. The enzyme may have glycosylating activity although it does not have lysyl hydroxylase activity.

More specifically, the method is mainly characterized by what is stated in the characterizing part of claim 1.

In particular this invention provides a method for producing glucosyltransferase or glucosyltransferase and lysyl hydroxylase (LH). Furthermore this invention provides a method for producing galactosyltransferase (E.C. 2.4.1.50) or galactosyltransferase and lysyl hydroxylase or all these three enzyme activities.

The nucleotide sequence encoding LH may originate from any suitable source having this enzyme activity. Suitable sources are organisms having collagen or protein having collagenous domain or collagen-type protein, because these organisms generally also produce lysyl hydroxylase, or it may be an organism not having the mentioned collagen proteins, but still producing lysyl hydroxylase. The origin may be a eukaryote having only one form of lysyl hydroxylase, such as *C. elegans*, which belongs to nematodes and metazoa or the origin may be an organism producing a lysyl hydroxylase isoform being a derivative of the ancestral lysyl hydroxylase, such as LH3 producing organisms. LH 3 may preferably be from mammalian origin, more preferably from human, bovine, porcine and/or from murine origin. The nucleotide sequence may be synthetic or at least partly synthetic. Within the scope of invention are also nucleotide sequences encoding lysyl hydroxylases isolated from new organism groups provided that the nucleotide sequence encodes also an enzyme activity capable of glycosylating hydroxylysyl residues in polypeptides or peptides having these residues.

In the studies relating to the multifunctionality of the LH3 enzyme, it was found that the LH3 activity can be removed by genetic modification of the nucleotide sequence encoding LH3 without affecting the saccharifying activities.

This invention thus provides also a nucleotide sequence encoding an enzyme having only saccharifying activity, which comprises that the nucleotide sequence encoding LH comprises a modification resulting in partial or complete loss of lysyl hydroxylase activity.

The saccharifying activity may be glucosyltransferase and/or galactosyltransferase activity.

The present invention provides also a glycosyltransferase enzyme produced by the methods of this invention and preferably purified to homogenity. The enzyme product may comprise a factor facilitating the purification of the enzyme. Glycosyltransferase enzyme according to this invention has enzymatic activity in multimeric or monomeric form, in other words, when a substantial amount of the enzyme is in multimeric or monomeric form the glycosyltransferase activity is measurable (is higher than the background; see for example Table IV in Example 10).

The present invention results in many advantages. It makes it possible to produce enzymes capable of saccharifying the hydroxylysyl residues in collagen proteins by recombinant methods. This opens up the possibility to modify the inter- and intramolecular collagen crosslinks, in the formation of which hydroxy groups play a crucial role. It is also possible by the methods of this invention to saccharify collagen-type proteins, proteins having collagenous domain or generally polypeptides or peptides having hydroxylysyl residues. The present invention makes it also possible to prepare synthetic peptides which contain hydroxylysine residues and where saccharification corresponds the in vivo situation. The advantage of this type of polypeptides is that they do not have antigenic properties i.e. they do not result in antibody production and do not cause rejection.

The discovery to find the GT activity, in addition to the GGT and LH activities, in LH3 molecule is significant. It reveals the gene, which provides enormous power to study the function of hydroxylation of lysyl residues, galactosylation of hydroxylysyl residues and glucosylation of galactosylhydroxylysyl residues in an animal model. Manipulation of one gene makes possibly to alter all the reactions at the same time by generation of a gene construct knocking out the whole function of the gene. In the contrary, selective inhibition of the activities in the gene enables the study of these post-translational events separately.

Other features, aspects and advantages of the present invention will become apparent from the following description and appended claims.

BRIEF DESCRIPTION OF THE FIGURES

The foregoing text, as well as the following detailed description of the present invention, will be better understood when read in conjunction with the appended figures in which:

FIG. 2. Analysis of protein produced by LH3 cDNA. (A) Protein produced by the His-tagged LH3 cDNA construct in Sf9 cells, purified by a nickel affinity column and analyzed by western blot by using anti-His tag antibody. Lane 1, crude insect cell lysate; lane 2, flow through; lane 3, wash; lane 4, elution with 100 mM imidazole; lane 5, elution with 200 mM imidazole. Molecular weight markers are indicated. (B) Immunoprecipitation of Sf9 cells transfected with the His-tagged LH3 construct by anti-His tag antibody (lane 1). Precipitated proteins were analyzed by SDS-PAGE and visualized by silver staining. Bands corresponding to IgG polypeptide chains were also present in immunoprecipitate. Sf9 cells were used as a control (lane 2). (C) Immunoprecipitation of a Cos-7 cell lysate with anti-GFP antibody. The cells were transfected by the GFP-tagged LH3 construct. Imunoprecipitated proteins were analyzed by SDS-PAGE and immunostaining was carried out by an anti-GFP antibody. Lane 1, cell lysate: lane 2, cell medium; lane 3, cell lysate obtained from cells transfected by the vector (pEGFP-N1); lane 4, cell medium of the cells transfected by the vector.

FIG. 6. Nucleotides 214-2447, amino acids 1-738 (SEQ ID NO 5 and SEQ ID NO 11).

FIG. 7. Nucleotides 289-2455, amino acids 25-738 (SEQ ID NO 6 and SEQ ID NO 12).

FIG. 8. Nucleotides 289-2455, mutation 1, amino acids 25-231 normal, amino acids 232-356 modified (SEQ ID NO 7 and SEQ ID NO 13).

FIG. 9. Nucleotides 289-2455, mutation 2, amino acids 25-520 normal, amino acids 521-738 missing (SEQ ID NO 8 and SEQ ID NO 14).

FIG. 10. Nucleotides 289-2455, mutation 3, amino acids 25-738, nucleotide 2222 A->C, amino acid 669 D->A (SEQ ID NO 9 and SEQ ID NO 15).

FIG. 11. Nucleotides 289-2455, mutation 4, amino acids 25-668 normal, amino acids 669-698 modified (SEQ ID NO 10 and SEQ ID NO 16).

DETAILED DESCRIPTION OF THE INVENTION

Definitions

Figure 1A:
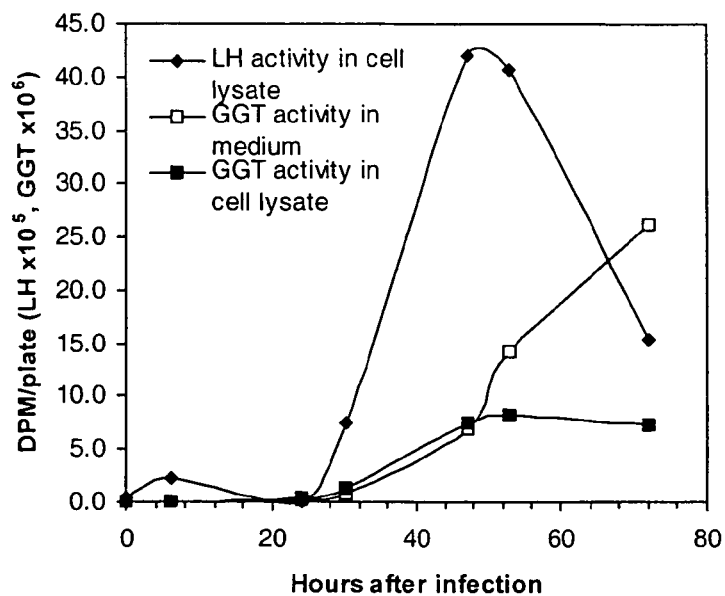
FIG. 1. LH and GGT activity in cells transfected with human LH3 cDNA. (A) Sf9 cells were transfected with a His-tagged construct and LH3 and GGT activities were measured in different time points. (B) Cos-7 cells were transfected with a native LH3 construct, GGT activity was measured in different time points. Nontransfected cells were used as controls.

By "saccharifying enzymes" is meant here enzymes capable of saccharifying the hydroxylysyl residues in polypeptides or peptides having these residues. Saccharifying enzymes mean within the scope of this invention enzymes capable of glucosylation of galactosylhydroxylysyl residues and galactosylation of hydroxylysyl residues. The term "glycosylation" is used here synonymously with the term "saccharification".

By "glycosyltransferase" is meant here glucosyltransferase and galactosyltransferase activity.

By "glycosyl residues" are meant here either monosaccharide galactose or disaccharide glucosylgalactose.

"Glucosyltransferase" (E.C. 2.4.1.66) means here an enzyme capable of glucosylation of galactosylhydroxylysyl residues. Synonyms for glucosyltransferase are collagen glucosyltransferase and galactosyl hydroxylysyl glucosyltransferase. The abbreviation GGT is used for this enzyme activity.

"Galactosyltransferase" (E.C. 2.4.1.50) means here an enzyme capable of galactosylation of hydroxylysyl residues. Synonyms for galactosyltransferase are procollagen galactosyltransferase and hydroxylysine galactosyltransferase.

By "lysyl hydroxylase" is meant here an enzyme capable of hydroxylation of lysyl residues in polypeptides or peptides having these residues. The abbreviation LH is used for this activity. The various isoforms of this enzyme are called LH1, LH2 and LH3. The LH2 is present in two alternatively spliced forms, LH2a and LH2b. In this invention lysyl hydroxylase (LH) means in particular an enzyme having glycosyltransferase acitivity, more specifically glucosyltransferase and/or galactosyltransferase activity. By lysyl-hydroxylase (LH) is meant within the scope of this invention also lysylhydroxylase, which is not enzymatically active, because the enzyme is not in active form. As is described later, the enzyme may be in monomer or multimer form, which does not have lysylhydroxylase activity, but it has glucosyltransferase and/or galactosyltransferase activity.

In the sequence listing the SEQ ID-NOs present the following nucleotide or amino acid sequences:
SEQ ID NO 1 mouse LH3 cDNA
SEQ ID NO 2 mouse LH3 amino acid sequence
SEQ ID NO 3 C. elegans LH cDNA
SEQ ID NO 4 C. elegans LH amino acid sequence
SEQ ID NO 5 human LH3 cDNA nucleotides 214-2447
SEQ ID NO 6 human LH3 cDNA nucleotides 289-2455
SEQ ID NO 7 human LH3 mutation 1
SEQ ID NO 8 human LH3 mutation 2
SEQ ID NO 9 human LH3 mutation 3
SEQ ID NO 10 human LH3 mutation 4
SEQ ID NO 11 human LH3 amino acid sequence, which corresponds to nucleotides 214-2447.
SEQ ID NO 12 human LH3 amino acid sequence, which corresponds to nucleotides 289-2455
SEQ ID NO 13 human LH3 amino acid sequence, which corresponds to mutation 1
SEQ ID NO 14 human LH3 amino acid sequence, corresponds to mutation 2
SEQ ID NO 15 human LH3 amino acid sequence, corresponds to mutation 3

SEQ ID NO 16 human LH3 amino acid sequence, corresponds to mutation 4
SEQ ID NO 17 human LH3 cDNA nucleotides 1-2745, amino acids 1-738
SEQ ID NO 18 human LH3 amino acid sequence
SEQ ID NO 19 human LH3 nucleotides 1027-1284
SEQ ID NO 20 human LH3 amino acids 271-356
SEQ ID NO 21 human LH1 cDNA
SEQ ID NO 22 human LH1 amino acid sequence
SEQ ID NO 23 human LH2a cDNA
SEQ ID NO 24 human LH2a amino acid sequence
SEQ ID NO 25 human LH2b cDNA
SEQ ID NO 26 human LH2b amino acid sequence Nucleotide Sequences A nucleotide sequence encoding lysyl hydroxylase (LH) means within the scope of this invention a nucleotide sequence from any possible source which is capable of encoding an enzyme activity of which biological function is equivalent to the enzyme activity of LH. The nucleotide sequence encoding LH may originate from any suitable source having this enzyme activity. Suitable sources are organisms having collagen or protein having collagenous domain or collagen-type protein, because these organisms generally also produce lysyl hydroxylase or it may be an organism not having the mentioned collagen proteins, but still producing lysyl hydroxylase. The origin may be a eukaryote having only one form of lysyl hydroxylase, such as C. elegans, which belongs to nematodes and metazoa or the origin may be an organism producing a lysyl hydroxylase isoform being a derivative of the ancestral lysyl hydroxylase, such as LH3 producing organisms. LH 3 may preferably be from mammalian origin, more preferably from human, bovine, porcine and/or from murine origin. The nucleotide sequence may be synthetic or at least partly synthetic.

The nucleotide sequences encoding lysyl hydroxylase isoforms which do not have glycosyltransferase activity are not within the scope of this invention. Such nucleotide sequences are for example those sequences which encode human LH1 and LH2, which are not closely related to the ancestral LH form and LH3, and which do not seem to encode glycosyltransferase activity in their natural form. However, when these nucleotide sequences are genetically modified to have glycosyltransferase activity they are within the scope of this invention.

By a nucleotide sequence encoding glucosyltransferase and/or galactosyltransferase activity is meant within the scope of this invention a nucleotide sequence encoding LH from any possible source as described above. The nucleotide sequence encoding LH may originate from any suitable source having this enzyme activity as described above.

The isolation and characterization of nucleotide sequences encoding mammalian LH3 are described in Valtavaara et al. (1998), Passoja et al. (1998) and Ruotsalainen et al. (1999). These methods can be applied for the isolation and characterization of any desired nucleotide sequence encoding LH.

A nucleotide sequence encoding glucosyltransferase and/or galactosyltransferase activity may mean any genetic material having that capability. It may be cDNA, mRNA, gene or part of a gene or a partly or completely synthetic gene sequence that encodes the same or a functionally equivalent nucleotide sequence or gene product. The nucleotide sequence encoding a functionally equivalent gene product may be a nucleotide sequence comprising a nucleotide sequence selected from the group consisting of:

(a) nucleotide sequences having at least the partial nucleotide sequence of any one of SEQ ID NO 1, SEQ ID NO 3, SEQ ID NO 5, SEQ ID NO 6, SEQ ID NO 8, SEQ ID NO 9, SEQ ID NO 10, and/or SEQ ID NO 17;
(b) nucleotide sequences encoding a polypeptide having at least the partial amino acid sequence of any one of SEQ ID NO 2, SEQ ID NO 4, SEQ ID NO 11, SEQ ID NO 12, SEQ ID NO 14, SEQ ID NO 15, SEQ ID NO 16 and/or SEQ ID NO 18;
(c) nucleotide sequences which differ from the nucleotide sequences of (a) and/or (b) due to the degeneracy of the genetic code;
(d) nucleotide sequences hybridizing under stringent conditions to a nucleotide sequence of (a), (b) and/or (c);
(e) nucleotide sequences encoding a polypeptide having an amino acid sequence which shows at least 60% identity, preferably at least 70% identity, more preferably at least 80%, most preferably at least 90% identity to the sequences contained in (b); and
(f) nucleotide sequences encoding a polypeptide having an amino acid sequence which shows at least 35%, preferably at least 40%, more preferably at least 50%, still more preferably at least 60%, most preferably at least 70%, still most preferably at least 80% identity to a sequence contained in SEQ ID NO 20.

The term "hybridization" in this context means hybridization under conventional hybridization conditions, preferably under stringent conditions such as described by, e.g. Sambrook et al. (1989).

As hybridization probe can be used nucleic acid molecules that have exactly or substantially the same nucleotide sequence as SEQ ID NO 19 encoding the amino acids 271-356 of human LH 3 or fragments of said sequence. Alternatively is used the entire nucleotide sequence encoding human LH3 (SEQ ID NO 17) or mouse LH3 (SEQ ID NO 1) or C. elegans LH (SEQ ID NO 3). The fragments used as hybridization probes can also be synthetic fragments obtained by conventional synthesis techniques, the sequence of which is substantially identical to that of the nucleic acid sequences of the invention. Once genes hybridizing to the nucleic acid sequences of the invention have been identified and isolated it is necessary to determine the sequence and to analyze the properties of the proteins coded for by said sequence.

The term "hybridizing nucleic acid sequence" includes fragments, derivatives and allelic variants of SEQ ID NO 1, 3 or 17 encoding an identical or substantially similar protein or a biologically active fragment thereof. Fragments are understood to be parts of nucleic acid sequences long enough to code for the described protein (or substantially similar protein) or a biologically active fragment thereof. The term "derivative" means in this context that the nucleotide sequences of these molecules differ from the sequences of the above-described nucleic acid molecules in one or more positions and are highly homologous to said sequence.

"% Identity" means here percentage of identical amino acids being present at corresponding positions when two amino acid sequences are aligned to give the maximal amount of identical nucleotides or amino acids at corresponding positions.

In the studies of Valtavaara et al. (1998) it has been shown that the overall identity in amino acid sequences between LH 3 and LH1 or between LH3 and LH2 is 59%. The identity between all lysyl hydroxylases is 47%. The similarity values between the isoforms are 83 and 85%, respectively. Over 80% identity in amino acid sequences (more than 10 amino acids) are found in certain parts of human lysyl hydroxylase 3. Less identity is seen in the region of amino acids 271-356 (nucleotide sequence SEQ ID NO 19, amino acid sequence SEQ ID NO 20) (32% identity between isoforms).

Altered nucleotide sequences which may be used in this invention include deletions, additions or substitutions of different nucleotide residues resulting in a sequence that encodes the same or a functionally equivalent nucleotide sequence or gene product. The nucleic acid product itself may contain deletions, additions or substitutions of amino acid residues, which result in a functionally equivalent subunit.

When the nucleotide sequence encoding LH is isolated it may be introduced into a suitable host organism being capable of expressing the nucleotide sequence. The sequence may be linked into an expression vector under a regulatory region capable of regulating the expression in a chosen host.

Expression Systems

Various methods known to the person skilled in the art can be used to construct expression vectors, which contain LH coding sequence and appropriate transcriptional/translational control signals. These methods comprise in vitro recombinant DNA techniques, synthetic techniques and in vivo recombination. Such techniques are described for example in Maniatis et al. 1989 and Ausubel et al. 1989.

A variety of host-expression vector systems may be used to express a nucleotide sequence encoding LH. These comprise microorganisms, such as bacteria transformed with recombinant plasmid DNA or cosmid DNA or bacteriophage DNA, expression vectors, fungi or yeast transformed with recombinant fungus or yeast expression vectors, animal cell systems infected with appropriate vectors, insect cell systems infected with recombinant virus expression vectors (e.g., baculovirus as exemplified in the examples), plant cell systems infected with recombinant virus or plasmid expression containing the nucleotide sequence encoding LH.

Additionally, the LH and/or glycosyltransferase coding sequence of the invention may be expressed in transgenic non-human animals wherein the desired enzyme product may be for example recovered from the milk of the transgenic animal. The LH and/or glycosyltransferase coding sequence may be expressed also in humans and used in gene therapy.

A number of suitable transcription and translation elements may be used in the expression vector depending on the host/vector system used. These include constitutive and inducible promoters. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters) or from plant viruses (e.g., the 35S RNA promoter of CaMV) may be used; when cloning in mammalian cell systems, promoters derived from the genome of mammalian cells (e.g., metallothionein promoter) or from mammalian viruses (e.g., the vaccinia virus 7.5 K promoter, the adenovirus late promoter;) may be used; when generating cell lines that contain multiple copies of the nucleotide sequence encoding LH, EBV-, BPV- and SV40-, based vectors may be used with an appropriate selectable marker.

In bacterial systems a number of expression vectors may be advantageously selected depending upon the use intended for the LH and/or glycosyltransferase expressed. For example, when large quantities of the polypeptides of the invention are to be produced, vectors which direct the expression of high levels of protein products that are readily purified may be desirable. Such vectors include for example certain *E. coli* expression vectors (Ruther et al. 1983, Inouye and Inouye 1985 and Van Heeke and Schuster 1989).

In yeast, a number of vectors containing constitutive or inducible promoters may be used (Ausubel et al. 1988). Preferred system useful for cloning and expression of the proteins of the invention uses host cells from the yeast *Pichia*, in particular *Pichia pastoris* and *Hansenula polymorpha*.

If plant expression vectors are used, the expression of sequences encoding the LH and/or glycosyltransferase of the invention may be regulated by a number of viral promoters. Viral promoters such as the coat protein promoter of TMV (Takamatsu et al. 1987 or 19S RNA and 35S RNA promoters of CaMV (Brisson et al. 1984),) may be used. These constructs can be introduced into plant cells using microinjection, electroporation, direct DNA transformation, Ti plasmids, Ri plasmids, plant virus vectors, etc.

Insect expression system may be an alternative expression system which could be used to express LH and/or glycosyltransferase of the invention as described in the examples.

In mammalian host cells, a number of viral based expression systems may be used such as an adenovirus expression vector.

For efficient translation of inserted LH and/or glycosyltransferase coding sequences specific initiation signals may be needed. These signals include the ATG initiation codon and adjacent sequences. The inclusion of appropriate transcription enhancer elements and transcription terminators, etc may enhance the efficiency of expression.

Transgenic non-human animals may be a preferred expression system for the recombinant production of the LH and/or glycosyltransferase of the invention, because the desired polypeptide may be recovered from the milk of the transgenic animal. The DNA sequence encoding the LH and/or glycosyltransferase may be operably linked to a promoter optionally together with other required or optional regulatory sequences capable of effecting expression in mammary glands.

Stable expression of the LH and/or glycosyltransferase product is preferred and hence, for example cell lines which stably express LH and/or glycosyltransferase may be engineered.

Preferably, the LH and/or glycosyltransferase of the invention is expressed as a secreted protein. When the engineered cells used for expression of the proteins are non-human host cells, it is often advantageous to replace the human secretory signal peptide of the LH with an alternative secretory signal peptide which is more efficiently recognized by the host cell's secretory system. The appropriate secretory signal sequence is particularly important in obtaining optimal fungal expression of mammalian genes.

It may be desirable to choose a host cell strain, which can modulate the expression of the inserted sequences, or modify and process the gene product in a desired way. Such modifications (e.g., glycosylation) and processing (e.g., cleavage) of protein products may be important for the function of the protein. Different host cells have characteristic and specific mechanisms for the post-translational processing and modification of proteins. To ensure the correct modification and processing of the foreign protein to be expressed suitable cell lines or host systems can be chosen. Eukaryotic host cells which possess the cellular machinery for proper processing of the primary transcript, glycosylation, and phosphorylation of the gene product may preferably be used. Such mammalian host cells include COS, CHO, HeLa, VERO, BHK, MDCK, 293, WI38, etc. However, glucosyltransferase and galactosyltransferase are active also in non-glycosylated form.

Identification of the Host Organisms Capable of Expressing LH and Glycosyltransferase Activity The presence of the enzyme coding sequence inserted in the expression vector can be detected by DNA-DNA or DNA-RNA hybridization using probes comprising nucleotide sequences that are homologous to the LH coding sequence, respectively, or portions or derivatives thereof. Alternatively in hybridization is used probes generated by PCR.

The recombinant expression vector/host system can be identified and selected by PCR by using oligonucleotides from inserted sequence. Alternatively the identification and selection can be based upon the presence or absence of certain "marker" gene functions (e.g., phenotype, resistance to antibiotics, occlusion body formation in baculovirus, etc.).

Furthermore, transcriptional activity of LH coding region can be measured by hybridization assays. RNA can be isolated and analyzed by Northern blot using a probe homologous to the LH coding sequence or particular portions thereof. Alternatively, total nucleic acids of the host cell may be extracted and assayed for hybridization to such probes.

The expression of the enzyme product can be assessed immunologically, for example by Western blots, immunoassays such as radioimmuno-precipitation, enzyme-linked immunoassays and the like.

The expressed enzyme of the invention, which can be isolated from the host cell extract, or if secreted into the culture medium, from the culture medium, is purified preferably to homogeneity. Nickel-affinity chromatography or other purification techniques known in the art can also be used, such as ion exchange chromatography, and reverse-phase chromatography.

The lysyl hydroxylase activity can be assayed by a method based on the hydroxylation-coupled decarboxylation of 2-oxo(1-$^{14}$C) glutarate (Kivirikko and Myllylä 1982), synthetic peptide IKGIKGIKG (SEQ ID NO: 27) was used as a substrate.

The glucosyltransferase activity can be assayed as described in Myllylä et al. (1975). The method is based on the transfer of radioactively (tritium) labelled glucose from UDP-glucose to galactosylhydroxylysyl residues in calf skin gelatin substrate and on the specific assay of the product of the enzyme reaction after alkaline hydrolysis.

In order to detect or produce galactosyltransferase activity, similar genetic constructions are prepared as were prepared to detect or produce glucosyltransferase activity. Alternatively the genetic constructions are modified for example to produce the polypeptide as a dimer or comprise a factor facilitating the purification of the enzyme.

The galactosyltransferase activity can be assayed as described in Myllylä et al. (1975). The method is based on the transfer of radioactively (tritium) labelled galactose from UDP-galactose to hydroxylysyl residues in calf skin gelatin substrate and on the specific assay of the product of the enzyme reaction after alkaline hydrolysis.

Genetic Modification of a Nucleotide Sequence Encoding LH and Glycosyl-transferase Activity By the genetic modification of a nucleotide sequence encoding LH, which results in partial or complete loss of lysyl hydroxylase activity is meant any genetic modification which has similar effect to the activity of the protein. The genetic modification may be made by any suitable conventional or molecular biology method well known in the art. The modification is preferably made by recombinant DNA techniques, such as by site directed mutagenesis or deletion.

Genetic modification of a nucleotide sequence encoding lysyl hydroxylase, which results in partial or complete loss of lysyl hydroxylase activity is exemplified here by making genetic changes to the nucleotide sequence encoding human LH3. The modification may comprise a deletion at the carboxy terminus. In particular the modification may comprise a deletion of about 200 amino acids, in particular the deletion of 218 amino acids from the carboxy terminus.

Furthermore the modification may comprise a genetic change resulting in a nucleotide sequence which encodes a changed amino acid at a certain position or positions. Here we have shown that a genetic change resulting in alanine instead of aspartic acid at position 669 of the amino acid sequence removes the lysyl hydroxylase activity of the protein.

By the genetic modification of a nucleotide sequence encoding LH and glycosyltransferase activity, which results in partial or complete loss of glycosyltransferase activity is meant any genetic modification which has similar effect to the activity of the protein. The genetic modification may be made by any suitable conventional or molecular biology method well known in the art. The modification is preferably made by recombinant DNA techniques, such as by site directed mutagenesis or deletion.

If the sequence is modified such that the molecule consists of only 231 amino acids of human LH3 sequence, the protein has no GGT or GT activity. This result indicates that the amino-terminal portion of the molecule is not sufficient to generate the GGT or GT activity.

The genetic modification of a nucleotide sequence encoding LH, may mean also any genetic modification of nucleotide sequences encoding LH, but not glycosyltransferase, such as nucleotide sequences encoding LH1 and LH2, which results in the expression of glycosyltransferase activity. Such genetic modification may be made by any suitable conventional or molecular biology method well known in the art. The modification is preferably made by recombinant DNA techniques, such as by site directed mutagenesis or deletion. As an example, the modification may be directed to those nucleotides encoding amino acids differing from the amino acids of LH3. The modification may preferably comprise modification directed to the nucleotide sequence corresponding to human LH3 cDNA encoding the amino acids 271-356 (SEQ ID NO 19).

The Production and Use of Glycosyltransferase

Glycosyltransferase enzyme is produced by expressing a nucleotide sequence encoding lysyl hydroxylase in a suitable host organism as described above. The enzyme may be recovered and isolated from the culture medium or cell extract by conventional methods and preferably purified to homogenity. In a preferred embodiment of this invention the nucleotide sequence encoding lysyl hydroxylase is modified to encode a factor facilitating the purification of the enzyme, for example an amino acid sequence tag, such as His-tag. This amino acid sequence tag is able to bind to the affinity column in affinity chromatography. As an example we have prepared a nucleotide sequence encoding a polypeptide comprising His-tag, which binds to nickel-affinity column. This construction remarkable facilitates the purification of glucosyltransferase.

In connection of this invention it was found out that in order to be active lysyl hydroxylase should appear as a dimer, whereas glucosyltransferase and galactosyltransferase appears to be active as a multimer and monomer. Accordingly, genetic constructions are prepared which encode an active enzyme.

Enzymes having glucosyltransferase and/or galactosyltransferase activity are used for glycosylating hydroxylysine residues in polypeptides or peptides having these residues. Such residues are for example in collagen, in collagenous or collagen-type or in other proteins or in synthetic or in partly synthetic polypeptides of peptides. The glycosylation reaction is carried out in the presence of additives and factors necessary for the function of the enzyme, such as buffers, cofactors and glycosylresidues, such as UDP-glucose or UDP-galactose. For example a suitable buffer for glucosyltransferase (or galactosyl-transferase) is 0.1 M NaCl, 0.05-1 mM dithiothreitol and 50 mM Tris-HCl, pH 7.4 (at 20° C.), Mn is used as cofactor and UDP-glucose (or UDP-galactose) as sugar residue.

Production of LH, GGT and GT Activity

In the examples we have exemplified the production of LH, GGT and GT activity in eucaryotic and virus expression systems.

As described in the examples, we have shown in baculovirus and eucaryotic expression systems that the expression of LH3 cDNA produced both LH activity and GGT activity. The appearance of the activities in the cells occurs simultaneously, without any lag between the activities which might suggest that expression of LH caused the simultaneous induction of the transcription of the GGT gene. When LH3 was expressed with a His tag at the amino-terminus, the protein with GGT activity bound to the nickel affinity column, and eluted by imidazole indicating that the GGT activity is present on the protein having his-tag in its structure. Immunoblot analysis of the eluate indicated that the protein purified by the affinity column corresponds in size to the recombinant LH3. Results from cell free translation experiments further support the finding that LH and GGT activities are coming from the same protein. Since only one protein corresponding to the size of LH3 is translated in the cell free system supplemented with the LH3 cDNA sequence, and GGT activity is present after translation, this protein has GGT activity.

Upon overexpression of LH3 in insect cells, most of the activity is retained inside the cell, only about 35% of the activity being secreted, however. It should be noted, however, that at later time points, the relative proportion of the activity of the medium increased, probably due to lysis of the cells. In Cos-7 cells, the majority of the GGT activity was secreted into the medium, when followed 48 hours after the transfection. Microscopic examination revealed, that in some cells the protein was retarded in the endoplasmic reticulum, an agreement with the data obtained with LH1 (Kellokumpu et al., 1994). It is probable that overexpression of the protein overloads the retention capacity and therefore the protein starts to be secreted into the medium. This was seen in microscopy by the appearance of fluorescent signals in Golgi complex. A difference in the amount of secretion between insect cells and Cos-7 cells can be explained by different capacities of the cells to retain proteins in the ER, but it may be also due to the fact that the total expression of LH3/GGT per cell is higher in Cos-7 cells than in insect cells.

The molecular weight of human LH3 corresponds to about 85,000 in SDS-PAGE (Passoja et al., 1998). GGT isolated from chick embryos has a molecular weight of 78,000 (Myllylä et al., 1976). It is not known, if there are many GGTs in vivo, and it is also not known, if the molecular weight of GGT differs in different species. It is also possible that there is a difference in a glycosylation of the protein produced in vitro expression system compared to the protein isolated from tissues. Only one size protein is produced by LH3 cDNA in insect cells and Cos-7 cells. Furthermore, only one protein is produced in a cell free system supplemented with LH3 cDNA sequence. In all these systems the protein has the molecular weight of about 85,000, which corresponds to the molecular weight of LH3.

These data indicate, that no processing of LH3 is required to generate the GGT activity. Our data with the anti-His-tag antibodies against the His-tag present at the amino-terminus of LH3 and with anti GFP antibodies against the GFP-tag present at the carboxy-terminus of LH3 do not indicate that there are multiple forms of LH3 in cells. Furthermore, our screening from different tissues does not give any evidence about alternative splicing for LH3 mRNA.

We have prepared polyclonal antibodies against synthetic peptide corresponding to amino acids 283-297 of human LH3 sequence (Wang et al., 2000), a region, which is highly dissimilar between lysyl hydroxylase isoforms. Antibody binding to that region of the LH3 molecule partially inhibited GGT activity. We also used antibodies, which were prepared against GGT isolated as a homogenous protein from chick embryos. The binding sites of these antibodies are not known, but as observed earlier (Myllylä, 1981), these antibodies inhibited chick embryo GGT activity. The binding of the antibody partially is prevented binding of the substrate and the inhibition was more effective when tested with high molecular weight substrate (Myllylä, 1981). When antibodies were tested with the enzyme produced by the human His-tagged LH3 construct in Sf9 cells, a similar inhibition of the GGT reaction was observed. The data obtained by LH3 and GGT antibodies are in agreement with the suggestion that LH3 is identical to GGT. GGT antibodies furthermore suggest a similarity of binding sites of the antibodies between chicken and human enzymes. These antibodies were also tested with GGT produced by human skin fibroblasts, and as seen in Table II, the LH3 and GGT antibodies showed similar inhibition of GGT under in vivo conditions.

We have indicated also the third function for lysyl hydroxylase, the galactosylation of hydroxylysyl residues in collagens. Thus we have shown that the same gene, *C. elegans* lysyl hydroxylase gene or human LH3, is able to hydroxylate lysyl residues, galactosylate the hydroxylysyl residues and glucosylate the galactosylhydroxylysyl residues, the consecutive steps needed to build hydroxylysine linked carbohydrates in collagens. A trifunctional character for a protein is not a common feature, but it is found for example in enzymes involved in lipid metabolism as well as in purine and pyrimidine metabolisms.

*E. coli* expression system was used to produce GT activity from LH3 cDNA. High activity was found in the supernatant of the transfected cells indicating *E. coli* system suitable to recognize GT as well as GGT activity from human LH3 or *C. elegans* cDNA. Most of the LH3 molecules can be found in insoluble form, however, and this insoluble fraction contained only a part of the enzyme activity and therefore was not studied further. The GT activity of the soluble fraction of the expression system was eluted in a gel filtration in the similar profiles, GT profile following the activity of GGT. Two activity peaks were observed in the elution, the main activity peak corresponded to a molecular weight of about 20-30 kDa and the minor peak to about 70-100 kDa, when compared with elution positions of globular standards. The data suggest the enzyme activities to be adsorbed to a column resulting in a retarded elution. Similar retardation phenomenon in a Bio-Gel A 1.5, Sephadex G-150 and Sephadex G-100 columns has been reported when studied GGT isolated from chick embryos (Myllylä et al. 1976 and 1977). It is worth noticing a small difference of retardation between GT and GGT activities, however.

It is remarkable to notice that no LH activity can be found in E. coli expression system, when human LH1, LH2a, LH2b or LH3 was used as cDNA of the expression vector (data not shown), although the LH activity have been found in a baculovirus system with these cDNAs (Valtavaara et al. 1997, 1998, Passoja et al. 1998, Yeowell and Walker 1999). The data obtained from Bio-Gel A 1.5 column indicate that the elution position of LH activity, isolated from chick embryos, corresponded to the molecular weight of about 200 kDa (Turpeenniemi-Hujanen et al. 1980) suggesting a dimer structure for LH. Furthermore, other data indicate that LH1 exists as a homodimer of identical subunits and mutation of cysteine residues does not inhibit non-covalent dimerization of LH1 (Yeowell et al. 2000). No higher molecular weight compounds was observed when human LH3 expressed in E. coli system was analyzed in gel filtration. It may be that LH dimerization required for LH activity is not occurring in E. coli system by the unknown reason, or the molecules having higher molecular weight like dimers form the insoluble precipitate found in the cell pellet, which could explain the lack of LH activity in our experiments. Furthermore, it is known that treatment of LH 1 with endoglycosidase H (Myllylä et al. 1988) and mutation of the glycosylated asparagine of LH1 (Pirskanen et al. 1996) reduced the enzyme activity indicating that the N-glycosylation, which is known to be defective in E. coli cells (Coligan et al. 1995), is important for LH activity. GT and GGT activities are found in our experiments in E. coli cells supplemented with human LH3 or C. elegans LH cDNA, indicating that the cDNAs are producing glycosyltransferases and furthermore suggesting that asparagine linked glycosylation is not required for the activities of the glycosyltransferases.

GT activity could also be found in Sf9 cells infected with baculovirus vector containing human LH3 cDNA. It is noteworthy to recognize that Sf9 cells contain the endogenous GT activity, although there is a lack of GGT activity in these cells. It is also interesting to find that the activity ratio of GT to GGT of the LH3 derived protein is lower in insect cells compared with the data from E. coli cells. The reason for that is not known but it may be due to difference in protein folding or post-translational modification, being the GT activity's favor in bacterial conditions. It is also interesting to notice that in vitro translation of LH3 produces the active GGT, whereas a small amount of activity was recognized in GT assay, after addition of microsomes to the translation mixture. Furthermore, imidazole inhibited GT activity efficiently in the contrary to the mild inhibition of GGT, and there was a small difference in the retardation affinity on gel filtration column between GT and GGT. These data suggest a difference in the behaviour of the glycosyltransferases.

Mutation of the Nucleotide Sequence Encoding LH3

Our mutation analysis gave a direct evidence that amino acid sequence translated from LH3 cDNA sequence is required, and is sufficient, for the GGT and GT activity. If we modified the sequence such that the molecule consisted of only 231 amino acids of LH3 sequence, the protein has no GGT nor GT activity. This result indicated that the amino-terminal portion of the molecule was not sufficient to generate the GGT nor GT activity. Mutation of aspartate at position 669 to alanine totally eliminated LH activity. This change, however, has no effect or even slightly stimulatory effect on the GGT or GT activity, indicating that this amino acid residue is not involved in the catalytic process in the glycosylation reaction. The aspartate to alanine mutation has been indicated to reduce also LH1 activity dramatically and indicates that aspartate 669 is a part of active site of LH1 (Pirskanen et al., 1996). LH1, LH2 and LH3 have a high homology in amino acid sequences, this holds true especially at the carboxy-terminal region of the molecules (Passoja et al., 1998; Valtavaara et al., 1998). Our mutation analysis confirmed that C-terminus was the important region for the LH activity (Hautala et al., 1992; Pirskanen et al., 1996). Interestingly, removal of carboxy-terminal end of the molecule does not totally eliminate the GGT nor GT activity suggesting that the active center of GGT or GT is not co-localising with that of LH. This is also indicated by the finding that imidazole, a histidine analogue, effectively inhibited LH3 activity whereas only a slight inhibition in GGT activity was observed, inhibition of GT activity being between these two. This may be explained by the finding that many conserved histidines in the carboxy-terminal portion of the molecule are required for the LH activity, as indicated in LH1 by in vitro mutagenesis (Pirskanen et al., 1996), and imidazole probably prevents their participitation in the catalytic process. Histidines do not appear to be necessary for GGT activity, however, and therefore imidazole does not inhibit GGT.

There is overall 60% identity between LH isoforms at the amino acid level (Hautala et al., 1992; Valtavaara et al., 1997, 1998; Passoja et al., 1998, Ruotsalainen et al., 1999). The carboxy-terminal portion of the molecule is highly conserved in all three lysyl hydroxylases. In addition, there are regions in the middle of the molecule, which have an identity over 80%. It is remarkable to find that only LH3, not LH1, LH2a or LH2b, possesses GGT and GT activity. It is possible that regions having less identity between LH isoforms, such as amino-terminal end of the molecule and a region covering amino acids 271-356, are responsible for GGT and GT activity of LH3.

The invention will be further understood by reference to the following examples, which are intended to be purely exemplary of the invention and not limited by scope by the exemplified embodiments.

EXAMPLES

Example 1

Materials and Methods

Cell Culture and Transfection

Sf9 (*Spodoptera frugiperda*) insect cells were grown in Sf-900 II Serum Free medium (Life Technologies, Inc.). Expression of recombinant protein was carried out by baculovirus transfer vector (Gruenwald and Heitz 1993, Luckow et al. 1993) in the BAC-TO-BAC Expression system (Life Technologies, Inc.).

Cos-7 cells were grown at 37° C./5% $CO_2$ in DMEM containing 10% newborn calf serum. $8\times10^5$ cells per 100 mm dish or $1\times10^5$ cells per 35 mm dish were plated one day before transfection. Cells were transfected by plasmid DNA using FUGENE6 (Boehringer Mannheim). After incubation of cells 0-48 hours the cells were harvested and washed twice with PBS.

Expression of LH3 cDNA in Insect and Eucaryotic Cells

Commercially available baculovirus transfer vector pFastBacI in the BAC-TO-BAC™ expression system (Life technologies, Inc.) was modified to contain human LH1 signal peptide (Hautala et al., 1992) and $His_6$ tag, and BamHI restriction site for insertion of the desired cDNA, nucleotides 289-2455 of LH3 cDNA (SEQ ID NO 6) (Valtavaara et al., 1998). The construct was confirmed by sequencing. The recombinant protein contains His tag at the amino-terminus after signal peptide cleavage. Insect cells were harvested 0-72 hours after infection and homogenized according to the protocol described earlier (Valtavaara et al., 1997).

Expression of LH3 cDNA was carried out also in eucaryotic expression vector as a LH3 and as LH3-GFP fusion protein. Human LH3 coding sequence covering the nucleotides from 214 to 2447 (SEQ ID NO 5) (Valtavaara et al., 1998) was subcloned into BamHI and XhoI sites of pCDNA3 vector (Invitrogen) and expressed in Cos-7 cells. The coding sequence was also subcloned into EcoRI site of pEGFP-N1 vector (Clontech), where GFP tag forms the C-terminus of the fusion protein. The intervening stop codon (TGA) of LH3 was mutated to TGG (trp) by changing $A_{2443}$ to $G_{2443}$ using QuickChange Site-Directed Mutagenesis Kit (Stratagene). In order to keep the reading frame for GFP, $T_{2447}$ was simultaneously deleted from the sequence (SEQ ID NO 5). The transfected Cos-7 cells were sonicated for 10 sec in ice into a solution of 0.1% Triton X-100, 0.2M NaCl, 20 mM Tris-HCl, pH 7.5, a supernatant of the centrifugate (14,000 rpm×30 min) was used in activity measurements.

Expression of LH1 and LH2 cDNA in Insect Cells

Human LH1 signal peptide and $His_6$ tag was inserted to the cDNA constructs of LH1 and LH2. The baculovirus transfer vector pFastBacI was modified so that human LH1 signal sequence followed by nine nucleotides of the amino-terminal end was ligated to the $His_6$ tag followed by nucleotides for BamHI restriction site. The human cDNA sequence (LH1 or LH2) (SEQ ID NO 21, 23 and 25) starting from the likely amino-terminal end of the molecule was ligated to the BamHI site of the construct. Two expression constructs were generated for LH2, LH2a and LH2b (SEQ ID NO 23 and 25), both of them covered the nucleotides from 76 to 2267 (Valtavaara et al., 1997). The LH2b construct contained also the alternatively spliced exon sequence (Valtavaara 1999; Yeowell and Walker, 1999) between nucleotides 1500 and 1501 (SEQ ID NO 25). The constructs were confirmed by sequencing. Insect cells were grown and homogenized as described above.

Purification of His-tagged Proteins by Nickel Column

His-tagged recombinant proteins were purified by Ni-NTA Agarose (Qiagen) using batch purification protocol as described by the manufacturer. The agarose was equilibrated with 20 mM Tris-HCl, pH 7.8, 0.3 M NaCl, 5% glycerol and 10 mM imidazole. Ni-NTA Agarose was mixed into the cell homogenate with additions of 5% glycerol, 0.3 M NaCl and 10 mM imidazole, and the slurry was incubated for 45 min at 4° C. on a rocking platform, the matrix was washed in a buffer of 20 mM Tris-HCl, pH 7.8, 0.3 M NaCl, 5% glycerol and 20 mM imidazole. Elution (incubation of matrix for 10 min in a elution buffer) was carried out in three steps: the elution buffers contained 100 mM, 200 mM and 300 mM imidazole, respectively.

Microscopical Studies

In order to follow expression of LH3-GFP fusion protein in Cos7 cells, the cells transfected with pEGFP-N1-LH3 plasmid DNA were grown-on coverslips. Fourty-eight hours after transfection cells were washed twice with PBS and briefly rinsed in distilled water. The coverslips were mounted on slides using Immuno-mount (Shandon). The expression levels of LH3-GFP fusion protein were visualized directly by fluorescence microscope (Nikon).

The transfected cells were also stained with antibody against protein disulphide isomerase (Höyhtyä et al., 1984). The cells were fixed with 4% paraformaldehyde in PBS pH 7.4 for 20 min, blocked for 1 h in 0.05% Saponin, 0.1% BSA in PBS buffer pH 7.4 (IF buffer), followed by 1 hr incubation at room temperature with a monoclonal antibody (1:100) against protein disulphide isomerase (DAKO). Coverslips were washed three times with IF buffer, and incubated for a further 1 hr with an anti-mouse IgG TRITC conjugate (1:100) (DAKO). After three washes with PBS and one brief rinse in distilled water, coverslips were mounted on slides by Immuno-mount. Staining was checked under fluorescence microscope.

Immunoprecipitation

Cells transfected with LH3 construct or vector alone were lysed with 5 mM EDTA, 0.5% Triton X-100 in PBS for 30 min at 4° C. Cell extract was pretreated with protein A sepharose CL-4B (Pharmacia) to remove nonspecific binding and then immunoprecipitated with GFP monoclonal antibody (Clontech) or His tag antibody (Sigma) together with protein A sepharose CL-4B beads. The proteins bound to beads were analyzed by SDS-PAGE and immunoblotting or silver staining.

In Vitro Translation

For in vitro translation coding sequence (amino acids 33-738) of LH3 cDNA (SEQ ID NO 17 and 18) was cloned in frame into pCITE 4a vector (Novagen) at EcoRI/XhoI site under T7-promoter. This vector provides the transcribed mRNA with cap independent translation enhancer at 5' end and a poly(A) tail. This vector produces a translated protein with 6× His tag at the carboxy-terminus of the protein. Plasmid was subcloned into E. coli XL1-blue strain and purified with Mini Plasmid Kit (Qiagen). In vitro translation was performed with single tube protein system 3 kit, STP3 (Novagen) according to manufacturer's protocol. Reaction volumes were scaled down. Briefly, for transcription 200 ng of plasmid were mixed with 3.2 µl of transcription mix in a total volume of 4 µl and incubated at 30° C. 15 minutes. For translation 1.6 µl of $^{35}$S-methionine (10 mCi/ml, Amersham) or 0.8 µl of cold methionine in the kit and 12 µl of translation mix were added into transcription reaction and incubated at 30° C. for an hour. Product was analyzed on SDS-PAGE and autoradiography and GGT activity was measured directly in the reaction mixture containing unlabelled methionine.

Activity Measurement

LH activity was assayed by a method based on the hydroxylation-coupled decarboxylation of 2-oxo(1-$^{14}$C)glutarate (Kivirikko and Myllylä 1982), synthetic peptide IKGIKGIKG (SEQ ID NO: 27) was used as a substrate. GGT activity was assayed as described elsewhere (Myllylä et al. 1975). The method is based on the transfer of radioactively (tritium) labeled glucose from UDP-glucose to galactosylhydroxylysyl residues in calf skin gelatin substrate and on the specific assay of the product of the enzyme reaction after alkaline hydrolysis.

Other Assays

Western blot analysis was carried out using a monoclonal antibody against His-tag (Sigma) or GFP protein (Clontech). The homogenate of the cells were fractionated in reducing conditions by SDS/10% PAGE, blotted an Immobilon membrane (Millipore) and incubated with the antibodies. Bound antibodies were visualized using the ECL detection system (Amersham Life Science, Inc.) and x-ray film (Eastman Kodak Co). Anti-Mouse IgG peroxidase conjugate (Sigma) was used as secondary antibody.

The QuickChange site-directed mutagenesis kit (Stratagene) was used to make point mutations or deletions to LH3 cDNA sequence. Antibodies used in this study were the following: polyclonal anti-rabbit antibodies against highly purified GGT isolated from chicken embryos (Myllylä, 1981), polyclonal anti-chicken antibodies against a synthetic peptide of human LH3 (Wang et al., 2000), monoclonal anti-mouse antibodies against His-tag (Clontech) and rabbit polyclonal antibodies against the human Dpb11 protein (T. Hillukkala and M. Mäkiniemi, unpublished).

Example 2

Collagen Glucosyltransferase Activity in Cells Transfected with LH3 cDNA

We have prepared a cDNA construct of LH3 for expression of an LH3 protein with a His-tag, which remains at the amino-terminal end of the protein after signal peptide cleavage. Sf9 cells were infected with this construct, and LH and GGT activity were measured in the cells at different time points (FIG. 1A). As seen in the figure, the enzyme activities began to increase about 30 h after transfection. At this same time we could begin to detect GGT activity in the culture medium. We were unable to measure LH activity, however, due to the presence of inhibitory substances in the medium (Krol et al., 1996). The rapid increase of GGT activity in the medium, approximately 50 h after transfection, seen in FIG. 1A, was probably due to cell lysis due to the infection.

Figure 1B:
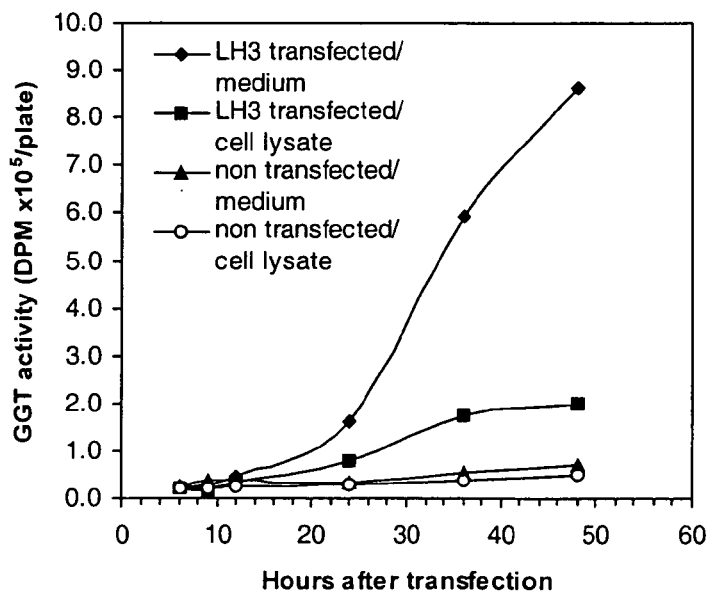

We tested the transfections also in mammalian cells, where native LH3 cDNA was used in the transfections (FIG. 1B). A similar time curve for GGT activity was obtained in these cells. When the transfected Cos-7 cells were studied at different time points by Northern hybridization using LH3 cDNA as a probe, the data indicated a clear increase in LH3 mRNA 20 hours after transfection (not shown).

The results presented in Table I indicate the activities measured in one experiment. There is a large increase in GGT activity in the LH3 cDNA transfected Sf9 and Cos-7 cells. The increase is higher in the Sf9 cells, varying from about 120 to 2500 times the background activity in different transfections. Nontransfected Cos-7 cells possess high GGT activity, but after transfection the activity increased to about four to five times the background level. Expression of LH3 in both systems resulted in secretion of enzyme into the medium (Table I). In Sf9 cells, about 25 to 55% of the activity was secreted, whereas in Cos-7 cells the corresponding value was about 80%.

TABLE I

GGT activity in Sf9[1] and Cos-7[2] cells transfected with LH3 cDNA constructs

| | GGT activity[3] (dpm/plate) | | |
|---|---|---|---|
| | Cells | Medium | % in medium |
| Sf9 cells | | | |
| Nontransfected | 1 000 | 5 000 | n.d. |
| LH3 transfected | 2 000 000 | 12 000 000 | 35 |
| Cos-7 cells | | | |
| Nontransfected | 72 000 | 69 000 | 48 |
| LH3 transfected | 270 000 | 1 200 000 | 82 |

[1]Sf9 cells were transfected with a construct containing signal peptide of LH1 and His-tag at the amino-terminus of LH3 protein. One plate corresponds to about $10 \times 10^6$ cells. n.d. not determined.
[2]Cos cells were transfected with the construct containing the LH3 including the signal peptide sequence of LH3 (see Material and Methods, Example 1). One plate corresponds to about $1.4 \times 10^6$ cells.
[3]The activity measurements were carried out 72 h (Sf9 cells) and 48 h (Cos-7 cells) after transfection.

Example 3

Intracellular Distribution of Protein Produced by LH3 cDNA

We prepared a construct for a LH3-GFP fusion protein in which GFP, a fluorescent protein, was inserted into the carboxy-terminal end of LH3. The cells transfected with the construct produced a fusion protein, which can be visualized by fluorescence microscopy. The fusion protein was located mainly in the endoplasmic reticulum. In some cells, the fluorescent protein also entered the Golgi complex (not shown) in agreement with the finding that a part of the expressed protein was secreted. When the activity measurements were carried out 48 hours after transfection, the results indicated a two-to three-fold increase of GGT activity in cells (not shown) suggesting the correct three-dimensional conformation of the LH3-GFP fusion protein for the catalysis in the GGT reaction.

Example 4

Purification of the LH3 Protein with a Tag at the Amino-terminal and Carboxy-terminal End LH3 was expressed in Sf9 cells as a protein with His-tag at the amino-terminus. This enabled us to use nickel column in the purification of the protein from the cell extract of insect cells, because nickel-charged agaroses are developed for the purification of recombinant proteins containing a polyhistidine (6×His) as a tag. Our results indicated that 60% of the GGT activity was bound to the nickel column and all the activity could be eluted out from the column by imidazole. No lysyl hydroxylase activity could be detected in the eluate, however. We have determined that imidazole is a potent inhibitor of lysyl hydroxylase activity. Incubation of His-tagged LH3 for 2 h on ice in the presence of 300 mM imidazole caused almost complete inactivation of the enzyme. Imidazole in the concentration of 100 mM and 10 mM inactivated lysyl hydroxylase activity by 55% and 20%, respectively. In contrast, imidazole in concentrations ranging from 10 mM to 100 mM had no effect on GGT activity, but 300 mM imidazole inhibited GGT activity by 25% (not shown).

The column eluate of the column was analyzed by SDS-PAGE and immunostained by using His-tag antibody in the Western blot. One major band was present on the blot, with a molecular weight of about 85,000 (FIG. 2A). Furthermore, immunoprecipitation of crude Sf9 lysate was carried out by His-tag antibodies, and the precipitate was analyzed by SDS-PAGE and silver staining. Only one protein band with a molecular weight of about 85,000 (FIG. 2B), in addition to immunoglobulin light and heavy chains, was present in the precipitate.

We also used immunoprecipitation to purify the LH3-fusion protein in Cos-7 cells. The fusion protein contained GFP tag at the carboxy-terminal end of the protein. The anti-GFP antibody immunoprecipitated from Cos-7 cell lysate a protein which has a molecular weight of 116,000 (FIG. 2C). This size corresponds to the expected molecular weight of LH3-GFP fusion protein.

Example 5

Cell Free Translation of LH3 cDNA

Figure 3A:
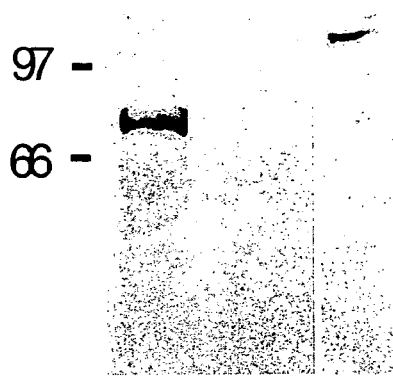
FIG. 3. Cell free translation of the LH3 construct. (A) Radioactively labelled proteins produced in a cell free translation system were analyzed by SDS-PAGE and autoradiography. Lane 1, LH3 cDNA; lane 2, no DNA added; lane 3, β-galactosidase cDNA as a control. Molecular size markers are indicated. (B) GGT activity (given as dpms above the column) produced in cell free translation system supplemented by LH3 cDNA. The activity value is a mean (±S.D.) of three different measurements, activity without any DNA supplement is shown as a background activity.
Figure 3B:
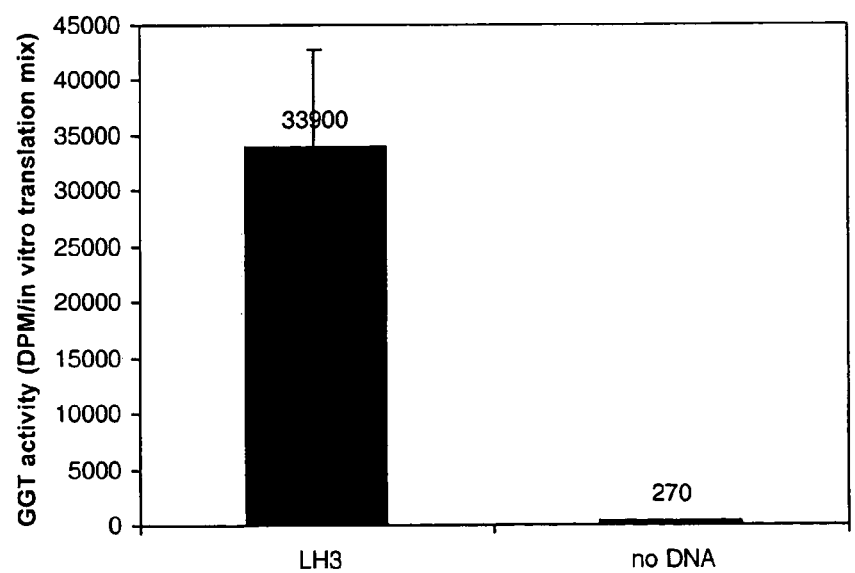

A cell free system can be used to study the expression of a supplemented DNA in a condition where no other DNA is present. The presence of radioactive amino acid allows detection of even low amounts of the protein expressed in the system. We have used the cell free system in order to rule out the possibility that a DNA sequence other than LH3 cDNA is responsible for the production of GGT activity. As seen in FIG. 3 only one protein (FIG. 3A) was translated in cell free system when LH3 cDNA was added to the incubation mixture. The molecular weight corresponds to that of LH3. Addition of dog pancreas microsomes to the incubation mixture does not change the molecular weight of the translated protein (not shown). The appearance of the protein in the expression was associated with the presence of GGT activity (FIG. 3B) indicating that GGT activity was linked to LH3 protein.

Example 6

Inhibition of GGT Activity by LH3 Antibodies and Antibodies Against Highly Purified Chicken GGT Polyclonal antibodies were used to study, whether the antibody binding inhibits the catalytic activity of the GGT produced by His-tagged LH3 cDNA construct in Sf9 cells. We used antibodies against a synthetic peptide corresponding to the amino acids 283 to 297 of human LH3 (SEQ ID NO 17 and 18) (Wang et al., 2000). In addition, we used antibodies against chicken glucosyltransferase isolated as a homogenous protein (Myllylä, 1981). As seen in Table II, both antibodies partially-inhibited the GGT activity. However, no inhibition by His-tag antibodies was detected. Antibodies against human Dpb11 protein were used as controls, and these antibodies had no effect on GGT activity.

The antibodies were also tested with GGT prepared from human skin fibroblasts. LH3 and GGT antibodies partially inhibited GGT activity from human skin fibroblasts (Table II), whereas no inhibition was obtained with anti-His antibodies or control antibodies.

TABLE II

Inhibition of GGT activity[a] in LH3 transfected Sf9 cells (Sf9/LH3) and human fibroblasts (FB) by different antibodies

| Antibody | Sf9/LH3 (%) | p-value | FB (%) | p-value |
|---|---|---|---|---|
| Nonimmune serum | 100 ± 7 |  | 100 ± 24 |  |
| LH3 | 84 ± 13 | 0.043 | 67 ± 22 | 0.046 |
| GGT | 84 ± 12 | 0.029 | 70 ± 3 | 0.043 |
| His-tag | 100 ± 6 | ns | 92 ± 23 | ns |
| Dpb11 | 101 ± 22 | ns | 108 ± 27 | ns |

[a]4 µl of serum was added to the GGT incubation mixture, the activity in the presence of nonimmune serum was taken as 100%, mean ± SD is expressed. Three to four samples were measured with each antibody. Statistical significance was calculated using two sample t-Test assuming equal variances.
ns, not significant.

Example 7

The Effect of Mutations in LH3 on the GGT Activity of the Protein

Figure 4A:
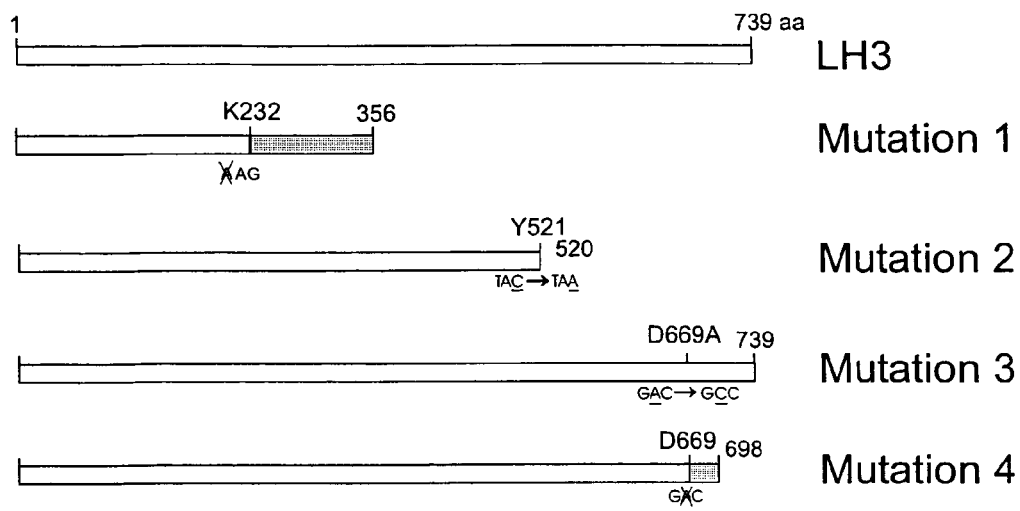
FIG. 4. Mutated LH3 constructs transfected in Sf9 cells. (A) Schematic picture of the locations and consequences of mutations in the LH3 construct. Numbers in the scheme indicate the position of the amino acids of the translated protein. Mutations of the sequence are also indicated. The amino acids translated after the frame shift are shaded. (B) The mutated proteins produced by Sf9 cells 72h after the transfections. The protein analysis was carried out by western blot using anti-His-tag antibody in the staining. Lane 1, mutation 1; lane 2, mutation 2; lane 3, mutation 3; lane 4, mutation 4; lane 5, LH3 without mutation; lane 6, Sf9 cell lysate.
Figure 4B:
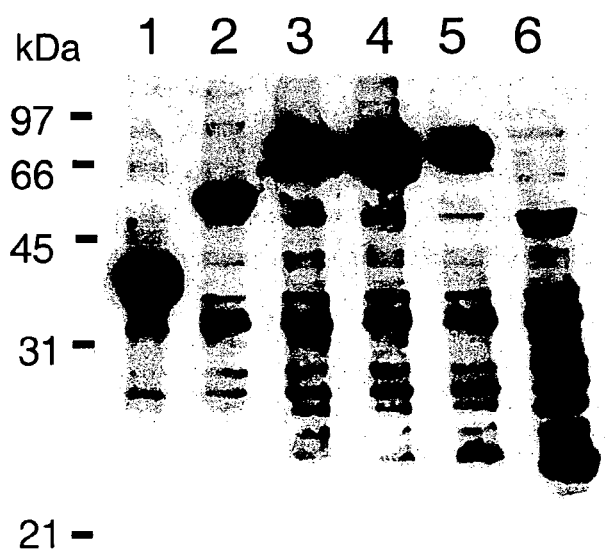

In order to see what regions of the molecule or which amino acids of LH3 are required for GGT activity, we generated a frame shift in the LH3 after leucine at position 231 by one nucleotide deletion (SEQ ID NO 7). This modification of the construct produced a protein of 356 amino acids (SEQ ID NO 13) (FIGS. 4A), where only the 231 amino acids were similar to LH3 sequence. This protein had neither LH nor GGT activity (Table III). Removal of 217 amino acids from the carboxy-terminus of LH3 inactivated LH activity totally, whereas the protein still retained about one fifth of the GGT activity (nucleotide sequence SEQ ID NO 8, amino acid sequence 14). Mutation of aspartate at position 669 to alanine decreased LH functionality dramatically, whereas it had no effect on GGT activity (nucleotide sequence SEQ ID NO. 9, amino acid sequence SEQ ID NO 15). One nucleotide deletion after the codon for His668 in the LH3 cDNA sequence caused a frame shift in the reading frame and generates a translational stop codon after 30 amino acids. In this protein the last 70 C-terminal amino acids of LH3 are missing from the molecule (nucleotide sequence SEQ ID NO 10, amino acid sequence SEQ ID NO 16). The protein had no LH activity but still retained about half of the original GGT activity. The FIG. 4B shows that the mutations did not cause any remarkable effect in the levels of protein expressions.

TABLE III

LH3 and GGT activity in Sf9 cells transfected by mutated LH3 constructs

|  | LH3 activity Dpm/plate | % | GGT activity Dpm/plate | % |
|---|---|---|---|---|
| LH3 construct, nonmutated | 6000 | 100 | 760 000 | 100 |
| Mutation 1 | <300 | <5 | 650 | 0.1 |
| Mutation 2 | <300 | <5 | 180 000 | 23 |
| Mutation 3 | <300 | <5 | 970 000 | 127 |
| Mutation 4 | <300 | <5 | 360 000 | 47 |

Figure 5:
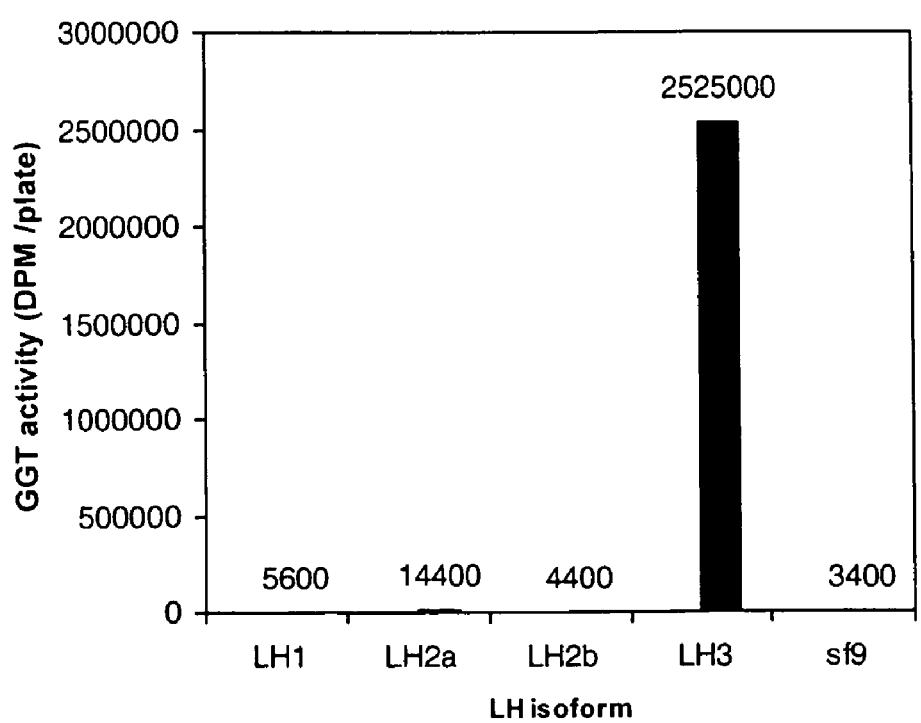
FIG. 5. GGT activity in different lysyl hydroxylase isoforms. All LH isoforms as His-tagged versions were produced in insect cells (see Example 8). GGT activity (given as dpms above the column) was measured in cell lysate 72 h after the transfections. Sf9 cell lysate was used as a control.

Mutations 1-4, see FIG. 5.
Similar results were obtained in three different measurements.

23

Example 8

Expression of LH1 and LH2 in Insect Cells do not Generate GGT Activity

The two other lysyl hydroxylase isoforms LH1 and LH2, the latter one in two alternatively spliced forms (LH2a and LH2b) (SEQ ID NO 23 and 25, respectively), were expressed in Sf9 cells in conditions identical to LH3. GGT activity was measured in cell lysates 72 hours after infection (FIG. 5). The production of recombinant proteins was followed by LH activity measurements and SDS-PAGE combined with His-tag antibody staining. The production of recombinant proteins was at the same level (not shown). Although LH activity was present in the cell lysates, none of these recombinant proteins had detectable GGT activity.

Example 9

In vitro Translation of C. elegans Lysyl Hydroxylase cDNA

The coding sequence of C. elegans lysyl hydroxylase cDNA (GenBank # CAA91321.1, starting from amino acid 14, SEQ ID NO 3) was amplified from C. elegans cDNA library (Stratagene) and cloned in frame into the pCITE 4a vector (Novagen) at the EcoRI/XhoI site under the T7-promoter. The plasmid was subcloned into E. coli XL 1-blue strain and purified. In vitro translation was performed with the single tube protein system 3 kit, STP3 (Novagen) according to manufacturer's protocol. For transcription, 200 ng of plasmid was mixed with 3.2 W of transcription mix in a total volume of 4 l and incubated at 30° C. for 15 minutes. For translation, 0.8 µl of cold methionine in the kit and 12 µl of translation mix were added to the transcription reaction and incubated at 30° C. for an hour. GGT activity was measured directly in the reaction mixture.

Example 10

Expression of LH3 cDNA in Insect Cells

Baculovirus transfer vector pFastBacI in the BAC-TO-BAC™ expression system was used to produce LH3 protein in Sf9 cells. The cDNA construct is in Example 1. The recombinant protein contains the His tag at the amino terminus after signal peptide cleavage. The cells were homogenized as described elsewhere (Valtavaara et a. 1997).

Expression of cDNA Constructs in E. coli

PFastBacI constructs for human LH1, LH2a, LH2b and LH3 were cleaved with BamHI and Hind III restriction enzymes and coding regions were subcloned into same site in E. coli expression vector pQE30 containing (His)$_6$ tag at the amino terminus. Insert for C. elegans LH (corresponding to amino acids 14-730 in cDNA) was generated by PCR and ligated into SacI-PstI site of pOE30 vector. Constructs were transformed into E. coli XL1-Blue strain. Cultures were grown to OD$_{600}$ of 0.6 at 37° C. Protein expression was induced by adding 1 mM IPTG and incubation was proceed at 30° C. for 5 hours. Cells were harvested and stored at −20° C. For activity measurements cell pellet was suspended to lysis buffer (0.4 M NaCl, 0.5% Nonident and 20 mM Tris-HCl pH 7.8, at 20° C.) and incubated in the presence of lysozyme (50 µg/ml), DNAase (10 µg/ml) and RNAase (10 µg g/ml) at room temperature for 30 minutes. Lysis was completed by sonication. Cell debris was pelleted and supernatant was used in the measurements.

24

Purification of His-tagged Proteins Expressed in E. Coli Cells by Nickel-NTA-AgarosE Recombinant proteins containing His-tag at their amino-terminal end were purified by Ni-NTA-agarose column (Qiagen). Purification protocol is described in the booklet of manufacturer. The agarose was mixed with soluble fraction of E. coli homogenate and incubated for 45 min at 4° C. with a solution containing 20 mM Tris-HCl, pH 7.8, 0.3 M NaCl, 5% glycerol, and 10 mM imidazole. The matrix was washed in the solution containing 20 mM imidazole. The elution was carried out in three steps: the elution buffers contained 100 mM, 200 mM and 300 mM imidazole.

Gel Filtration

The soluble fraction of E. coli homogenate was applied to a Bio-Gel A 0.5 column (0.79 cm×29 cm) or Sephacryl S-300 (0.79 cm×29 cm) equilibrated and eluted with a buffer containing 0.4 M NaCl, 1% glycerol, 20 mM Tris-HCl, pH 7.4. Fractions of 0.7 ml were collected and assayed for GT and GGT activity. Protein concentration was determined by measuring the absorbance at 280 and 260 nm using Biophotometer (Eppendorf). Apoferritin (Mw 443.000), amylase (Mw 200.000), albumin (Mw 66.000), carbonic anhydrase (Mw 29.000) and cytochrome C (Mw 12 400) were used as standards to estimate the molecular weight of the proteins responsible for the activities. For SDS-PAGE studies the fractions were precipitated with trichloroacetic acid.

In vitro Translation

The coding region of human LH3 cDNA (amino acids 33-738) or C. elegans LH cDNA (amino acids 14-730) was cloned in-frame into pCITE 4a vector (Novagen) at the EcoRI/XhoI site (human LH3) or SalI/NotI site (C. elegans LH) under the T7 promoter. In vitro translation reaction was performed as described here earlier. In some experiments 1.3 µl of canine pancreatic microsomes (Promega) was added into translation mixture to enhance translation of the product. GT and GGT activities were measured directly in the reaction mixture containing unlabeled methionine.

Activity Measurements

GT and GGT activities were measured by a method based on the transfer of radioactively (tritium)-labeled sugar from UDP-sugar to hydroxylysyl or galactosylhydroxylysyl residues in a calf skin gelatin substrate, respectively (Myllylä et al. 1975). The specific detection of the reaction products was performed after alkaline hydrolysis.

Other Assays

Protein concentration was measured using Biorad protein reagent in microassay and lysozyme as a control. Western blot analysis was carried out using monoclonal antibodies against His tag (Sigma). The cell supernatant was fractionated under reducing conditions on 10% SDS-PAGE, blotted onto an Immobilon membrane (Millipore) and incubated with the antibodies. Anti-mouse IgG peroxidase conjugate (Sigma) was used as a secondary antibody. ECL blotting detection reagents (Amersham Pharmacia Biotech) were used to detect the bound antibodies.

Collagen Glucosyltransferase and Galactosyltransferase Activities in E. coli Cells Transformed with C. elegans Lysyl Hydroxylase cDNA Construct We tested if the protein produced by LH cDNA would have the GT activity, the activity following LH activity and preceding GGT activity in formation of glucosylgalactosyl-hydroxylysyl residues in collagens. As seen in Table IV, native E. coli cells with only pQE30 vector as well as the cells expressing DHFR, which were used as controls, have only very low residual GGT or GT activity. When the *C. elegans* LH cDNA was used in the expressions, both GGT and GT activities were present in cell supernatant. GGT activity varied, which is due to different expression levels in various experiments, in a range from 8150 to 183.960 dpm/mg, the corresponding GT activity varied in a range from 12.300 to 159.400 dpm/mg. Similar results were obtained whether or not the expressing *E. coli* cells were stored frozen for up to two weeks at −20° C. or −70° C., before the activity measurements (not shown).

TABLE IV

GGT and GT activity in *E. coli* cells with *C. elegans* LH cDNA construct The cells were transfected with a construct containing the cDNA for LH without signal sequence. The cells were cultured in suspension, and after 5 h induction by adding 1 mM IPTG the cells were frozen and stored at −70° C. overnight. The homogenization was carried out as described here earlier, and the activities were measured in the supernatants.

| Cells | Enzyme activities (dpm/mg soluble protein) | |
|---|---|---|
|  | GGT | GT |
| LH cDNA, experiment I | 30.700 | 65.000 |
| LH cDNA, experiment II | 21.000 | 32.100 |
| DHFR cDNA | <300 | <1600 |
| *E. coli* cells with pQE30 vector, without any insert | <300 | <1600 |

Figure 12:
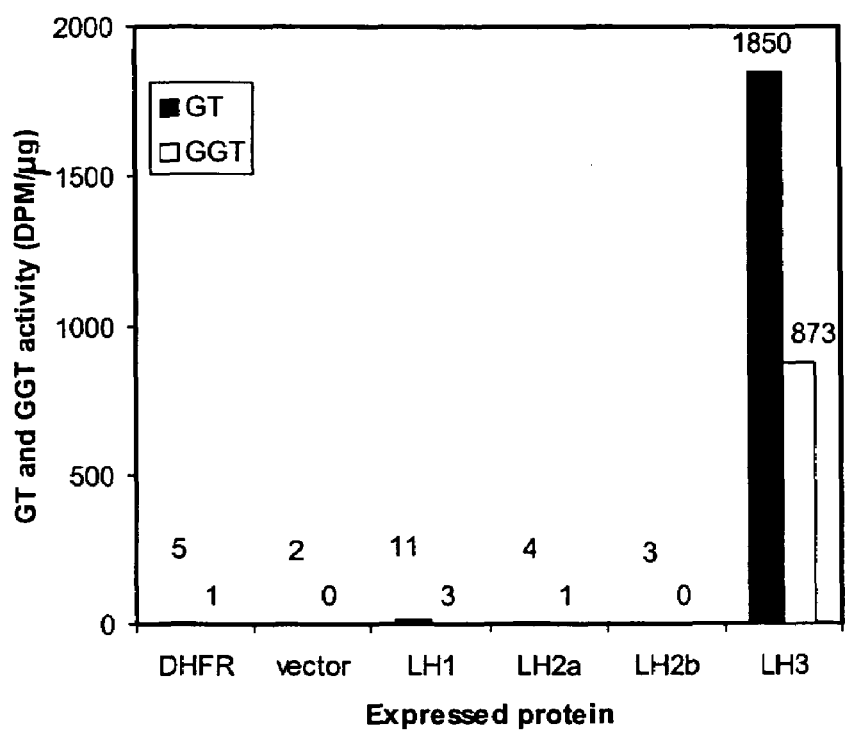
FIG. 12 shows GT activity in different human lysyl hydroxylase isoforms. Lysyl hydroxylase isoforms as His-tagged versions were produced in E. coli cells. The cells were grown for 5 hours at 30° C. after induction by IPTG, stored at –20° C. for up to one week and the cell supernatant was used in GT (black square) and GGT (open square) activity assay. The values (above the columns) are expressed per mg protein.

Human LH3, but not LH1, LH2a and LH2b, is Generating Galactosyltransferase Activity when Expressed in *E. coli* Cells Human LH isoforms; LH1, LH2 and LH3, LH2 in two alternatively spliced forms (LH2a, LH2b), were expressed in *E. coli* system, and GT as well as GGT activities were assayed from the cell supernatant. Immunostaining by His-tag antibodies indicated the presence of LH isoforms in the supernatant fraction, although the big part of recombinant proteins were found in the fraction of cell pellet (not shown). As seen in FIG. 12, LH3 was the only one being able to generate GT activity in *E. coli* cells. The samples were also tested (FIG. 12) in the GGT assay, and the data confirmed our earlier data obtained from baculovirus system that LH3 is the only one generating GGT activity. The data thus reveals that LH3 is a trifunctional protein capable to carry out all the steps in the formation of hydroxylysine linked carbohydrates of collagen: (i) hydroxylation of lysyl residues, (ii) galactosylation of hydroxylysyl residues and (iii) glucosylation of galactosylhydroxylysyl residues.

We also tested if GT and GGT activities can be found in the cell pellet. The pellet was suspended into the homogenization buffer and the suspension was used in the activity assays. The measurements revealed, that about 5% of GT and about 24% of GGT activity was present in the cell pellet.

Figure 13:
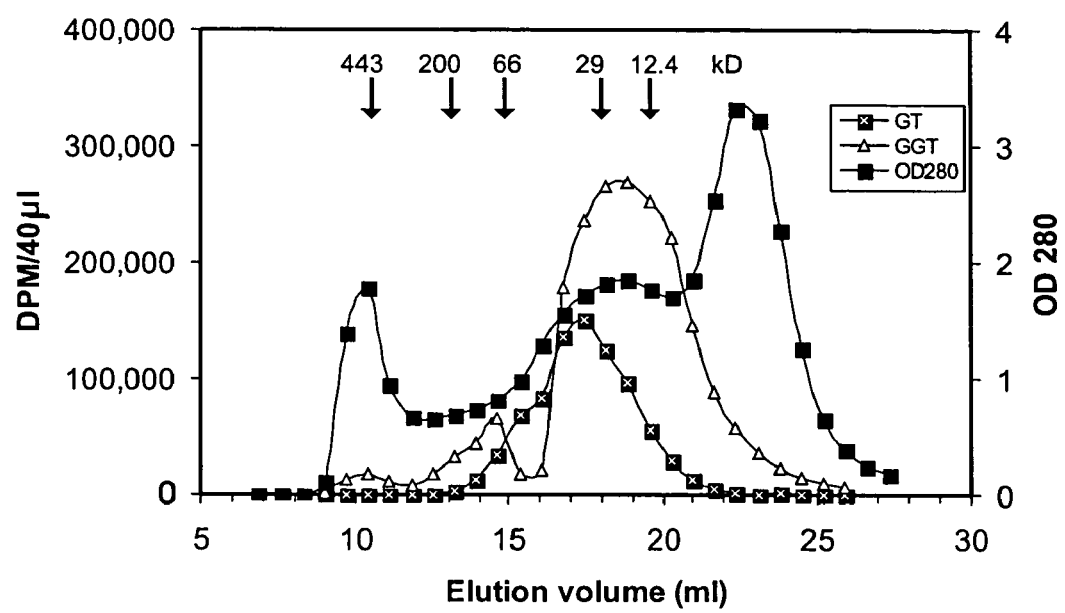
FIG. 13 shows gel filtration of the supernatant of E. coli cells expressing human LH3 protein. The soluble protein produced by the cells were fractionated by Bio-Gel A 0.5 column as described in detail in Example 10. The elution of GT (square with a cross) and GGT (triangle) activities in the fractions are indicated. The elution positions of known protein standards are indicated: apoferritin, amylase, serum albumin, carbonic anhydrase, cytochrome C.

The Galactosyltransferase Activity is Associated with the Molecules Corresponding to the Size of GGT Supernatant of *E. coli* cells expressing human LH3 protein was studied by gel filtration on Bib-Gel A 0.5 column in order to see the molecular weight responsible for the GT activity. As seen in FIG. 13, the GT activity eluted in a wide protein peak having the molecular weight similar but not identical to GGT, GT activity eluting a little earlier than GGT. The elution position of activities corresponded to a molecular weight of about 20-100 kDa, when compared with the elution positions of globular standards. Similar results were obtained when the sample was run through Sephacryl S-300 column (not shown). The addition of protease inhibitors into the homogenization buffer does not have any effect on the activity profiles, suggesting partial proteolysis not being responsible for the wide elution profile in the column.

Collagen Galactosyltransferase Activity Generated by Human LH3 cDNA is Bound to Nickel Column LH3 protein produced by *E. coli* expression vector contained His tag at the amino-terminal end of the molecule, and this enabled us to test if GT activity is bound to nickel affinity column. Our data indicate that GT as well as GGT activities were bound to the column (Table V).

TABLE V

Binding of GT and GGT activities on Nickel-NTA-agarose *E. coli* cells were transfected with LH3 cDNA construct, the cells were homogenized and the soluble supernatant fraction was run through the Nickel-NTA-agarose column. The matrix was then washed with the solution containing 20 mM imidazole, eluted with the solution containing 100 mM, 200 mM and 300 mM imidazole, and solutions were used in the activity measurements.

| Sample | GT activity dpm | GGT activity dpm |
|---|---|---|
| cell supernatant[a] | 6.918.000 | 8.286.000 |
| flow through | 68.000 | 63.000 |
| wash | 274.000 | 3.292.000 |
| 100 mM imidazole elution | 78.000 | 6.640.000 |
| 200 mM imidazole elution | 26.000 | 3.122.000 |
| 300 mM imidazole elution | 4.000 | 450.000 |

[a]The difference between the total apparent GGT activity applied to the affinity column and the total activity eluted in the elution fractions may be partially due to an increase in the activity of the purified matrix.

Figure 14:
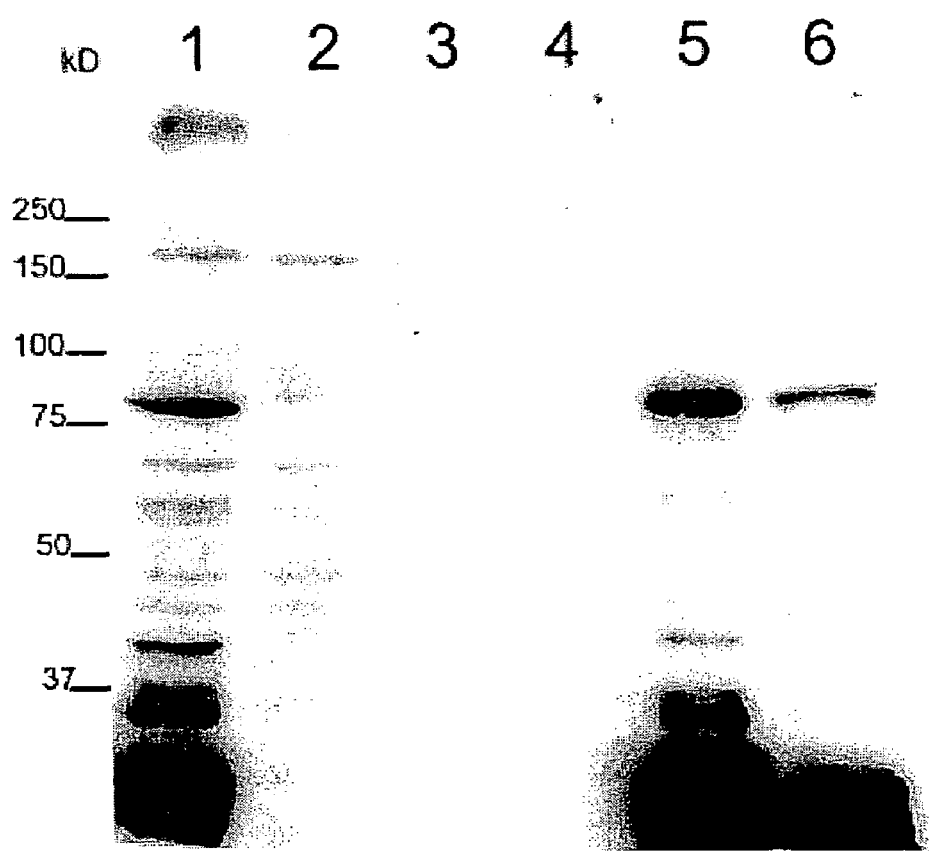
FIG. 14 shows analysis of proteins bound to nickel column. Proteins produced by His-tagged LH3 cDNA construct in E. coli cells were run through the nickel column, and eluted by imidazole as described in Example 10. Analysis of proteins was carried out by Western blotting using anti-His-tag antibody. Lane 1, crude E. coli supernatant; lane 2, flow-through; lane 3 and lane 4, wash; lane 5; elution with 100 mM imidazole, lane 6, elution with 200 mM imidazole.

Elution of the column by 100-300 mM imidazole and analysis of the eluate by immunoblot revealed a protein corresponding to LH3 in size (FIG. 14). Most of the GGT activity were found in the elution fractions, whereas only 1.6% of GT activity was found in the fractions. Our data indicate imidazole as an inhibitor (Table VI) for GT activity, 300 mM solution inhibiting the activity by 60%, the corresponding value for GGT was about 30%. As reported earlier, lysyl hydroxylase was also sensitive to imidazole, 100 mM solution inhibiting LH activity by 55%.

TABLE VI

The effect of imidazole on GT and GGT activity of the protein produced in *E. coli* cells with human LH3 cDNA

| Imidazole | GT activity dpm/mg | GGT activity dpm/mg |
|---|---|---|
| No inhibitor | 760.000 | 667.000 |
| 10 mM | 795.000 | 583.000 |
| 100 mM | 605.000 | 599.000 |
| 300 mM | 310.000 | 459.000 |

Galactosyltransferase Activity in Other Systems Expressing Human LH3 cDNA

We tested human LH3 cDNA expression also in other systems. The expression with baculovirus vector in Sf9 cells revealed GT activity, varying from 50.000 to 170.000 dpm/mg, over the background activity in different experiments. The GT activity was lower than in *E. coli* cells, which is probably due to lower expression level in insect cells. It was remarkable to notice that the insect cells have a reasonable high endogenous GT activity (about 80.000 dpm/mg). It should be noted also that expression of human LH1, LH2a and LH2b cDNAs with baculovirus vector in insect cells did not generated GT activity (not shown).

We produced LH3 protein also in cell free condition by using in vitro translation system. We analyzed the proteins by SDS-PAGE and measured the GT and GGT activities from the reaction mixture. There was one protein synthesized in the translation corresponding to LH3 in SDS-PAGE, and the GGT activity was associated with the protein. GT activity measurements were repeated many times without any results. The addition of dog pancreas microsomes to the incubation mixture revealed indisputably a small but repeatable amount of the activity over background in the reaction mixture (550 dpm/translation mixture), however. Similar data was obtained with the *C. elegans* cDNA.

REFERENCES

Amstrong, L. C., Last, J. A. (1995) Rat lysyl hydroxylase: molecular cloning, mRNA distribution and expression in a baculovirus system. Biochim. Biphys. Acta 1264, 93-102.

Ausubel, F. M., Brent, R., Kingston, R. E., Moore, D. D., Seidman, J. G., Smith, J. A. and Struhl, K. (1988) Current Protocols in Molecular Biology, Greene Publishing Associates/Wiley-Interscience, New York, N.Y.

Brisson et al. (1984), Nature 310:511-514.

Coligan, J. E., Dunn, B. M., Ploegh, H. L., Speicher, D. W., Wingfield, P. T. (1995) Current protocols in protein science, Vol. 1, John Wiley & Sons, USA Gruenwald, S., Heitz, J. Baculovirus expression vector system: Procedures and Methods Manual, Pharmingen, San Diego, 1993.

Hautala, T., Byers, M. G., Eddy, R. L., Shows, T. B., Kivirikko, K. I. and Myllylä, R. (1992) Cloning of human lysyl hydroxylase: complete cDNA-derived amino acid sequence and assignment of the gene (PLOD) to chromosome 1p36.3-p36.2. Genomics, 13, 62-69.

Heikkinen, J., Risteli, M., Wang, C., Latvala, J., Rossi, M., Valtavaara, M., and Myllylä, R. (2000)*J Biol. Chem.* 275, 36158-36163.

Höyhtyä, M., Myllylä, R., Piuva, J., Kivirikko, K. and Tryggvason, K. (1984) Monoclonal antibodies to human prolyl 4-hydroxylase. Eur. J. Biochem., 141, 477-482.

Inouye and Inouye (1985) Nucleic Acids Res. 13:3101-3109.

Kadler, K. (1994) Synthesis and degradation of collagen. Protein Profile, 1, 525-534, 545-549.

Kellokumpu, S., Sormunen, R., Heikkinen, J. and Myllylä, R. (1994) Lysyl hydroxylase, a collagen processing enzyme, exemplifies a novel class of luminally-oriented peripheral membrane proteins in the endoplasmic reticulum. *J. Biol. Chem.*, 269, 30524-30529.

Kielty, C. M., Hopkinson, I. and Grant, M. E. (1993) Collagen: the collagen family: structure, assembly and organization in the extracellular matrix. In Royce PM, Steinmann PM (eds) Connective Tissue and its Heritable Disorders, Wiley-Liss, New York, 103-147.

Kivirikko, K. I. and Myllylä, R. (1979) Collagen glycosyltransferases. Int. Rev. Connect. Tissue Res., 8, 23-72.

Kivirikko, K. I. and MyllyläR. (1982) Post-translational enzymes in posttranslational modification: intracellular processing. Meth. Enzymol., 82, 245-304.

Kivirikko, K. I., Myllylä, R. and Pihlajaniemi, T. (1992) Hydroxylation of proline and lysine residues in collagens and other animal and plant proteins. In Harding J J, Crabbe MJC (eds) Post-translational Modifications of Proteins, CRC Press, Boca Raton, 1-51.

Krol, B. J., Murad, S., Walker, L. C., Marshall, M. K., Clark, W. L., Pinnell, S. R. and Yeowell, H. N. (1996) The expression of a functional, secreted human lysyl hydroxylase in a baculovirus system. J. Invest. Dermatol., 106, 11-16.

Luckow, V. A., Lee, S. C., Barry, G. F., Olins, P. O.(1993) Efficient generation of infectious recombinant baculoviruses by site-specific transposon-mediated insertion of foreign genes into a baculovirus genome propagated in Escherichia coli. J. Virol. 67, 4566-4579.

Maniatis et al. (1989) Molecular Cloning A Laboratory Manual, Cold Spring Harbor Laboratory, New York.

Myllylä, R. (1976) Studies on the mechanism of collagen glucosyltransferase reaction. Eur. J. Biochem., 70, 225-231.

Myllylä, R. (1981) Preparation of antibodies to chick-embryo galactosylhydroxylysyl glucosyltransferase and their use for an immunological characterization of the enzyme of collagen synthesis. Biochim. Biophys. Acta, 658, 299-307.

Myllylä, R., Risteli, L., and Kivirikko, K. I. (1975) *Eur. J Biochem.* 52, 401-410.

Myllylä, R., Anttinen, H., Risteli, L. and Kivirikko, K. (1977) Isolation of collagen glucosyltransferase as a homogenous protein from chick embryos. Biochim. Biophys. Acta, 480, 113-121.

Myllylä, R., Pajunen, L., and Kivirikko, K. I. (1988) *Biochem. J.* 253, 489-496

Myllylä, R., Pihlajaniemi, T., Pajunen, L., Turpeenniemi-Hujanen, T., Kivirikko, K. I. (1991) Molecular cloning of chick lysyl hydroxylase. Little homology in primary structure to the two types of subunit of prolyl 4-hydroxylase. *J. Biol. Chem.* 266, 2805-2810, Myllylä, R., Risteli, L. and Kivirikko, K. (1975) Assay of collagen galactosyl-transferase and collagen glucosyl-transferase activities and preliminary characterization of enzymic reactions with transferases from chick embryo cartilage. Eur. J. Biochem., 52, 401-410.

Passoja, K., Rautavuoma, K., Ala-Kokko, L., Kosonen, T. and Kivirikko, K. I. (1998) Cloning and characterization of a third human lysyl hydroxylase isoform. Proc. Natl. Acad. Sci U S A, 95, 10482-10486.

Pirskanen, A., Kaimio, A. M., Myllylä, R. and Kivirikko, K. I. (1996) Site-directed mutagenesis of human lysyl hydroxylase expressed in insect cells. Identification of histidine residues and an aspartic acid residue critical for catalytic activity. J. Bio. 1 Chem., 271, 9398-9402.

Prockop, D. J. and Kivirikko, K. I. (1995) Collagens: Molecular biology, diseases and potentials for therapy. Annu. Rev. Biochem., 64, 403-434.

Risteli, L., Myllylä, R., Kivirikko, K. I.(1976a) Partial purification and characterization of collagen galactosyltransferase from chick embryos. Biochem J. 155, 145-153.

Risteli, L., Myllylä, R., Kivirikko, K. I.(1976b) Affinity chromatography of collagen glycosyltransferases on collagen linked to agarose. Eur. J. Biochem. 67, 197-202.

Ruther et al. (1983) EMBO J. 2:1791.

Ruotsalainen, H., Sipilä, L., Kerkelä, E., Pospiech, H. and Myllylä, R. (I999) Characterization of cDNAs for mouse lysyl hydroxylase 1, 2 and 3, their phylogenetic analysis and tissue-specific expression in the mouse. Matrix Biol., 18, 325-329.

Sambrook et al. (1989), Molecular Cloning, A Laboratory Manual 2nd Edition, Cold Spring Harbor Laboratory Press, Cold Spring Harbor, N.Y.).

Takamatsu et al. (1987) EMBO J. 6:307-311

Turpeenniemi-Hujanen, T. M., Puistola, U., and Kivirikko, K. I. (1980) *Biochem. J* 89, 247-253.

Valtavaara, M. (1999) Novel lysyl hydroxylase isoforms. Acta Universitatis Ouluensis, A334, 1-63.

Valtavaara, M., Papponen, H., Pirttilä, A. M., Hiltunen, K., Helander, H. and Myllylä, R. (1997) Cloning and characterization of a novel human lysyl hydroxylase isoform highly expressed in pancreas and muscle. *J. Biol. Chem.*, 272, 6831-6834.

Valtavaara, M., Szpirer, C., Szpirer, J. and Myllylä, R. (1998) Primary structure, tissue distribution and chromosomal localization of a novel isoform of lysyl hydroxylase (lysyl hydroxylase 3). *J. Biol. Chem.*, 273, 12881-12886.

Van Heeke & Schuster (1989) J. Biol. Chem. 264:5503-5509.

Wang, C., Valtavaara, M. and Myllylä, R. (2000) Lack of collagen type specificity for lysyl hydroxylase isoforms. DNA and Cell Biology, 19, 71-77.

Yeowell, H. N., Allen, J. D., Walker, L. C., Overstreet, M. A., Murad, S., and Thai, S.-F. (2000) *Matrix Biol*, 19, 37-46.

Yeowell, H. N. and Walker, L. C. (1999) Tissue specificity of a new splice form of the human lysyl hydroxylase 2 gene. Matrix Biol., 18, 179-187.

---

The invention claimed is:

1. A method for glycosylating hydroxylysine residues in polypeptides or peptides having these residues, the method comprising:
  glycosylating a hydroxylysine residue with an enzyme having (a) an amino acid sequence of at least 90% identity to the amino acid sequence set forth to SEQ ID NO: 18, (b) lysyl hydroxylase activity, and (c) glycosyltransferase activity.

2. The method of claim 1, further comprising: expressing in a host selected from the group consisting of a bacterial host, a yeast host, an insect cell, a plant cell and an isolated animal cell a nucleotide sequence encoding said enzyme having lysyl hydroxylase and glycosyltransferase activities.

3. The method according to claim 1 or 2, wherein the glycosylation is carried out in the presence of additives and factors necessary for the function of the glycosyltransferase enzyme.

4. The method according to claim 1, wherein the enzyme has glucosyltransferase activity and/or galactosyltransferase activity.

5. The method according to claim 2, wherein said amino acid sequence originates from an organism comprising polypeptides or peptides having hydroxylysine residues.

6. A method for glycosylating hydroxylysine residues in polypeptides or peptides having these residues, the method comprising:
  (1) expressing in a host a nucleotide sequence encoding an enzyme having lysyl hydroxylase and glycotransferase activities; and
  (2) glycosylating a hydroxylysine residue with said enzyme, wherein said enzyme is characterized by having:
    (a) an amino acid sequence of at least 90% identity to human LH3 (SEQ ID NO: 18);
    (b) a iysyi hydroxylase activity; and
    (c) a glycosyltransferase activity.

7. The method according to claim 1, wherein the enzyme is encoded by a nucleotide sequence selected from the group consisting of:
  (a) the nucleotide sequence set forth in SEQ ID NO 17;
  (b) a nucleotide sequence encoding a polypeptide having the amino acid sequence set forth in SEQ IDNO 18;
  (c) a nucleotide sequence which differs from the nucleotide sequences of (a) and/or (b) due to the degeneracy of the genetic code; and
  (d) a nucleotide sequence that encodes a polypeptide having an amino acid sequence which shows at least 90% identity to SEQ ID NO 18.

8. The method according to claim 2, wherein said enzyme is secreted from said host.

9. The method according to claim 2, wherein the nucleotide sequence encoding lysyl hydroxylase is expressed in *E. coli*.

10. The method according to claim 2, wherein the nucleotide sequence encoding lysyl hydroxylase is expressed in an insect cell.

11. The method according to claim 1, wherein the enzyme is in multimeric or monomeric form.

12. The method according to claim 1, wherein the hydroxylysine of collagen, collagenous protein, collagen-type protein or other protein or synthetic or partly synthetic protein is glycosylated.

13. The method according to claim 1, wherein the enzyme has the amino acid sequence set forth in SEQ ID NO: 18.

14. The method according to claim 2, wherein the nucleotide sequence comprises the sequence set forth in SEQ ID NO: 17.

15. A method for glycosylating hydroxylysine residues in polypeptides or peptides having these residues, the method comprising: glycosylating a hydroxylysine residue with an enzyme having (1) an amino acid sequence of at least 90% identity to the amino acid sequence set forth to SEQ ID NO: 18 and (2) glycosyltransferase activity.

16. The method of claim 15, wherein said enzyme does not have lysyl hydroxylase activity due to a genetic modification of SEQ ID NO: 18, and wherein said enzyme has glycosyltransferase activity.

17. The method according to claim 15 or 16, wherein the glycosylation is carried out in the presence of additives and factors necessary for the function of the glycosyltransferase enzyme.

18. The method according to claim 15 or 16, wherein the hydroxylysine of collagen, collagenous protein, collagen-type protein or other protein or synthetic or partly synthetic protein is glycosylated.

19. The method according to claim 6, wherein said enzyme is characterized by having at least 90% identity to amino acids 25-738 of human LH3 (SEQ ID NO: 12).

* * * * *